United States Patent
Tyagi et al.

(10) Patent No.: US 11,459,603 B2
(45) Date of Patent: Oct. 4, 2022

(54) TARGET MEDIATED IN SITU SIGNAL AMPLIFICATION WITH DUAL INTERACTING HAIRPIN PROBES

(71) Applicant: Rutgers, The State University of New Jersey, New Brunswick, NJ (US)

(72) Inventors: Sanjay Tyagi, New York, NY (US); Salvatore A. E. Marras, Roselle Park, NJ (US)

(73) Assignee: RUTGERS, THE STATE UNIVERSITY OF NEW JERSEY, New Brunswick, NJ (US)

(*) Notice: Subject to any disclaimer, the term of this patent is extended or adjusted under 35 U.S.C. 154(b) by 257 days.

(21) Appl. No.: 16/615,922

(22) PCT Filed: May 23, 2018

(86) PCT No.: PCT/US2018/034150
§ 371 (c)(1),
(2) Date: Nov. 22, 2019

(87) PCT Pub. No.: WO2018/217905
PCT Pub. Date: Nov. 29, 2018

(65) Prior Publication Data
US 2020/0140936 A1 May 7, 2020

Related U.S. Application Data

(60) Provisional application No. 62/510,045, filed on May 23, 2017.

(51) Int. Cl.
| | |
|---|---|
| C12Q 1/6841 | (2018.01) |
| C12N 15/11 | (2006.01) |
| C12Q 1/682 | (2018.01) |
| C12Q 1/6827 | (2018.01) |
| C12Q 1/6876 | (2018.01) |

(52) U.S. Cl.
CPC ............ *C12Q 1/6841* (2013.01); *C12N 15/11* (2013.01); *C12Q 1/682* (2013.01); *C12Q 1/6827* (2013.01); *C12Q 1/6876* (2013.01); *C12N 2310/531* (2013.01)

(58) Field of Classification Search
CPC .. C12Q 1/68; C12Q 1/6876; C12N 2310/531; C07H 21/00
See application file for complete search history.

(56) References Cited

U.S. PATENT DOCUMENTS

| | | | | |
|---|---|---|---|---|
| 5,424,413 | A * | 6/1995 | Hogan ............... | C12N 15/1068 435/6.1 |
| 5,635,400 | A * | 6/1997 | Brenner .................. | C12N 15/10 506/41 |
| 2001/0053519 | A1 * | 12/2001 | Fodor ..................... | B82Y 30/00 536/24.1 |
| 2002/0064779 | A1 * | 5/2002 | Landegren ............. | G01N 33/58 435/6.1 |
| 2002/0137036 | A1 * | 9/2002 | Sorge ............... | C12Q 2531/113 435/6.11 |
| 2003/0129611 | A1 * | 7/2003 | Bao ....................... | C12Q 1/6818 435/6.11 |
| 2005/0287526 | A1 * | 12/2005 | Landegren ........... | C12Q 1/6848 435/6.12 |
| 2006/0228733 | A1 * | 10/2006 | Pierce ............... | C12Q 2525/301 435/6.14 |
| 2011/0223585 | A1 * | 9/2011 | Gullberg .............. | C12Q 1/6804 435/5 |
| 2011/0313030 | A1 * | 12/2011 | Dirks ...................... | A61P 31/18 514/44 R |
| 2012/0322067 | A1 * | 12/2012 | Nadeau .................. | C12Q 1/682 435/6.11 |
| 2013/0261196 | A1 * | 10/2013 | Diamond ............... | C12Q 1/708 514/789 |
| 2014/0194311 | A1 * | 7/2014 | Gullberg .............. | C12Q 1/6804 506/9 |
| 2015/0361475 | A1 | 12/2015 | Marras et al. | |
| 2016/0289750 | A1 * | 10/2016 | Landegren ........... | C12Q 1/6816 |
| 2016/0369321 | A1 * | 12/2016 | Landegren ........... | C12Q 1/6804 |
| 2016/0376642 | A1 * | 12/2016 | Landegren ........... | C12Q 1/6848 435/6.11 |
| 2017/0009278 | A1 * | 1/2017 | Soderberg .......... | G01N 33/5308 |
| 2017/0211133 | A1 * | 7/2017 | Landegren ........... | C12Q 1/6816 |

FOREIGN PATENT DOCUMENTS

| | | |
|---|---|---|
| JP | 2013-511292 A | 4/2013 |
| WO | 2009017861 A2 | 2/2009 |
| WO | 2015118029 A1 | 8/2015 |

OTHER PUBLICATIONS

Bi et al., .Hyperbranched Hybridization Chain Reaction for Triggered Signal Amplification and Concatenated Logic Circuits. Angewandte Chemie International Edition 54 (28) :8144-8148. (Year: 2015).*
Chen et al. Nanoscale Imaging of RNA with Expansion Microscopy. Nature Methods, 13(8) : 679-684 and Supplemental Information. (Year: 2016).*
Choi et al., Programmable in Situ Amplification tor Multiplexed Imaging of mRNA Expression, Nature Biotechnoloy, 28(11) : 1208-1212 (Year: 2010).*
Choi et al. Next-Generation in Situ Hybridization Chain Reaction: Higher gain, Lower Cost, Greater Durability. ACS Nano, 8( 5) : 4284-4294. (Year: 2014).*

(Continued)

*Primary Examiner* — Ethan C Whisenant
(74) *Attorney, Agent, or Firm* — Fox Rothschild LLP

(57) ABSTRACT

The present invention relates to the detection of nucleic acids sequences in situ using hybridization probes and generation of amplified hybridization signals, wherein background signal is reduced and sensitivity is increased.

15 Claims, 15 Drawing Sheets
Specification includes a Sequence Listing.

(56) References Cited

OTHER PUBLICATIONS

Huang et al. A supersandwich fluorescence in situ hybridization strategy for highly sensitive and selective mRNA imaging in tumor cells. Chemical Communications 52(2): 370-373 (Year: 2016).*

Koos et al.,Koos et al. Proximity-Dependent Initiation of Hybridization Chain Reaction Nature Communications 6(7294) : 1-10. (Year: 2015).*

Shah et al.Single-Molecule RNA Detection at Depth via Hybridization Chain Reaction and Tissue Hydrogel Embedding and Clearing. Development 143(15) : 2862-2867. (Year: 2016).*

Matthews et al., Review : Analytical Strategies for the use of DNA probes 169:1-25 (Year: 1988).*

Yan et al: "Isothermal Amplified Detection of DNA and RNA", Molecular Biosystems, Jan. 1, 2014, vol. 10, No. 5, p. 970, XP055324229, DOI: 10.1039/c3mb70304e.

Jung et al: "Diagnostic Applicatoins of Nucleic Acid Circuits", Accounts of Chemical Research, May 14, 2019, vol. 47, No. 6, pp. 1825-1835, XP055488599, DOI: 10.1021/ar500059c.

Choi et al., "Next-Generation in Situ Hybridization Chain Reaction: Higher gain, Lower Cost, Greater Durability," ACS Nano (2014); 8(5):4284-4294.

Bi et al., "Hyperbranched Hybridization Chain Reaction for Triggered Signal Amplification and Concatenated Logic Circuits," Angewandte Chemie International Edition (2015); 54(20):8144-8148.

Chen et al., "Nanoscale Imaging of RNA with Expansioin Microscopy," Nature Methods (2016); 13(8):679-684.

Koos et al., "Proximity-Dependent Initiation Hybridization Chain Reaction," Nature Communications (2015); 6(7294):1-10.

Shah et al., "Single-Molecule RNA Delection at Depth via Hybridization Chain Reaction and Tissue Hydrogel Embedding and Clearing," Development (2016); 143(15):2862-2867.

* cited by examiner

Guide RNA Expressed in HeLa cell Nucleus

TARGET MEDIATED IN SITU SIGNAL AMPLIFICATION WITH DUAL INTERACTING HAIRPIN PROBES

CROSS REFERENCE TO RELATED APPLICATION

This application claims priority to U.S. Provisional Application No. 62/510,045 filed on May 23, 2017. The content of the application is incorporated herein by reference in its entirety.

FIELD OF THE INVENTION

The present invention relates generally to the detection of nucleic acids sequences in situ using hybridization probes and generation of amplified hybridization signals.

BACKGROUND OF THE INVENTION

Fluorescence in situ hybridization (FISH) is a well-known technique that is used, for example, in detecting RNAs in individual fixed, permeabilized cells. FISH methods to detect cells having low-copy-number RNA targets, that is, detection at the cellular level, typically include signal amplification in order to generate detectable fluorescence. Such methods are reviewed in Moter et al. (2000) J. Microbiol. Meth. 41: 85-112. For example, digoxigenin (DIG)-labeled probes can be detected by the reaction of the DIG label with an anti-DIG antibody coupled to alkaline phosphatase, followed by reaction of the alkaline phosphatase with a substrate in a color-forming reaction. Certain FISH methods have been shown to be capable of detecting single RNA molecules (sm-FISH). Sm-FISH requires the generation of a sufficiently high, localized fluorescent signal that is sufficiently intense and sufficiently above background to enable detection of a single RNA molecule as a detectable fluorescent spot. Two successful methods for sm-FISH utilize sets of multiple nucleic acid hybridization probes for a target sequence, either a small number (five or six) of long, multiply-labeled probes (Femino et al. (1998) Science 280: 585-590) or a large number (e.g., 48) of short probes, all singly-labeled with the same fluorophore, that tile along a target sequence (Raj et al. (2008) Nature Methods 5:877-879). Sets of the latter probes are commercially available as Stellaris FISH probe sets from LGC Biosearch Technologies. Another well-known technique for improving sensitivity sufficiently to enable sm-FISH is signal amplification by the hybridization chain reaction (HCR), a fluorescent signal amplification method developed by Dr. Niles A. Pierce and colleagues of the California Institute of Technology, Pasadena, Calif. (U.S.A.). Yet another technique for improving signal intensities for in situ hybridization reactions is signal amplification by rolling circle amplification (RCA) (Lizardi et al. (1998) Nature Genetics 19:225-232; Soderberg et al (2006) Nature Methods 3:995-1000; and Larsson et al. (2010) Nature Methods 5: 395-7).

In signal amplification by HCR, a linear (or random coil) hybridization probe that includes (or is tagged with) an extension called an "initiator sequence" causes two fluorescently labeled hairpin oligonucleotides (monomers) to polymerize by hybridization, creating a multiply fluorophore-labeled, double-stranded polymer that is tethered to the target sequence complementary to the hybridization probe via its hybridization. Both DNA and RNA have been used to construct the hybridization probe and the HCR hairpin oligonucleotides. A more detailed explanation of HCR appears below in connection with the description of FIG. 1.

Variants of the basic HCR method for a single target sequence include the use of a set of multiple probes that carry the same initiator sequence and that hybridize along a target sequence; probes with two initiator sequences, an initiator for a first of the HCR hairpin oligonucleotides on one end and an initiator for the other hairpin oligonucleotide on the other end; or both (Choi et al. (2014) ACS NANO 8: 4284-4294 at 4288, right column). Choi et al. used both: a set of five two-initiator DNA probes per RNA target sequence. Another variant is multiplex detection of multiple target sequences using a set of probes and a different and differently colored pair of HCR monomers for each target sequence. Choi et al., for example, described multiplex detection of five targets using for each target sequence a set of five, two-initiator probes and a unique pair of HCR monomers carrying spectrally distinct Alexa Fluor fluorophores.

Examples of RNA detection in fixed, permeabilized cells (zebra fish embryos) utilizing HCR amplification are reported in Choi et al. (2014). A first method utilized RNA probes (81 nucleotides long, comprising a 50-nucleotide (50-nt) target-complementary or "recognition" sequence, a 5-nt spacer, and a 26-nt initiator sequence) and RNA HCR hairpin oligonucleotide monomers (52 nucleotides long, each comprising a 10-nt toehold sequence, a 16-bp stem, and a 10-nt loop). A second, "next generation" method utilized DNA probes (91 nucleotides long, comprising a 50-nt target-complementary sequence, a 5-nt spacer, and a 36-nt initiator sequence (including a 12-nt toehold-complementary sequence); or 132 nucleotides long, with a spacer and initiator on each end of the target-complementary sequence), and DNA HCR hairpin oligonucleotide monomers (72 nucleotides long, comprising a 12-nt toehold sequence, a 24-base pair (24-bp) stem, and a 12-nt loop). For hybridization with whole-mount zebra fish embryos, the embryos were fixed in 1 mL of 4% paraformaldehyde, washed with PBS, and permeabilized with a series of methanol washes. For RNA probes, hybridization was performed overnight at 55° C. in buffer containing 50% formamide. For RNA hairpin monomers, HCR amplification was overnight at 45° C. in a buffer containing 40% formamide. For DNA probes, the hybridization was performed overnight in buffer containing 50% formamide. For DNA hairpin monomers, hybridization was overnight at room temperature in buffer containing no formamide (only sodium chloride citrate (SSC), Tween 20 and dextran sulfate).

RNA detection in fixed and permeabilized cultured cells, zebrafish embryos, and mouse brain slices using HCR amplification according to Choi et al. (2014) was also reported by Shah et al. (2016). For hybridization with embryos they used a set of thirty-nine one-initiator DNA sm-FISH probes (≥5-nt gaps between probes) comprising a 30-nt target-complementary sequence, a 5-nt spacer, and a 36-nt initiator sequence; for cultured cells and brain slices they used a set of from twenty-one to thirty-two DNA sm-FISH probes comprising a 20-nt target-complementary sequence, a 4-nt spacer, and a 36-nt initiator sequence. HCR amplification conditions were adjusted to limit HCR polymerization to ~20-to-40 hairpins per polymer chain. For cultured cells HCR amplification was performed for 45 minutes at room temperature with 120 nM of each hairpin monomer in buffer comprising dextran sulfate and SSC. For embryos HCR amplification was performed for one hour at room temperature with 60 nM of each hairpin monomer in buffer comprising dextran sulfate, SSC, and Tween 20. For brain slices HCR amplification was performed for 5-to-6 hours at room temperature with 120 nM of each hairpin monomer in buffer comprising dextran sulfate and SSC.

Current limitations of HCR include the generation of false signals (also referred to as background signals). Tagged hybridization probes that remain non-specifically bound after washing and at the time of initiation of HCR also produce detectable signals that constitute the background signals or false positives. The existence of such signals have been pointed out by several references, although, their methods of determination of background signals were different from each other. Choi et al. (2014) pointed out that the extent of these non-specific background signals depends on the lengths and number of initiator-containing hybridization probes. In their Table S2 Choi et al. (2014) report signal and background levels for one of their HCR detection experiments. The average signal levels were 2010 units, and background levels (referred to as non-specific detection) were 28 units.

Background signals were also observed by Chen et al. (2016) who in their Supplementary Table 3 report signal and background levels in terms of the number of spots that they counted in high magnification imaging. They imaged a region of mouse brain for expression of mRNA from gene Dlg4. The number of spots obtained from using probes complementary to the Dlg4 mRNA was 9,795 in a particular area of the brain. When missense probes (that had the same sequence as in the mRNA and therefore could not bind to the RNA) were used instead, 1,540 spots were detected in the same region. Similarly a probe against a non-existent RNA yielded 1,209 spots in this region. The latter two numbers represent the levels of background signals and the first number represents the specific signals.

Shah et al. (2016) also observed significant background signals created by amplification of non-specifically bound probes tagged with HCR initiators. They analyzed background levels by imaging Pgk1 mRNA simultaneously with three sets of probes: one set of probes tagged with an initiator that elicits signals from one set of HCR hairpins labeled with Alexa 647, a second set of probes tagged with a second initiator that elicits signals from a second set of HCR hairpins labeled with Alexa 594, and a third set of probes that were directly labeled with Cy3b. Their results show that 36% of Alexa 647 and 27% of Alexa 594 HCR and 20% of Cy3b spots stem from non-specifically bound probes (false positive signals) (Figure S3B of Shah et al. 2016). Furthermore, Example 1 of this document describes additional examples of false positive signals that are obtained with HCR performed with passively tagged probes.

A further limitation of HCR is that it cannot be used to distinguish between targets differing from each other by a single nucleotide.

Signal amplification by RCA is normally performed by first forming a circular template in a template-dependent manner from a single stranded linear DNA oligonucleotide that binds to the target in such a manner that its 5' and the 3' termini are placed next to each other for a subsequent ligation reaction (Lizardi et al. (1998) Nature Genetics 19:225-232 and Larsson et al. (2010) Nature Methods 5: 395-7). The circular DNA molecule thus created is then used as a template for rolling circle amplification (RCA) by a DNA primer and a DNA polymerase. Copying of the circular template generates numerous concatenated copies of the complement of the template sequence, which is then detected by a fluorescent probe. A more detailed explanation of RCA appears below in connection with the description of FIG. 2.

An object of this invention is to reduce background and thereby increase the sensitivity of HCR signal-amplification detection methods.

Another object of this invention is RCA signal-amplification detection methods that generate concatenated amplicons tethered to a hybridization probe, wherein background signal is reduced and sensitivity is increased.

Another object of this invention is an HCR detection method that can be used to distinguish between targets differing from each other by as little as a single nucleotide.

SUMMARY OF THE INVENTION

Probes in which an HCR initiator is tagged to a target specific region are known. Although such probes allow amplified detection of in situ hybridization, they are prone to generation of non-specific signals and cannot be used for discrimination and detection of two alleles in the same cell. This invention includes probe pairs in which the HCR initiator is sequestered within hairpins and cannot initiate amplification until the probes are bound to their correct target at the intended location. Furthermore, probe pairs according to this invention allow development and detection of amplified signals from single target molecules that differ from each other by a single nucleotide polymorphism. Both the wild-type and the mutant-type sequence can be detected simultaneously. This invention includes interacting hairpin hybridization probe pairs for initiating signal amplification in fixed and permeabilized cells by HCR.

This invention also includes RCA methods that utilize a probe-tethered primer and a circular template for signal amplification, wherein the primer is included in a probe pair such that it is sequestered within a hairpin and cannot initiate amplification until the probes are bound to their correct target at the intended location. This invention includes interacting hairpin hybridization probe pairs for initiating signal amplification in fixed and permeabilized cells by RCA.

This invention includes oligonucleotide sets of one or more pairs of such probes plus either one or more pairs of HCR oligonucleotide monomers or additional oligonucleotides for RCA. This invention also includes reaction mixtures containing fixed and permeabilized cells and at least one pair of interacting hairpin hybridization probes, reaction mixtures containing fixed and permeabilized cells, hybridized probe pairs that have interacted to generate at least one HCR initiator sequence, and at least one pair of HCR monomers. This invention further includes assay kits for performing a single-molecule fluorescence hybridization (sm-FISH) assay by a method of this invention, wherein a kit contains at least an oligonucleotide set as described above plus at least one buffer for hybridization and amplification reactions. Interacting hairpin probe pairs and HCR monomers comprise natural or modified nucleotides, preferably comprise natural nucleotides, more preferably consisting of DNA nucleotides.

Methods according to this invention are FISH methods for DNA or RNA targets, including particularly methods for, or capable of, single-molecule detection (single-molecule FISH (sm-FISH)). Examples of categories of RNAs include without limitation, messenger RNAs, ribosomal RNAs, small nuclear RNAs, micro RNAs, circular RNAs, non-coding RNAs, pre-RNAs, and spliced or alternatively spliced RNAs. In FISH methods for detecting RNA or DNA in individual cells, cells are probed with hybridization probes after being fixed, permeabilized, and washed. FISH techniques for fixing and permeabilizing cells in cell cultures and tissue are well known, as is washing. Methods according to this invention are not limited to any particular technique for fixing and permeabilizing cells, or to any particular washing step.

In RNA or DNA FISH detection methods according to this invention, fixed and permeabilized cells are probed with at least one pair of interacting hairpin hybridization probes that interact when hybridized adjacently on an RNA or DNA target sequence in an target strand to generate a single-stranded HCR initiator sequence. Such probing comprises incubating the at least one probe pair with the fixed and permeabilized cells to hybridize the probe pair to their target sequence, and incubating hybridized probes to generate an initiator sequence by their interaction. Both probe hybridization and probe interaction may be performed in a single incubation. Reaction of the initiator, after washing to remove excess unhybridized probes, with one of a pair of HCR hairpin monomers, leads to signal amplification by HCR. Alternatively signal amplification is achieved through RCA.

Each pair of interacting hairpin probes includes a first hairpin-containing probe having segments (nucleic acid sequence elements) in the following order, whether 5'→3' or 3'→5': a first hairpin stem arm sequence, a loop sequence complementary to a first subsequence of a selected nucleic acid (RNA or DNA) target sequence, and a second hairpin stem arm that is complementary to the first stem arm that includes a single-stranded extension. We refer to this probe variously as an "arm-donating hairpin probe" or an "arm-donating beacon," which we sometimes abbreviate as "DB". We refer to its second stem arm as a "donating arm." Each pair of interacting hairpin probes also includes a second hairpin-containing probe having sequence elements in the following order, whether 5'→3' or 3'→5': a terminal target-complementary sequence that is complementary to a second subsequence of the target sequence adjacent to the first subsequence, a first hairpin stem arm sequence that is complementary to the donating arm of the first hairpin-containing probe, a hairpin loop sequence, and a second hairpin stem arm sequence that is complementary to at least a portion of the first hairpin stem arm. We refer to this probe as an "arm-acceptor hairpin" probe or "arm-acceptor probe." Its second stem arm has a single-stranded extension that includes the terminal target-complementary sequence and in some embodiments also includes a toehold sequence. Regarding orientation, the second hairpin stem arm (the donating arm) of the arm-donating hairpin probe and its complement in the arm-acceptor probe are inward-facing, that is, proximate one another, when the probe pair is hybridized on the target sequence. With reference to the second panel in FIG. 4, this means that, as donating arm e', f' is at the 5' end of arm-donating hairpin probe 49, its interacting arm-acceptor probe 50 has its hairpin e,f,g',f' at the 3' end; and that, as donating arm d',b' is at the 3' end of arm-donating hairpin probe 48, its interacting arm-acceptor probe 47 has its hairpin d,b,a',b' at the 5' end.

The first hairpin-containing probe, the arm-donating probe, functions like a well-known molecular beacon probe, which has a stem-and-loop structure and opens when the loop sequence hybridizes to its complementary target sequence (Tyagi and Kramer (1996) Nature Biotechnology 14: 303-308; Tyagi et al. (1998) Nature Biotechnology 16: 49-53). Hybridization of the loop of the arm-donating beacon to the target sequence separates its stem arms, rendering the second stem arm sequence and its extension single-stranded and thereby able to interact with the second hairpin-containing probe, the arm-acceptor probe. Interaction separates the stem arms of the arm-acceptor probe, rendering its loop sequence and second arm sequence single-stranded and able to function as an initiator for HCR amplification or as initiator (priming sequence) for RCA, as desired.

As noted above, the first arm sequence of the second hairpin-containing probe, the arm-acceptor probe, may include a single-stranded extension of the first arm sequence not only a target-complementary sequence but also, between the stem and the target-complementary sequence, a toehold sequence. In such embodiments (see FIG. 4) the toehold sequence is sufficiently complementary to the stem-forming portion of the donating arm of the first probe that, after the donating arm is rendered single-stranded, its stem portion hybridizes to the toehold sequence. Strand displacement follows, opening the stem of the second probe. In other embodiments (see FIG. 5) there is no toehold sequence, but interaction nevertheless opens the stem of the arm-acceptor probe. Embodiments of both types are described below and in the Examples.

Only when the two probes bind, or hybridize, adjacently on the target sequence, do they interact to generate a single-stranded HCR initiator sequence or an RCA primer sequence. If the loop sequence of the second probe is allele-discriminating, that is, it does not hybridize and open the probe if there is a single nucleotide mismatch, and its target sequence includes a nucleotide that differs between alleles, HCR or RCA amplification will result only from the allelic target sequence that is perfectly complementary to the probe.

An important aspect of this invention is that the initiator of amplification is "sequestered" or "masked" in free or non-specifically bound probes but is "revealed" or "unmasked" when the probes are bound to their specific target.

In detection methods according to this invention an HCR initiator sequence generated by a pair of interacting hairpin probes as described above initiates a signal amplification reaction by HCR. In HCR a pair of hairpin oligonucleotide monomers labeled with at least one copy, preferably a single copy, of the same fluorophore, once initiated by reaction with an HCR initiator, interact with one another by hybridization and strand displacement to generate a double-stranded extension of the initiator sequence. The extension is known as an HCR polymer. It is multiply fluorophore labeled, thereby producing an amplified fluorescent signal as compared to a directly fluorophore-labeled probe. It is tethered directly to the arm-acceptor hairpin probe by hybridization and indirectly tethered to that probe's target sequence by hybridization of the probe to the target sequence. A schematic depiction of HCR is shown in FIG. 2. See Choi et al. (2014) ACS Nano 8: 4284-4294 for a description of HCR.

In detection methods according to this invention a single pair of interacting hairpin probes may generate a single copy of an HCR initiator, or additional (one or more) pairs of interacting hairpin probes may be used to generate multiple copies of the HCR initiator. When multiple probe pairs are utilized to detect a single target sequence, the simplest construction is to change only the target-binding sequences, thereby permitting use of a single HCR monomer pair.

In certain embodiments two probe pairs can share a single arm-donating probe. Even though there are only three probes, there are two probe pairs, one pair including the arm-donating probe and a first arm-acceptor probe, and a second pair including the arm-donating probe and a second arm-acceptor probe. In such embodiments one arm-acceptor probe hybridizes to the target sequence 5' of the binding site of the arm-donating probe, and a second arm-acceptor hybridizes to the target sequence 3' of the binding site of the arm-donating probe. When the arm-donating probe hybridizes to the target sequence, making its stem arms single stranded, the two freed arms interact with both arm-acceptor probes, thereby releasing two HCR initiators. The two freed HCR initiators then initiate HCR amplification by a single pair of HCR monomers whereby not one but two HCR polymers grow from the common arm-donating probe. This results in a stronger fluorescent signal from a single copy of the target sequence.

Methods according to this invention further include sm-FISH assays, both qualitative and quantitative assays, for both of two allelic variants that differ by as little as a single nucleotide, for example, a wild-type sequence and a mutant sequence containing a single-nucleotide polymorphism or variation (SNP or SNV). Such methods utilize two interacting hairpin probe pairs, wherein each pair contains an arm-donating beacon probe and an arm-acceptor hairpin probe. The loop sequence of each arm-donating beacon probe is complementary to a different allelic variant of the target sequence. For example, the loop sequence of one of the arm-donating beacon probes may hybridize to a wild-type target sequence but not to a mutant sequence having a SNP, and the loop sequence of the second arm-donating beacon probe may hybridize the mutant sequence but not to the wild-type sequence. Thus, for a given RNA target strand, only one of the arm-donating beacon probes will bind to a given target sequence. Although, only one of the arm-donating beacon probes binds to a given target, both arm-acceptor probes bind to the same target, and they do so on either side of the bond arm-donating beacon (FIGS. 3 and 4). The arm-acceptor hairpin probe having 3' initiator sequences binds to the target sequence that is 3' to where the loop of the arm-donating beacon probe binds. The arm-acceptor hairpin probe having a 5' initiator sequence binds to the target sequence that is 5' to where the loop of the second arm-donating beacon probe binds. The toehold and the stem and loop sequences of the two arm-acceptor hairpin probes are different, whereby each interacting probe pair generates a different single-stranded initiator sequence that initiates HCR with a different monomer pair labeled with a differently colored fluorophore label and thus generates detectably different HCR multimeric product. The four probes and how they interact with the targets and one other are depicted in FIGS. 3-5.

Since both allelic variants may be present on different RNA strands in a heterozygotic cell, signals from both HCR variants will be observed in such a cell. On the other hand, homozygotic cell will exhibit only one of the signals. Finally, in cancer cells in which one of the alleles is amplified relative to the other allele and is expressed to a greater extent, the intensity of the signal of the corresponding HCR will be greater than the intensity of the signal from the HCR corresponding to the minor allele.

Because a single-stranded HCR initiator sequence is not present in a reaction mixture unless it is generated by the interaction of an adjacently hybridized probe pair, the at least one probe pair and the at least one HCR monomer pair can be added together to the fixed and permeabilized cells. However, in certain preferred methods, the at least one probe pair is added first, and unbound probes are removed by washing before HCR monomers are added. sm-FISH methods of this invention include detection of HCR polymers. After HCR polymerization, unused HCR monomers and unbound probe pairs are removed by washing. Fluorescence is detected by microscopic techniques or by flow cytometry.

In some situations rather than targeting the entire mRNA target length with tiled probes for sm-FISH, as is done with tiled Stellaris probe sets of, it may be necessary or advantageous to use a small portion of the target sequence (40-50 nt). For example, in archived formalin-fixed, paraffin-embedded (FFPE) samples the target mRNA may be degraded and be present only as small fragments. In other cases, the target may be a small exon that is not long enough to allow tiling of many sm-FISH probes. In still other cases, the target may include a small variation that needs to be detected. In these cases it will be sufficient and advantageous to use a single pair of interacting hairpin probes or two pairs that share a common arm-donating probe.

The background-free amplification of signals achieved through this invention allows for more reliable detection of target nucleic acids than is achieved by current HCR methods. The reduction in background signals also allows detection of less abundant targets, detection of targets over natural autofluorescence of cells and tissues, and detection of multiple targets in the same cells by combinatorial color-coding. In combinatorial color-coding based multiplexing, each target is detected by using mixtures of probes that give rise to a combination of colors. However, since each target signal is divided in multiple channels, this requires that probes yield strong signals for each channel. The probes of this invention create strong signals to satisfy the needs of combinatorial color-coding based multiplexing.

DETAILED DESCRIPTION

Definitions

Figure 1:
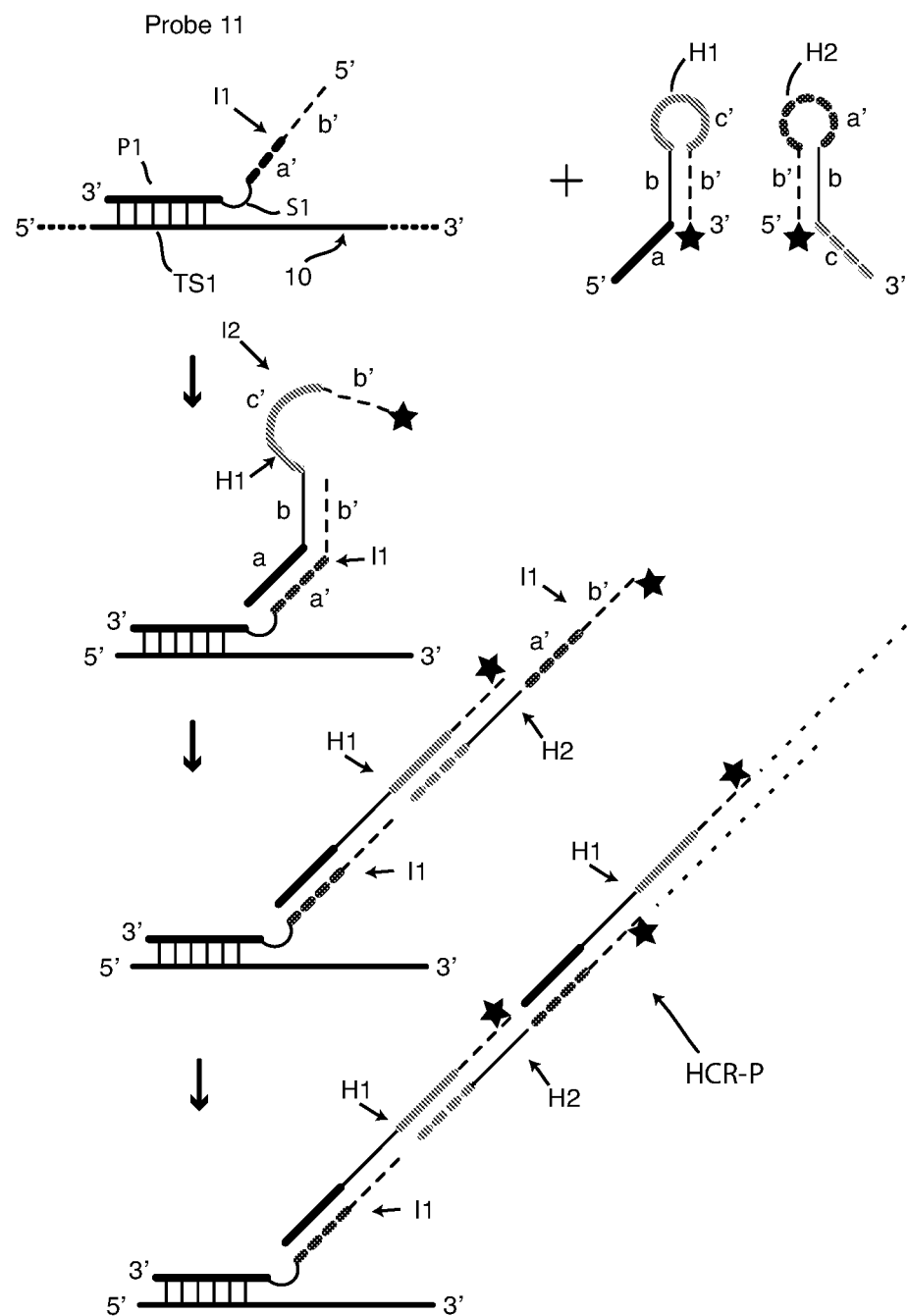
FIG. 1 is a schematic depiction of detection of a nucleic acid target sequence with a passively tagged hybridization probe and HCR signal amplification with HCR monomers.

"RNA". As used in the specification and claims of this patent application, when referring to a target sequence, "RNA" includes all variants, for example, messenger RNA, ribosomal RNA, coding or noncoding RNA, linear or circular RNA, transfer RNA, microRNA, spliced or alternately spliced RNA, and pre-RNA. As used in the specification and claims of this patent application, when referring to interacting hairpin probes, "RNA" includes oligoribonucleotides with natural ribonucleotides and phosphodiester bonds, and also includes oligoribonucleotides containing one or more non-natural nucleotides (for example, PNA nucleotides, LNA nucleotides or 2'-O-methyl ribonucleotides).

"DNA". As used in the specification and claims of this patent application, when referring to interacting hairpin probes, "DNA" includes oligodeoxyribonucleotides with natural deoxyribonucleotides and phosphodiester bonds, and also includes oligodeoxyribonucleotides containing one or more non-natural nucleotides (for example, PNA nucleotides, LNA nucleotides or 2'-O-methyl ribonucleotides) and non-natural backbones.

"Nucleic acid." As used in the specification and claims of this patent application, when referring to a target molecule or target sequence, "nucleic acid" means RNA or DNA, including in either case oligonucleotides with natural nucleotides and phosphodiester bonds; or when referring to interacting hairpin probes, including RNA and DNA oligonucleotides with natural nucleotides and phosphodiester bonds, and also including RNA and DNA oligonucleotides containing one or more non-natural nucleotides (for example, PNA nucleotides, LNA nucleotides or 2'-O-methyl ribonucleotides).

"Adjacently". As used in the specification and claims of this patent application to describe the hybridization of pairs of interacting hairpin probes, "adjacently" means sites that are sufficiently close to each other to permit interaction between interacting hairpin probes. A preferred choice is "immediately adjacent" in which there is no gap between the binding sites of two interacting probes.

"Target molecule," "target strand," "target sequence," and "target-sequence region" or "subsequence". As used in the specification and claims of this patent application, a target molecule or target strand is a nucleic acid strand, either RNA or DNA, that contains one or more target sequences. "Target sequence" is a sequence in an RNA or DNA target strand that is being probed, either by one or more conventional passively tagged probes or by one or more pairs of interacting hairpin probes of this invention, where signal amplification leads to a signal of a single color. If a set of two or more conventional passively tagged probes or a set of two or more pairs of interacting hairpin probes target the same target sequence, each conventional passively tagged probe in the set or pair of interacting hairpin probes in the set targets a separate target-sequence region (or subsequence) of the target sequence. In multiplex methods for simultaneously detecting two or more target sequences in the one or multiple target molecules (or target strands), each target sequence is probed by either by one or more conventional passively tagged probes or by one or more pairs of interacting hairpin probes of this invention, where signal amplification leads to a signal of a different color for each target sequence.

"Passively tagged." As used in the specification and claims of this patent application to describe a hybridization probe that corresponds to probes from the prior art (Choi et al. (2014)), "passively tagged" means that an initiator sequence, whether an HCR initiator sequence or an RCA initiator sequence, is appended to at least one end of the target-sequence-complementary sequence. The initiator in such a probe is not sequestered in a structure that prevents its functioning as an initiator. To the contrary the initiator sequence of a passively tagged hybridization probe can initiate signal amplification whether the probe is bound to its specific target sequence or is bound to a non-specific site.

Interpreting the Drawings

In the Figures sequences that are complementary to one another are designated by the same letter, and one is indicated by a prime (') to distinguish between complementary sequences. Thus, in the Figures sequences a and a' are complementary to one another, as are sequences b and b', I5 and I5', and so on.

Fluorescence In Situ Hybridization (FISH)

Methods according to this invention are FISH methods. FISH (fluorescence in-situ hybridization) is a well-known method for detecting nucleic acid targets in cells. First cells are fixed, commonly with formaldehyde or paraformaldehyde, and permeabilized, commonly with ethanol or a detergent, to permit introduction of nucleic acid hybridization probes. This invention is not limited to a particular method for fixing and permeabilizing cells; any fixing and permeabilizing method that is compatible with in-situ probe hybridization and HCR or RCA amplification can be used. For example, Choi et al. (2014) teaches fixing embryos with 4% paraformaldehyde and permeabilizing with methanol (Choi et al. (2014) Supplementary Information at S1.1). Shah et al. (2016) Development 143: 2862-2868 teaches fixing mouse brain slices with 4% paraformaldehyde and permeabilizing by the technique known as "PACT clearing", which includes incubation in a solution of 8% SDS detergent in 1× phosphate buffered saline (PBS) (Shah et al. (2016), Supplementary Materials and Methods. Chen et al. (2016) Nature Methods 13:679-684 and Supplementary Materials, teaches fixing cultured cells with 10% formalin and permeabilizing the fixed cells by storing in 70% ethanol (Chen et al. (2016), Supplementary Methods). In our work reported in the Examples, we used 4% formaldehyde in 1×PBS for 10 minutes for fixation and 70% ethanol for 30 minutes for permeabilization.

In the simplest FISH method a fluorophore-labeled linear (or random coil) hybridization probe complementary to a selected target sequence, for example, a DNA probe, is then added, and unhybridized probe (by which is meant copies of the probe that are not hybridized) is washed away. Fluorescence is then detected. The simplest FISH method suffices only for detecting abundant target molecules. For detecting rare target molecules, particularly for detecting rare target molecules at the single-molecule level, a FISH method must include a way to increase fluorescence emanating from a single target molecule. One general way to do that is signal amplification. This invention relates FISH methods that include either of two signal-amplification methods: the hybridization chain reaction (HCR) and rolling circle amplification (RCA). Methods according to this invention utilize FISH for detection of RNA and DNA targets with a high level of sensitivity, with certain preferred embodiments being capable of single-molecule sensitivity, sometimes referred to as single-molecule FISH (sm-FISH). The discussion below focuses primarily on detection of RNA targets. Particular adjustments that are necessary for DNA detection are described separately.

Hybridization Chain Reaction (HCR)

Certain methods of this invention relate to and employ FISH that includes a signal amplification method known as HCR, the hybridization chain reaction, for detection of single nucleic acid molecules in fixed and permeabilized cells (single-molecule FISH, abbreviated sm-FISH). Detection with conventional HCR signal amplification employs one hybridization probe, or more often, a set of several hybridization probes, for a particular nucleic acid target sequence, for example, an RNA target sequence. Typically the hybridization probe or the multiple hybridization probes in a probe set are not fluorophore-labeled. Each hybridization probe has attached to it a 3' tail, a 5'tail, or both a 3' tail and a 5'tail, none of which hybridize to the target sequence. Instead, each tail comprises a terminal HCR "initiator" sequence. We refer to hybridization probes that, when bound to their target sequence, have a free (unsequestered) initiator sequence as "passively tagged probes." Detection of an RNA target sequence or a DNA target sequence with HCR also employs a pair of fluorophore-labeled hairpin oligonucleotides, sometimes referred to as HCR monomers, one of which interacts with the initiator sequence of the hybridization probe to start HCR amplification. The basics of existing HCR detection methods are shown in FIG. 1, which depicts such methods showing hybridization of a single probe to single nucleic acid target sequence, wherein the hybridization probe includes a single HCR initiator sequence. Cells, whether in culture or in a tissue slice, are fixed and permeabilized, as is customary in FISH methods. A hybridization probe complementary to a nucleic acid target sequence, for example an RNA target sequence, is added to the fixed and permeabilized cells and incubated to hybridize the probe to the target sequence. Before HCR monomers are added the sample is washed to remove unbound copies of the probe. As will be appreciated from the description that follows, such removal is critically necessary, because a copy of a probe is able to initiate HCR amplification whether specifically (correctly) hybridized or non-specifically bound. HCR is then performed by adding fluorophore-labeled HCR monomers and incubating. Unused HCR monomers are then removed by washing, after which fluorescence is detected, microscopically or by flow cytometry.

FIG. 1 depicts signal amplification by HCR initiated by a single passively tagged hybridization probe 11 that includes a probing sequence P1 that is complementary to target sequence TS1 in nucleic-acid target molecule 10. Hybridization probe 11 also includes, as a 5' tail initiator I1, which contains segments a' and b'. Initiator I1 is attached to probe sequence P1 by means of a spacer S1. Also shown in FIG. 1 is a pair of HCR hairpin oligonucleotides (HCR monomers), namely, fluorophore-labeled hairpin oligonucleotides H1 and H2. Monomer H1 comprises single-stranded 5' terminal sequence a, known as a "toehold" sequence, and a stem-and-loop hairpin comprising stem b-b' (comprising hybridized arm sequences b and b') and single-stranded loop sequence c'. Toehold sequence a is a single-stranded extension of stem arm b. In order the four sequences of H1 are 5'-a-b-c'-b'-3'. Hairpin monomer H1 is shown to contain only a single 3' terminal fluorophore O. Monomer H2 comprises single-stranded terminal toehold sequence c, and a stem-and-loop hairpin comprising stem b'-b (comprising hybridized arm sequences b' and b) and single-stranded loop sequence a'. In order the four sequences are 3'-c-b-a'-b'-5'. HCR monomer H2 also contains a single 5' terminal fluorophore O. The fluorophores O on H1 and H2 are the same. The monomers can also be labeled with multiple copies of fluorophore O.

FIG. 1 is a schematic flow chart of HCR amplification that is initiated by initiator sequence I1. First probe 11 is added to and incubated with a sample containing cells that have been a fixed and permeabilized. As shown at the top of FIG. 1, probe sequence (target-sequence-complementary sequence) P1 hybridizes to target sequence TS1, but spacer sequence S1 and initiator sequence I1 do not. Thus, initiator sequence I1, comprising sequences a', b', is bound (or tethered) to target sequence TS1 through probe sequence P1 but remains single-stranded. After removal of unbound copies of probe 11 by washing, the pair of HCR monomers H1 and H2, shown at the top-right of FIG. 1, is added to the washed sample containing target molecule 10 and hybridized probe 11.

Incubation of HCR monomers H1 and H2 with the sample containing hybridized probe 11 under hybridization conditions causes HCR signal amplification as follows. With reference to the second schematic in FIG. 1, sequence a' of initiator sequence I1 hybridizes to H1 toehold sequence a, forming a hybrid that is extended by strand displacement, whereby initiator sequence b' hybridizes to H1 sequence b, beginning HCR polymerization. This hybridization-and-strand displacement reaction, which is irreversible under hybridization conditions, separates stem b-b' of monomer H1 with the result that H1 sequences c', b' become a single-stranded 3' terminal region as shown and available to act as an initiator sequence I2 for monomer H2. Thus, H1 sequence c', now single-stranded, hybridizes to H2 toehold sequence c, forming a hybrid that is extended by strand displacement, continuing HCR polymerization, as shown in the third schematic in FIG. 1. This second hybridization-and-strand displacement reaction, also irreversible under hybridization conditions, separates stem b'-b of H2 with the result that H2 sequences a', b' become a single-stranded 5' terminal region identical to the original initiator sequence I1, at the end of the growing polymer chain, as shown in the third schematic in FIG. 1. Single-stranded sequences a', b' of H2 can then add another H1 monomer as shown in FIG. 1. This results in a growing double-stranded HCR polymer HCR-P, which, as shown in the bottom schematic in FIG. 1, has a series of monomers H1 in one strand and a series of H2 monomers extending from initiator sequence I1 in the complementary strand. Unincorporated H1 and H2 monomers are removed by washing, and fluorescence is detected by microscopy or flow cytometry. Passively tagged probes such as probe 11 are prone to generating false signals, because HCR operates equally well on specifically bound and nonspecifically bound probes.

If initiator sequence I2 is included in probe 11 as a 3' tag (3'-b'-c'-P1), it can also initiate HCR polymerization of the same HCR monomers H1 and H2. Sequence c' of initiator sequence I2 hybridizes to H2 toehold sequence c as described above to initiate polymerization in the manner described above to create a second HCR polymer that begins with H2 rather than H1 and extends from the 3' end of probe sequence P1. Also, a set of probes can be made by changing the target-sequence-complementary sequence of probe 11 to hybridize to additional sequences in target sequence TS1.

Sm-FISH with Rolling Circle Amplification (RCA)

Figure 2:
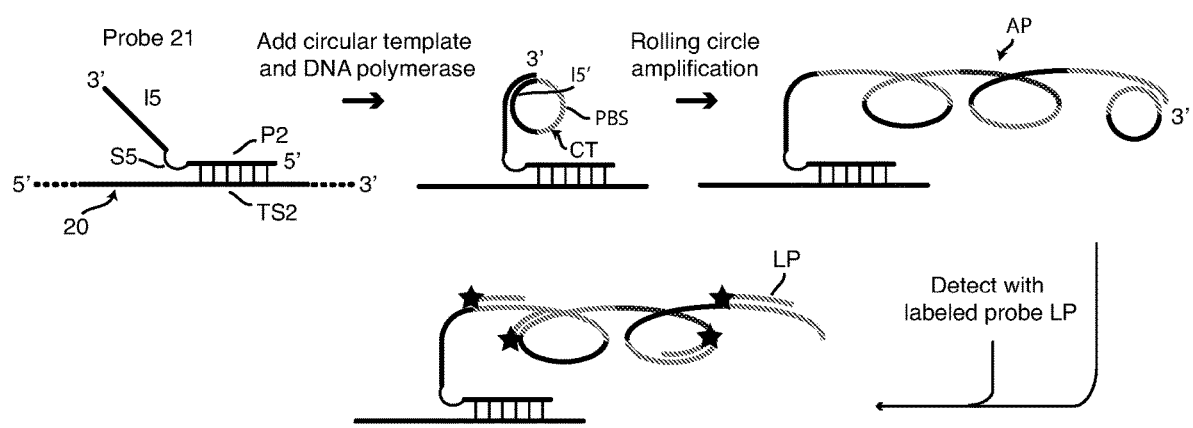
FIG. 2 is a schematic depiction of detection of a nucleic acid target sequence with a passively tagged hybridization probe and RCA signal amplification with a circular template and a labeled detection probe.

This invention also includes reagents and methods for, or capable of, sm-FISH detection that include signal amplification by rolling circle amplification (RCA). We describe first our conception of the manner in which RCA can be used with passively tagged hybridization probes is depicted in FIG. 2, which presents a schematic flow chart of hybridization, RCA amplification, and detection with a detector probe, shown here as fluorophore (O)-labeled detector probe LP. The first schematic on the left of FIG. 2 shows a probe 21 hybridized to a target strand 20, which contains target sequence TS2. Hybridization probe 21 contains target sequence-specific portion P2, spacer S5 and RCA initiator I5, a DNA sequence that remains single-stranded when probe sequence P2 binds to target sequence TS2. Initiator sequence I5 is a priming sequence with a free 3' terminus. Probe 21 is hybridized to targets in fixed and permeabilized cells, and excess unbound probe is removed by washing as described above for HCR methods.

Thereafter RCA is carried out on the sample utilizing a circular DNA template CT that contains sequence I5' that is complementary to the probe's initiator sequence I5, and also contains detector probe-binding sequence PBS. Template CT and a DNA polymerase are added to the washed sample, which is then incubated under RCA conditions. Initiator (primer) sequence I5 hybridizes to sequence I5' of template CT as shown in the second schematic in FIG. 2. Template CT is then copied multiple times in succession, that is, polymerized, by the DNA polymerase, as shown in the third schematic in FIG. 2. Since template CT is circular and endless, a very long single-stranded DNA amplification product AP is produced which contains many tandemly repeated copies of circular template CT, as shown. The circular template may be added preformed to the reaction or, it may be created in situ by using a linear version of CT, which is first bound to I5 and then turned into a circle by the addition of ligase. Amplification product AP remains tethered to target sequence TS2 via the hybridized probe 21. Unincorporated template CT is washed away, and detector probe LP is added and incubated with the sample under hybridizing conditions. As shown in the final schematic in FIG. 2, labeled probe LP, which has the sequence of segment PBS circular template CT, hybridizes to each copy of circular template CT in amplified product AP. Labeled probe LP includes at least one fluorophore O. In the embodiment depicted in FIG. 2 probe LP is a linear (random coil) probe labeled with a single fluorophore. Many copies of labeled probe LP bind, rendering target sequence TS2 intensely fluorescent. Excess unbound labeled probe LP is removed by washing, and fluorescence is detected by microscopy or flow cytometry. A molecular beacon probe can be used instead of the singly labeled probe LP to obviate the need for removal of the latter by washing. As with HCR, passively tagged probes for initiating RCA, such as probe 21, are prone to generating false signals, because RCA operates equally well on specifically bound and nonspecifically bound probes.

Methods and Reagents of this Invention with HCR

Detection methods of this invention are sm-FISH methods that include fixing and permeabilizing cells, as described above, hybridizing probes with a nucleic-acid target sequence in the cells, for example an mRNA sequence, and polymerizing a pair of HCR hairpin oligonucleotides (HCR monomers) as described above. Methods of this invention differ from previously known FISH method with HCR amplification in, inter alia, the design and construction of hybridization probes used to initiate HCR polymerization. Rather than using a hybridization probe passively tagged with an initiator sequence, which is capable of initiating HCR whether the probe is hybridized to a target sequence or bound to a non-specific site, methods of this invention use probes of this invention that initiate HCR signal amplification only when hybridized to the intended nucleic acid target sequence, for example, a selected target sequence in an mRNA target molecule. Hybridization probes of this invention comprise a pair of interacting stem-and-loop oligonucleotides that we refer to as a pair of interacting hairpin oligonucleotide probes, preferably composed of DNA, that hybridize adjacently on a nucleic acid target strand's target sequence, which may be a DNA strand or an RNA strand such as an mRNA strand, in a sample that has been fixed and permeabilized by fluorescence in-situ hybridization (FISH) methods.

a. A Pair of Interacting Hairpin Probes of this Invention and their Interaction

An embodiment of pair of interacting hairpin probes according to this invention and a schematic flow chart of their interaction are illustrated in FIG. 3A. The probe pair includes a first, "arm-donating hairpin probe," 31 that we sometimes call an "arm-donating beacon." Probe 31 is a stem-and-loop oligonucleotide having a stem e-e' and single-stranded loop sequence P3 that is complementary to target sequence TS3 of target nucleic acid molecule 30. One of the hybridizing arms of the stem, the "donating arm," includes a terminal, single-stranded extension f'. The probe pair also includes a second, "arm-acceptor hairpin probe" 32. Probe 32 is a stem-and-loop oligonucleotide having a stem f-f and single-stranded loop sequence g'. One of the arms of the stem includes a single-stranded extension comprising terminal target-complementary sequence P4 and, in the embodiment depicted, also toehold sequence e.

Sm-FISH methods according to this invention include steps to detect a target sequence in a sample of cells that include, or are suspected of including, target molecules containing the target sequence:
   a) fixing and permeabilizing cells in the sample;
   b) washing the fixed and permeabilized cells;
   c) incubating the sample containing the washed cells with at least one pair of interacting hairpin probes according to this invention;
   d) preferably but not mandatorily, washing the incubated cells to remove unhybridized probes;

e) after step c) or, if included, step d), adding polymerization reagents and incubating to produce an amplified product, said polymerization reagents comprising, for HCR signal amplification, at least one pair of fluorophore-labeled HCR monomers or, for RCA signal amplification, at least one circular DNA template and DNA polymerase;

f) washing away excess (unused) HCR hairpin oligonucleotide monomers or excess (unused) RCA circular template;

g) for RCA signal amplification, adding and incubating a fluorophore-labeled detector probe for each target sequence followed by removal of excess detector probes by washing; and h) detecting fluorescence in said cells by microscopy or by flow cytometry.

The interacting probe pair depicted in FIG. 3A functions as follows. When the sample containing fixed and permeabilized cells is incubated with probe pair 31, 32, as shown in the second schematic in FIG. 3A, the pair of probes first hybridize to the target sequence TS3 by their target-complementary sequences, here loop sequence P3 and extension sequence P4. Probes of an interacting probe pair according to this invention, here probes 31, 32, hybridize "adjacently", that is, sufficiently close to one another to enable their interaction as shown in FIG. 3A, middle schematic. By "adjacently" we mean that the target-complementary sequences (or "probe sequences") of an interacting probe pair according to this invention, here probe sequences P3 and P4, hybridize without any gap between them or with only a small gap between them that still allows their intended interaction, preferably a gap of not more than 4-5 nucleotides. Hybridization of loop sequence P3 causes stem e-e' of probe 31 to open, whereby donating arm e', f' becomes single-stranded. Hybridization of extension P4 does not cause stem f'-f of probe 32 to open. After binding to the target, as shown in the schematic on the middle of FIG. 3A, hybridized and open probe 31 interacts with hybridized probe 32. In the embodiment depicted in FIG. 3A, arm sequence e' of probe 31 hybridizes to toehold sequence e of hybridized probe 32, forming hybrid e'-e. By strand displacement, hybrid e'-e is extended, thereby opening stem f'-f of probe 32 and rendering the sequence comprising loop g' and arm f' into a 3'-terminal single-stranded sequence g', f', which together form HCR initiator sequence I3.

Shown in FIG. 3B is a pair of HCR hairpin oligonucleotides (HCR monomers), namely, fluorophore-labeled hairpin oligonucleotides H3 and H4. Monomer H3 comprises single-stranded 3' terminal sequence g, known as a "toehold" sequence, and a stem-and-loop hairpin comprising stem f-f' (comprising hybridized arm sequences f and f') and single-stranded loop sequence h'. Toehold sequence g is a single-stranded extension of stem arm f. In order the four sequences of H3 are 3'-g-f-h'-f'-5'. Monomer H4 comprises single-stranded terminal toehold sequence h, and a stem-and-loop hairpin comprising stem f'-f (comprising hybridized arm sequences f' and f) and single-stranded loop sequence g'. In order the four sequences are 5'-h-f-g'-f'-3'. HCR monomers H3 and H4 are labeled with the same fluorophore I. (That fluorophore is shown as an unfilled star to reflect the fact that, if monomer pair H1, H2 and monomer pair H3, H4 are used in the same reaction, as discussed below in connection with FIG. 4, the fluorophore on monomer pair H1, H2 is a different color than the fluorophore on monomer pair H3, H4.)

HCR signal amplification is performed following generation of initiator sequence I3 by the method described above. Following interaction of probes 31 and 32 to generate HCR initiator I3, unbound probes are washed away. Then HCR monomers H3 and H4 are added and incubated with the sample under hybridizing conditions. Sequence g' of freed initiator sequence I3 (FIG. 3A) hybridizes to toehold sequence g of HCR monomer H3, forming a hybrid that is extended by strand displacement, whereby I3 initiator sequence f' hybridizes to H3 sequence f, beginning HCR polymerization. This hybridization-and-strand displacement reaction, which is irreversible under hybridization conditions, separates stem f-f' of monomer H3 with the result that H3 sequences h', f' become a single-stranded 3' terminal region as shown and available to act as an initiator sequence I4 for monomer H4. Thus, H3 sequence h', now single-stranded, hybridizes to H4 toehold sequence h, forming a hybrid that is extended by strand displacement, continuing HCR polymerization, in the manner discussed above in connection with FIG. 1. This second hybridization-and-strand displacement reaction, also irreversible under hybridization conditions, separates stem f'-f of H4 with the result that H4 sequences g', f' become a single-stranded 3' terminal region identical to the original initiator sequence I3, at the end of the growing polymer chain, leading production of an HCR polymer like the one depicted in FIG. 1 except with monomer units H3 and H4. Unincorporated H3 and H4 monomers are removed by washing, and fluorescence is detected by microscopy or flow cytometry.

Interacting hairpin probes 31-32 generate HCR initiator sequence g', f' (I3) only if the pair hybridize adjacently on target sequence TS3. When free in solution or non-specifically bound, probe 31 is not open and donating arm e', f' does not exist in a single-stranded form and thus can't interact with probe 32, which retains its stem-loop structure. Therefore, initiator sequence g', f' (I3) is sequestered, that is, not available in a single-stranded form needed to initiate HCR polymerization. First probe 31 is like an unlabeled molecular beacon probe in structure and functioning, both of which are well known. See, for example, Tyagi et al. (1998) Nature Biotechnology 16: 49-53; and Bonnet et al. (1999) Proc. Natl. Acad. Sci. (USA) 96: 6171-6176. Probe 31 is very specific for the intended (correct) target sequence TS3. It can be designed to be either mismatch-tolerant, that is, to hybridize and open even if target sequence TS3 contains one or two mismatched nucleotides relative to loop P3; or it can be designed to be allele-discriminating, that is, to hybridize and open if loop P3 hybridizes to perfectly complementary target sequence TS3, but not to open if target sequence TS3 contains a single mismatched nucleotide relative to loop P3 or if non-specifically bound. Thus, with methods of this invention it is possible to initiate HCR signal amplification from only one of multiple closely related alleles in the target sequence (such as a target sequence containing a single-nucleotide polymorphism (SNP). Probe 32 will not open and generate single-stranded initiator sequence I3 unless hybridized adjacently to an open probe 31. Thus, even though probe 32 is not molecular-beacon type and consequently more apt to bind non-specifically via linear sequence P4, such as to hybridize to a mismatched sequence in target strand 30 or elsewhere in the cellular matrix, probe 32 will not open due to that fact—it must hybridize adjacently to an open probe 31 in order to be opened and generate single-stranded sequence I3. Thus, only if the first probe hybridizes correctly, and only if the second probe hybridizes adjacently to it, which means hybridize correctly, will a single-stranded HCR initiator sequence result. Copies of probe 32 that are in solution or bound non-specifically will not initiate HCR amplification of HCR monomers H3, H4 and will not, therefore, lead to generation of background. Accordingly, methods according to this invention have low background, even embodiments without a washing step between probes hybridization and HCR amplification. However, because a stem hybrid is dynamic and subject to "breathing", it is possible that very rarely a copy of probe 31 in solution could be open briefly and contact a copy of probe 32, leading to HCR amplification. To guard against that possibility, preferred embodiments of methods of this invention include a washing step prior to the addition of monomers H3, H4 as a precaution against developing even a low level of background signal.

In the design above, the probe sequence in arm-donating beacon 31 is bound by two arms of a hairpin, which, as discussed above, confers higher specificity on the probe. The probe sequence on arm-acceptor probe 32, on the other hand, is a terminal sequence. If the user wants to confer higher specificity on this probe as well, a hairpin forming arm sequence can be added towards the 5' of probe sequence P4. For example referring to probe 32 in FIG. 3, a sequence e' would be appended to the 5' end of the probe. With this addition, the free probe 32 would contain two hairpins, f', g, f and e, P4, e'. Upon binding to the target, the latter hairpin would unravel and render the toehold sequence e single stranded. The subsequent strand displacement and unmasking of the initiator would occur as described above. This modification would ensure further that the free probes do not interact with each other.

Figure 4:
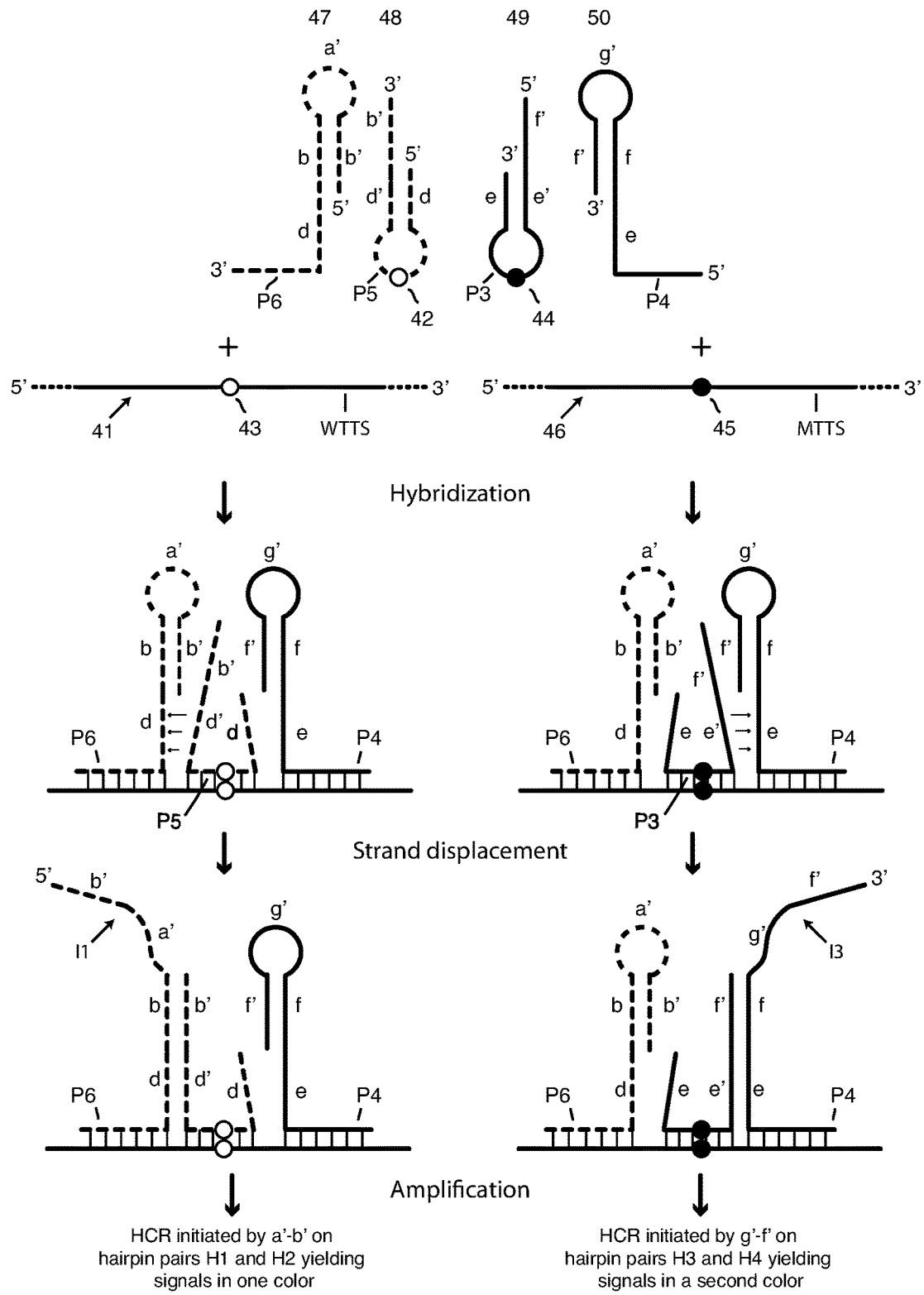
FIG. 4 is a schematic depiction of two pairs of interacting hairpin probes and their interaction with each other and with their target sequence to generate HCR initiator sequences. The arm-acceptor probes contain a toehold sequence, and the arm-donating probes contain a toehold-complement sequence.

In the Examples below, we demonstrate successful smFISH detection using for a given target sequence a single interacting probe pair that generates an HCR initiator sequence. A set of probe pairs can be made by changing the target-sequence-complementary sequences of both probes so that different pairs hybridize at different places on the target sequence, generate the same initiator, and initiate HCR polymerization with the same pair of HCR monomers to produce a more intense fluorescent signal.

b. Two Interacting Probe Pairs According to this Invention for Two Closely Related Alleles Certain embodiments of this invention comprise methods to detect, or detect and quantify, either or, if present, both of two closely related alleles, or target-sequence variants. The variation between alleles can include substitution, deletion, or insertion of one or more nucleotides. The variation can also include splice variants. Preferably the variation in the target sequence is contained within the binding region of the arm-donating probe, although, longer variations that span the binding regions of both the arm-donating probe and the arm-accepting probe can also be detected. Detection and quantification can provide single-molecule sensitivity and resolution. Detection of one or, if present, both of two closely related alleles utilizes two pairs of interacting hairpin probes and two pairs of differently labeled HCR monomers, one probe pair and one monomer pair for each allele, is shown schematically in FIG. 4. FIG. 4 presents two parallel flow charts, one for each probe pair.

Shown in FIG. 4 are two different nucleic acid target molecules, which are closely related allelic variants. Target molecule 41 contains a first target-sequence variant, which for purposes of explanation we refer to as wild-type target-sequence variant WTTS. Target molecule 46 contains a second target-sequence variant, which for purposes of explanation we refer to as mutant-type target-sequence variant MTTS. The target sequence variants are closely related alleles that differ by a single nucleotide substitution. Target-sequence variant WTTS has a wild-type nucleotide represented as open circle (○) 43, and target sequence MTTS has a substituted mutant nucleotide represented by filled circle (λ) 45. Target-sequence variants WTTS and MTTS, and target strands 41 and 46 are otherwise identical. A starting sample may contain either or both of strands 41 and 46.

Shown in the top schematic of FIG. 4 are two pairs of interacting probes as they exist free in solution: a pair that includes arm-donating hairpin probe 48 and arm-acceptor probe 47, and a pair that includes arm-donating hairpin probe 49 and arm-acceptor probe 50. For purposes of illustration the interacting probe pair on the left, 48 and 47, is drawn in broken lines, while the interacting probe pair on the right, 49 and 50, is drawn in continuous lines. Considering first the latter pair, probes 49 and 50 have the structure of probes 31 and 32 in FIG. 3A, respectively, and they are identically labeled in the two Figures. Their interaction when hybridized adjacently on target sequence MTTS (middle schematic on the right in FIG. 4) frees initiator sequence I3 (bottom schematic on the right in FIG. 4). Initiator I3 initiates HCR polymerization of HCR monomers H3 and H4 (FIG. 3B) as described above in connection with FIGS. 3A and 3B. HCR monomers H3 and H4 are singly labeled with the same fluorophore I. Loop P3 of probe 49 is perfectly complementary to target-sequence variant MTTS. It includes nucleotide 44 (filled-in circle λ), which is complementary to nucleotide 45 (filled-in circle λ) in target sequence MTTS of target strand 46 but mismatched to nucleotide 43 (open circle ○) in target sequence WTTS in strand 41. We sometimes refer to each of nucleotides 42 and 44 as an "interrogating nucleotide." Arm-donating probe 49 is allele-discriminating: it opens when hybridized to target sequence MTTS, but it does not hybridize and open of contacted with target sequence WTTS, or if it non-specifically bound.

Turning to probe pair 48 and 47, the arm-donating hairpin probe 48, is a stem-and-loop oligonucleotide that is allele-discriminating. Its target sequence-complementary loop P5 is perfectly complementary to target-sequence variant WTTS. It includes nucleotide 42 (open circle ○), which is complementary to nucleotide 43 (open circle ○) in target sequence WTTS of target strand 41 but mismatched to nucleotide 45 (filled-in circle λ) in target sequence 46. Probe 48 also includes stem d-d'. Stem arm d', the donating arm, includes terminal, single-stranded extension b'. Probe 47 is an "arm-acceptor hairpin" probe, that is, a stem-and-loop oligonucleotide having a stem b'-b and single-stranded loop sequence a'. One of the arms of the stem, here the 3' arm b, includes a single-stranded extension comprising target-complementary sequence (or region) P6 and, in the depicted embodiment, also toehold sequence d. The interaction of probes 47, 48 when hybridized adjacently on target sequence WTTS (middle schematic on the left in FIG. 4) frees initiator sequence I1 (bottom schematic on the left in FIG. 4). Initiator I1 initiates HCR polymerization of HCR monomers H1 and H2 as described above in connection with FIG. 1. HCR monomers H1 and H2 are singly labeled with the same fluorophore O, which has a color different from the color of fluorophore I used to label HCR monomers H3 and H4. Arm-donating probe 48 is allele-discriminating: it opens when hybridized to target sequence WTTS, but it does not hybridize and open of contacted with target sequence MTTS, or if it non-specifically bound.

It is important to note that the donating arm of each donating beacon probe is longer than its complementary arm. For example, 5' arm of probe 49 is longer than its 3' arm, because the 5' arm contains sequence element f' in addition to the stem element, sequence e'. If probe 49 binds successfully to target sequence MTTS, as shown in the right-middle schematic in FIG. 4, the sequence element e' (toehold complement) is free (not hybridized in the stem) and poised to bind to sequence element e (toehold) in probe 50, as shown in the right-middle schematic in FIG. 4, and then to displace the sequence element f' in probe 50, generating a single-stranded initiator I3, comprising sequences g' and f' (FIG. 4 right-bottom schematic). If probe 48 binds successfully to target WTTS, the sequence element d' (toehold complement) is free and poised to bind to the sequence element d (toehold) in probe 47, as shown in the left-middle schematic in FIG. 4, and then to displace the sequence element b' in probe 47, generating single-stranded initiator sequence I1, comprising sequences a' and b'.

To be capable of detecting either or both target-sequence variants WTTS and MTTS in a single assay, all four probes of the two interacting probe pairs are incubated simultaneously with a sample containing fixed and permeabilized cells in a hybridization reaction, but, as shown in middle schematics in FIG. 4, only three of the four probes bind to a given target-sequence variant, here either WTTS or MTTS. Both right acceptor probe 50 and left acceptor probe 47 always bind to both allelic target-sequence variants, but only one of the donating beacons binds between them. When the target sequence variant is wild-type (variable nucleotide depicted by open circle ○) probe 48 binds, and when the target sequence variant is mutant (variable nucleotide depicted by filled circle λ) probe 49 binds. If both target-sequence variants are present in the sample, probes 47, 49 and 50 bind to copies of target-sequence variant MTTS, and probes 47, 48 and 50 bind to copies of target-sequence variant WTTS. Arm-acceptor probes 47 and 50 bind to both target-sequence variants, if present in the sample, adjacently to the left and to the right of the single nucleotide variation region where arm-donating hairpin probe 48 binds and where arm-donating hairpin probe 49 binds.

Figure 3:
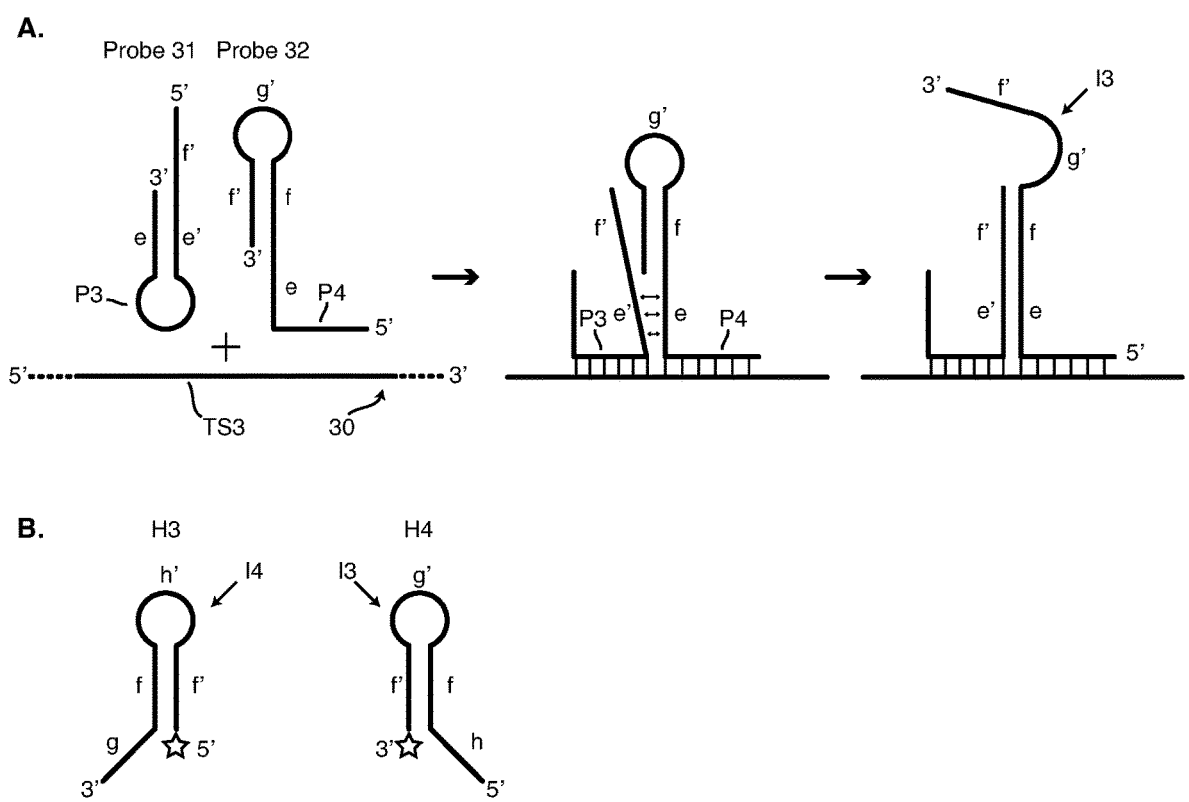
FIG. 3A is a schematic depiction of a pair of interacting hairpin probes and their interaction with each other and with their target sequence to generate an HCR initiator sequence.
FIG. 3B is a schematic depiction a pair of HCR monomers whose polymerization is initiated by the interacting hairpin probe pair shown in FIG. 3A.

Following incubation to permit hybridization and interaction between probes 49, 50 or probes 48, 47, or both, depending on which target sequence or sequences are present in the sample, unhybridized probes are removed by washing, and HCR monomers H3, H4, H1 and H2 are added, resulting in creation of one HCR polymer, or two. Following polymerization, unincorporated (excess) HCR monomers are removed by washing. The availability of single-stranded initiator sequence I1 (that is generated if wild-type target sequence WTTS is present) causes polymerization of HCR hairpin oligonucleotides H1 and H2 (FIG. 1). That amplification generates fluorescent signals in one color (for example, TMR). On the other hand, the availability of single-stranded initiator sequence I3 (that is generated if mutant target sequence MTTS is present), causes polymerization of HCR hairpin oligonucleotides H3 and H4 (FIG. 3). That amplification generates signals in a different, spectrally distinct color (for example, Cy5). Following HCR amplification, fluorescence from the two fluorophores is detected by microscopy or flow cytometry. In detection by microscopy, amplified fluorescent signal is detected as differently colored spots, whereby the presence of one or both alleles is indicated by the presence of differently colored spots, and the relative abundance of target strands with each allele is indicated by the ratio of spots of the two colors. Which donating beacon is designed for wild-type target-sequence variant is arbitrary, and nucleotides 42 and 44 can be reversed.

The binding of arm-donating probe 49 to target sequence MTTS does not cause the stem of adjacently hybridized arm-acceptor probe 47 to open, because the relevant sequences in the two probes are distinct rather than complementary (sequences d in probe 47 and e' in probe 49 are not complementary, and sequences b in probe 47 and f' in probe 49 are not complementary). Probe 48 cannot elicit any response from probe 50 for the same reason that probe 49 cannot elicit any response from probe 47.

Figure 5:
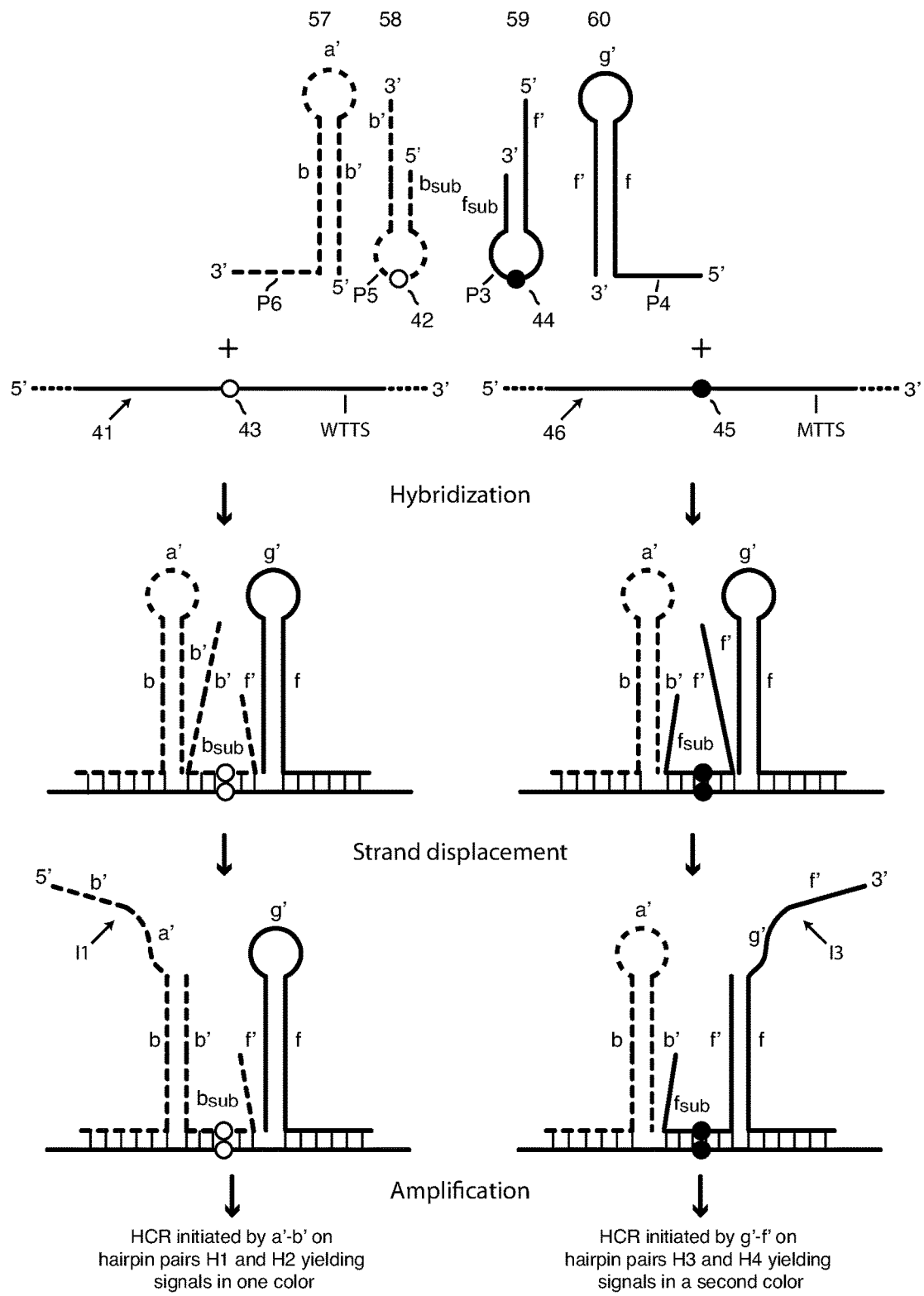
FIG. 5 is a schematic of the probe pairs of FIG. 4 modified to have no toehold or toehold-complement sequences, and their interaction with each other and with their target sequence to generate HCR initiator sequences.

FIG. 5 shows schematically the hybridization and interaction of the probes of FIG. 4 modified to eliminate the toehold sequence from arm-acceptor probes 47 and 50, and to eliminate the toehold-complement sequence from arm-donating probes 48 and 49. The target sequences are the same as depicted in FIG. 4. Arm-acceptor probe 60 (FIG. 5) includes single-stranded extension P4 rather than single-stranded extension e followed by P4 (FIG. 4). Toehold sequence e has been eliminated form probe 50 to create probe 60. The same is true for arm-acceptor probe 57, where the single-stranded extension is P6 rather than single-stranded extension d followed by P6 (FIG. 4). Toehold sequence d has been eliminated. Arm-donating probe 59 includes donating arm f' in place of donating arm e', f' of donating arm 49 (FIG. 4). Toehold-complementary sequence e' has been eliminated from probe 49 to create probe 59. The same is true for arm-donating probe 58, where the donating arm is b' rather than d', b' (FIG. 4). Toehold-complement sequence d' has been eliminated from probe 48 to create probe 58.

It will be seen that in probe 48 (FIG. 4) the stem-forming nucleotides are the nucleotides in sequences d and d', both of which are eliminated from probe 58 (FIG. 5). In the embodiment depicted in FIG. 5 the 5' stem arm of probe 58 (called $b_{sub}$) is derived from a portion of sequence b so that the stem can still form in probe 58. The same is true for arm-donating probe 59, where sequences e and e' has been eliminated. The 3' stem of probe 59 (called $f_{sub}$) is derived from a portion of sequence f so that the stem can still form in probe 59.

Figure 6:
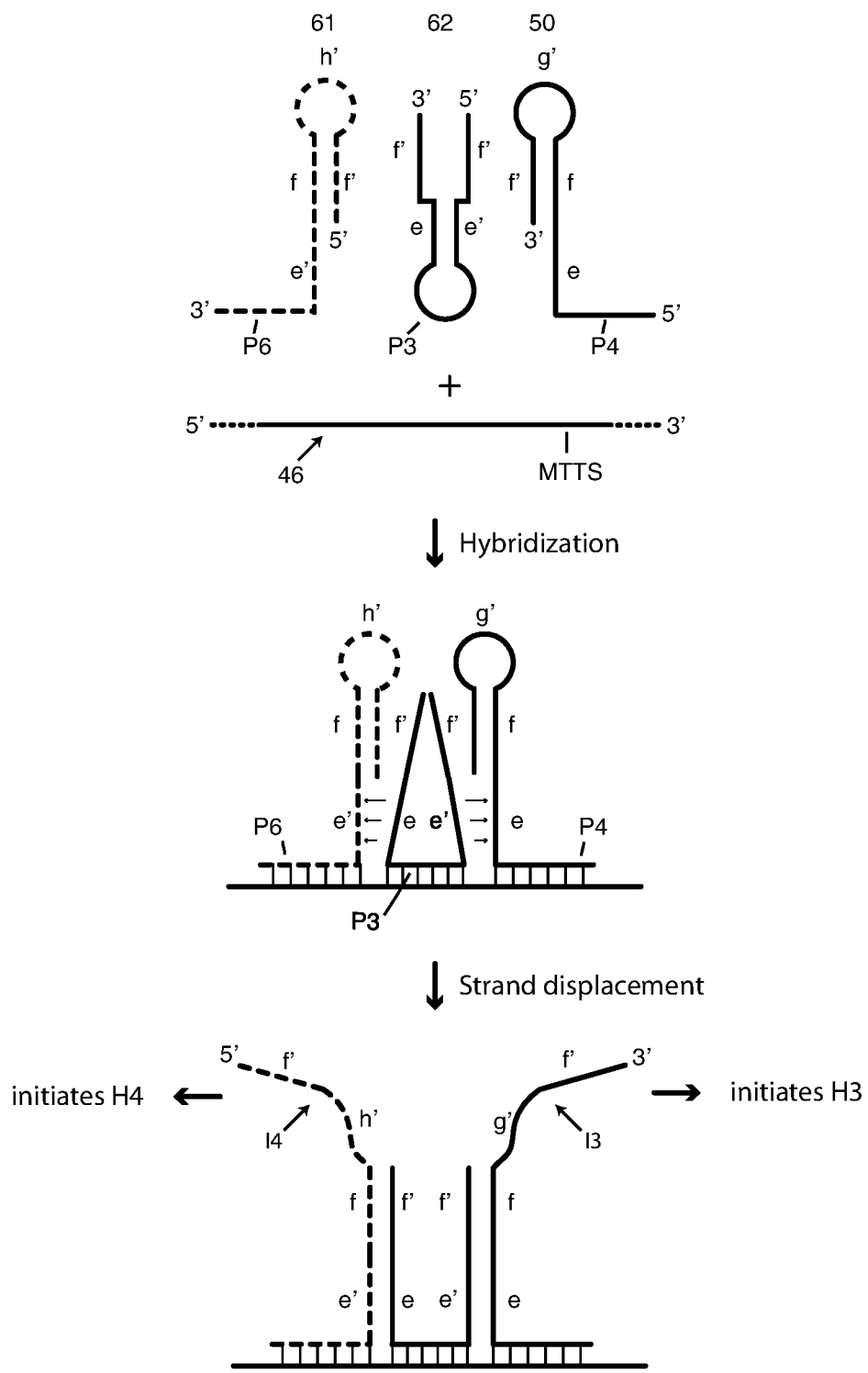
FIG. 6 is a schematic depiction of two pairs of interacting hairpin probes that share a common arm-donating probe and their interaction to generate two HCR initiator sequences.

The method of using the interacting probe pairs in FIG. 5 to generate HCR initiator sequences is the same as the method described above for the interacting probe pairs in FIG. 4, and the initiator sequences that are generated are also the same. When arm-donating probe 59 hybridizes to target sequence MTTS, as shown in the middle-right schematic in FIG. 5, its freed donating arm (sequence f') is the same length as stem arm f in probe 60; there is no toehold sequence. We have discovered that, nonetheless, probe 59 interacts with probe 60, freeing initiator I3, as shown in the bottom-right schematic in FIG. 5. Similarly, when arm-donating probe 58 hybridizes to target sequence WTTS, as shown in the middle-left schematic in FIG. 5, its freed donating arm (sequence b') is the same length as stem arm b in probe 57; there is no toehold sequence. Nonetheless probe 58 interacts with probe 57, freeing initiator I1, as shown in the bottom-left schematic in FIG. 5. The fact that a toehold-complement sequence in the donating arm of an arm-donating hairpin probe serves dual functions, to maintain the hairpin configuration when the probe is free in solution and to interact with the arm-acceptor probe upon binding to the target, nonetheless permits probe designs with very short or, as depicted in FIG. 5, 0-nt toehold-complement segments. Designs of the interacting hairpin probe pairs without any toehold sequences are described in the Examples. The fact that interacting hairpin probes without any toehold sequence function well, is surprising and is an aspect of this invention.

c. An Arm-Donating Beacon Probe that Reveals Two Masked Initiator Sequences and Generates HCR Signal from a Single Pair of HCR Monomers In order to increase the signals with interacting hairpin probe system, it is advantageous to utilize a set of probes that unmask two HCR initiator sequences, rather than one, for each target sequence. The two initiator sequences will initiate amplification from the same HCR monomer pair and thus produce signals of the same color. An example of such a system is presented in FIG. 6. This system includes two interacting probe pairs (62, 61 and 62, 50) comprising three probes, 61, 62, and 50 (FIG. 6, top). The two probe pairs share the same arm-donating probe 62. The three probes contain target-complementary sequences P6, P3 and P4, which hybridize to target sequence MTTS of target molecule 46. It will be appreciated that in this embodiment the target sequence may be a mutant sequence but it need not be. The three probes hybridize adjacently on the target sequence, as shown in the middle schematic in FIG. 6. They are designed to initiate HCR amplification from monomers H3 and H4 (FIG. 3B). Arm-donating beacon 62 forms an intramolecular stem through the binding of sequence elements e and e' that are present on either side of target sequence-complementary loop P3 when the probe is free in solution. This probe also contains two copies of the sequence element f' as single-stranded extensions of stem elements e and e'. While e and e' in probe 62 bind to each other, two copies of the f' sequence do not bind or interact with each other and remain single stranded. Different from other arm-donating beacon probes depicted in the Figures, arm-donating beacon 62 can donate both of its arms to the acceptor hairpin probes that are situated on each of its two sides. Described earlier in relation to FIG. 4, arm-acceptor probe 50 contains (3' to 5') sequence elements f', g', f followed by target-complement sequence P4. Arm-acceptor hairpin 61 contains (3' to 5') target-complement P6, sequence elements e', f, h' and f". Hybridization of the three probes leads to disruption of hairpin stem e-e' in arm-donating beacon 62 and simultaneously creates a possibility both of binding open stem arm e of probe 62 with toehold sequence e' in arm-acceptor hairpin 61 and of binding open stem arm e' of probe 62 with toehold e in arm-acceptor hairpin 50 (FIG. 6, middle). These bindings lead to strand displacement in both arm-acceptor probes. Strand displacement in arm-acceptor probe 50 renders HCR initiator sequence I3 (loop g' and arm f') single-stranded. Strand displacement in arm-acceptor probe 61 renders HCR initiator sequence I4 (loop h' and arm f') single-stranded (FIG. 6, bottom). Freed initiator sequence I3 can initiate HCR amplification of monomers H3 and H4 starting with HCR monomer H3, and freed initiator sequence I4 can initiate HCR amplification of monomers H3 and H4 starting with HCR monomer H4. Both amplification reactions lead to basically the same polymerization product and generate the same color signal. This is in contrast with the system of probes described in FIG. 4 where the adjacent binding of three probes generates an amplified signal in one of the two alternative colors.

A Pair of Interacting Hairpin Probes for Initiation of RCA

Figure 7:
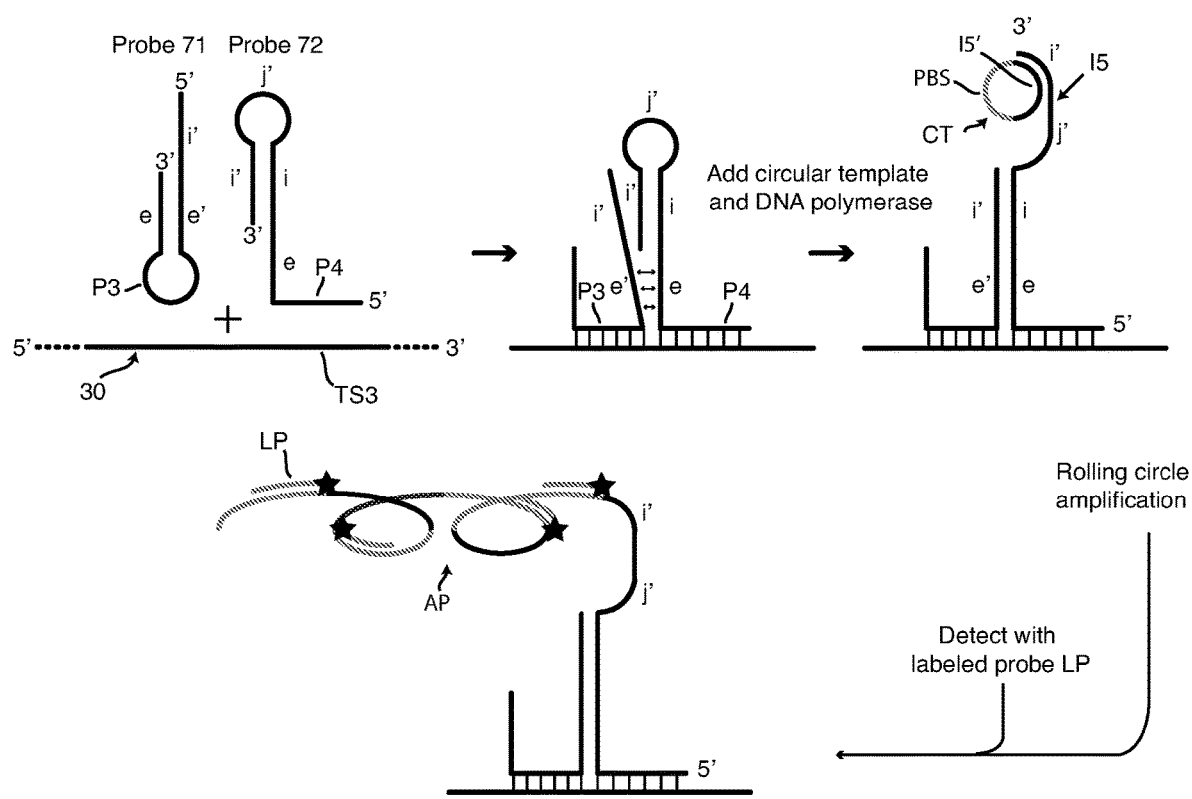
FIG. 7 is a schematic depiction of detection of a nucleic acid target sequence with a pair of interacting hairpin hybridization probes and RCA signal amplification with a circular template and a labeled detection probe.

To overcome the tendency of passively tagged hybridization probes (FIG. 2) to generate false signals in RCA, interacting hairpin probe pairs of this invention can be deployed in a manner similar to that described above for HCR. An RCA method according to this invention is depicted in FIG. 7, which presents a schematic flow chart of an RCA embodiment. For ease of understanding, elements of interacting hairpin probes 71, 72 that are common to elements of probes 31, 32 (FIG. 3) are given the same designations as in FIG. 3. Other elements in FIG. 7 are common to elements in FIG. 2 and are given the same designations as in FIG. 2.

Shown in the first schematic in FIG. 7 are target molecule 30 that contains target sequence TS3, and interacting hairpin probe pair 71, 72. Arm-acceptor probe 72 is the same as arm-acceptor probe 32 (FIG. 3), except that HCR initiator I3, comprising loop g' and stem arm f', is replaced with RCA initiator (primer) I5 (FIG. 2), comprising loop j' and stem arm i' (which makes the hairpin stem i-i'). Arm-donating probe 71 is the same as arm-donating probe 31 (FIG. 3), except that single-stranded extension f' of the donating arm is replaced by single-stranded extension i'. Probe hybridization and interaction proceeds as described above in connection with FIG. 3. However, interaction of probe pair 71, 72 frees single-stranded RCA initiator sequence I5, comprising loop sequence j' and arm sequence i'. Initiator I5 is the same initiator whose functioning is described above in connection with FIG. 2. I5 is a priming sequence for circular template CT. Copying CT by a DNA polymerase to generate polymer AP, hybridization of fluorophore (O)-labeled detector probe LP, and fluorescence detection proceed as described for FIG. 2. Briefly stated, whereas in the system depicted in FIG. 3 interacting hairpin probe 32 contains initiator sequence I3 that, when freed, initiates polymerization by hybridization, in the system depicted in FIG. 7 interacting hairpin probe 72 contains initiator sequence I5 that, when freed, is a priming sequence that initiates polymerization by RCA.

We note that sequence i' is present in both probes 71 and 72. Sequence i' in probe 71 can never serve as a primer, because it's 3' end is not free (it is connected to sequence e'). Sequence i' in probe 72 becomes available for binding to the circular template CT only upon interaction of the two interacting hairpin probes when hybridized to their intended adjacent sites on the target sequence. Only interaction of the target-bound probes can initiate RCA, as free or nonspecifically bound copies of probe 72 remaining when DNA polymerase is added will extend their 3' ends on themselves (see probe 72 structure), further decreasing the probability of generating false signals. Thus, although our preferred method includes a washing step to remove unbound interacting probes prior to addition of amplification reagents, such a washing step can be eliminated. RCA product AP is detected as described above in connection with FIG. 2. In order to amplify signals further, multiple pairs of interacting hairpin probes can be employed for a single target sequence, all generating the same initiator sequence, where each pair will generate an RCA signal from the same circular template. Furthermore, in order to perform multiplex detection and RCA signal amplification of different targets, one can use for each target a different interacting hairpin probe pair that generates a different initiator sequence for a different circularized target and a different detector probe labeled with a different color.

Design and Construction of Interacting Hairpin Probes

Some aspects of the lengths and sequences of various elements in the hairpin probes of this invention are relatively flexible, whereas the other aspects are relatively constrained.

The loop sequence of an arm-donating probe is designed to be complementary to the intended target sequence (which in some embodiments includes multiple allelic variations and in other embodiments excludes all but one variation) but not to other non-target sequences that may be present in a sample. The loop is designed to be sufficiently long to ensure the required uniqueness. The donating arm must include a number of nucleotides sufficient to maintain its hairpin configuration when free in solution or bound non-specifically. Further, whether mismatch-tolerant or allele-specific, its stem must open (dissociate) when the loop binds to its intended target sequence but not if it binds non-specifically. This is the well-known molecular beacon probe construction that is within the skill in the art. When the arm-donating probe's hairpin is to be allele-discriminating, the length of its loop is constrained by the need to reject allelic variations, particularly a single-nucleotide variation (SNV), so it is usually in the range of 10 to 25 nucleotides long. In the Examples below, the loop length/stem length combinations were, in nucleotides, 15/6, 12/6, 11/6, 9/6 (unsatisfactory), and 20/11 for HCR. Example 6 describes a combination of 25/5 for RCA. The donating arm of an arm-donating probe must interact with one stem arm of the arm-acceptor probe to form a hybrid that is stronger than the stem of the arm-donating probe, so that the donating arm will interact relatively irreversibly. The donating arm includes a single-stranded extension of several nucleotides to accomplish that requirement. In the Examples below the lengths of donating-arm extensions were, in nucleotides, 12, 17, and 18.

For embodiments that include HCR signal amplification, the lengths and sequences of the loop and the stem of an arm-acceptor probe are dictated by the choice of HCR monomers, as, when freed by interaction of the probes, the loop and one stem arm comprise an HCR initiator sequence. Analogously, for embodiments that include RCA signal amplification, the lengths and sequences of the loop and the stem of an arm-acceptor probe are dictated by the choice of the circular template. An arm-acceptor probe must maintain its hairpin configuration when free in solution, and it must not open when the probe hybridizes, either correctly to its target sequence or non-specifically. As compared to an arm-donating probe, its loop is generally shorter, and its stem is generally longer. In the Examples below, the loop length/stem length combinations of arm-acceptor probes were, in nucleotides, 8/18 for HCR. Example 6 describes a combination of 6/20 for RCA. One arm of the hairpin of an arm-acceptor probe has, in addition to stem-forming nucleotides, a single-stranded extension that includes a target-complementary sequence and, in certain embodiments, also a toehold sequence that is complementary to the stem-forming sequence of the donating arm of the arm-donating probe. The length of target-complementary segment can vary a great deal, for example from 15 to 50 nucleotides. In the Examples below, the target-complementary segments of the arm-acceptor probes were, in nucleotides, 19, 20, 22 or 24 for HCR. Example 6 describes a length of 22 nucleotides for RCA.

The length of the toehold sequence (and its complement in the arm-donating probe) has a significant impact on the specificity of allele discrimination: the shorter the toehold sequence, the more discriminatory the probes are. Arm-acceptor probes with toehold sequences 3 to 11 nucleotides long function well as general target detection probes. However, in allele-discriminating embodiments, better allele discrimination is achieved with smaller toehold sequences, with, as we have discovered, the best allele discrimination being exhibited by a toehold sequence of 0 nucleotides. In the Examples below, the lengths of the single-stranded extensions were, in nucleotides, 0-nt toehold plus 19, 20 or 22 target-complementary nucleotides; 5-nt toehold/plus 22 target-complementary nucleotides; and 14-nt toehold plus 24 target-complementary nucleotides for HCR initiation. Described for RCA initiation is an arm-acceptor probe whose single-stranded extension includes 22 target-complementary nucleotides and additionally a toehold sequence 5-nt long.

When there is a toehold sequence, the stem-portion of the arm-donating probe is complementary to the arm-acceptor probe's toehold sequence. In the first probe pair described in Example 3, the toehold sequence in the arm-acceptor probe was 5-nt long but the stem of the arm-donating probe was 6-nt long. To accommodate that difference, the single-stranded extension was reduced from 18 nucleotides (fully complementary to the 18-nt long stem arm of the arm-acceptor probe) to 17 nucleotides, with the terminal nucleotide of arm-donating probe's stem contributing the $18^{th}$ nucleotide. So stem-forming sequence of the 5' arm is complementary to the toehold sequence, as required, but it is one nucleotide longer, and the single-stranded extension is complementary to, but one nucleotide shorter than, its complement in the arm-acceptor probe. When there is no toehold sequence, the donating arm of the beacon probe, comprising stem-forming nucleotides and a single-stranded extension, is the same length as the stem of the arm-acceptor probe.

One part of each probe in a pair of interacting hairpin probes is specific to a target sequence and the other part of each probe is generic and can be used with different probe pairs for many different target sequences. With reference to FIG. 3, for example, in arm-acceptor probe 32 the hairpin stem-and-loop and the toehold sequences (f'-g'-f-e) are generic portions. Only target-complementary sequence P4 is target-specific. Similarly, in arm-donating probe 31 only loop P3 is target-specific. In the embodiments described above the generic portions of the probes are parts of a continuous single stranded nucleic acid molecule such as a DNA molecule. An aspect of this invention is that the generic portion and the target-specific portion of an interacting hairpin probe can be linked to each other through a non-phoshodiester bond and the probe still function well in the generation of amplified signals from HCR or RCA in target-dependent manner. For example, the generic portion of a probe can be linked to the target-specific portion via click chemistry (Baskin J M, et al. (2007) Proc. Natl. Acad. Sci. USA 104(43):16793-16797). Other methods of linking the two components will be apparent to persons skilled in the art. The linking of generic portions in this manner to target-specific portions enables substantial cost savings in probe synthesis, because the relatively long generic portions do not have to be synthesized repeatedly, and only the relatively short target-specific portions need to be synthesized for each different target sequence.

Special adjustments in hybridization procedures are needed for the detection of DNA targets with the probes of this invention. Because cellular DNA is double stranded, it is not readily accessible to probes for hybridization. To make such DNA target sequences accessible, fixed and permeabilized cells are subjected to a heat treatment in the presence of a denaturant (Vargas et al (2005) Proc. Natl. Acad. Sci. USA 102: 17008-17013). For example, incubating cells in presence of 2×SSC and 70% formamide at 80° C. for 10 minutes denatures genomic DNA sufficiently to permit subsequent hybridization with oligonucleotide probes, including interacting probe pairs of this invention, under normal conditions. In addition, so that any RNA species that is transcribed from the DNA target and is present in the cell will not obscure fluorescent signals from the DNA target, the cellular RNAs can be removed before interacting hairpin probes are added by a prior treatment with ribonuclease A. Typically a non-repeated nuclear DNA target sequence will be present only in two copies (one on each chromosome) in a given cell nucleus. Therefore, only two spots are generated by each set of interacting hairpin probes, and they are located within the nucleus. An additional consideration for the detection of DNA targets is that since DNA/DNA hybrids are slightly less stable than RNA/DNA hybrids formed between an interacting DNA hairpin probe pair and an RNA target sequence, the target-complementary segments of a probe pair are generally relatively longer if the target sequence is DNA.

Explanation of the Examples

Figure 8:
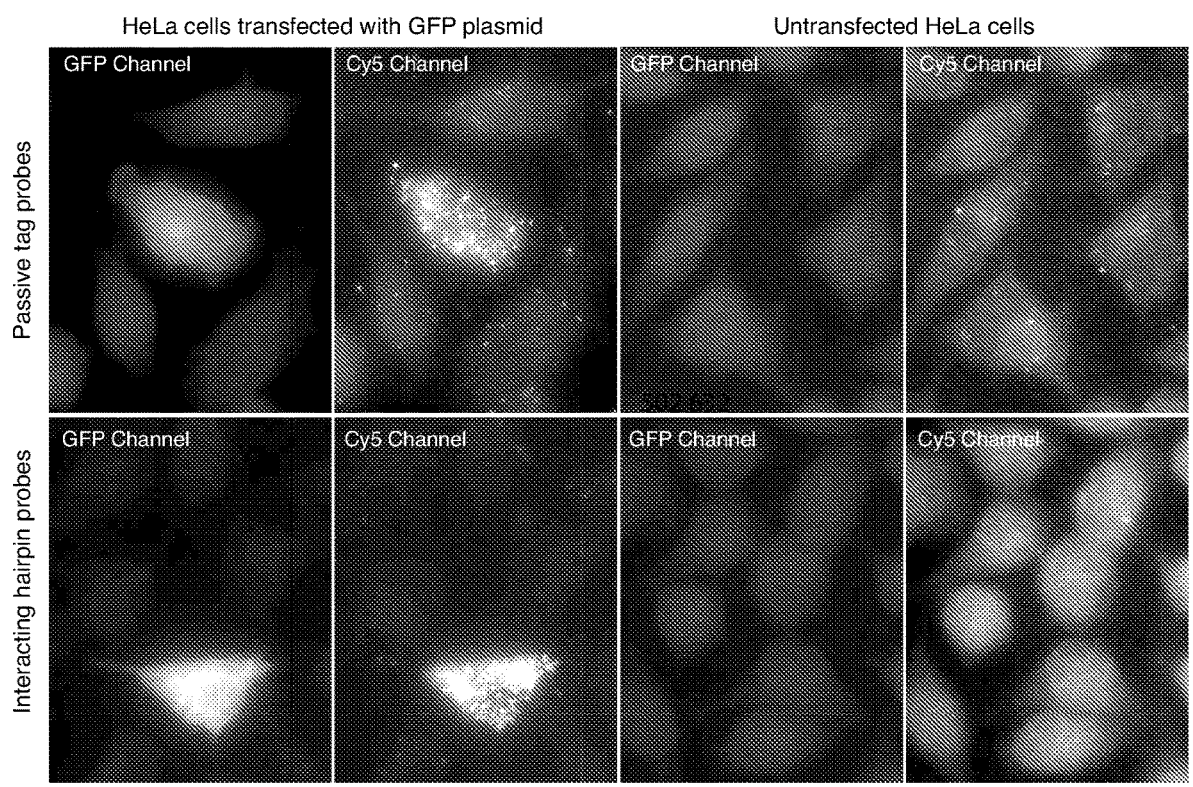
FIG. 8 is a set of microscopic images showing target-specific signals and backgrounds signals resulting from detection with a passively tagged hybridization probe and HCR signal amplification and from detection with an interacting probe pair and HCR signal amplification.

Example 1 compares the level of target sequence-specific signal and the level of background signal obtained when detection of an RNA target sequence and HCR amplification in fixed, permeabilized cells was initiated with a single pair of interacting DNA hairpin probes according to this invention or obtained when HCR was initiated with a single passively tagged DNA hybridization probe of the type shown in FIG. 1. The hairpin probe pair's construction is shown generally as probes 31 and 32 in FIG. 3, except that there is no toehold sequence as in probes 59 and 69 shown in FIG. 5. We performed several analyses. In a first analysis, we microscopically imaged cells transfected to express GFP, including a GFP target sequence for the hybridization probes, and we also imaged untransfected cells that were subjected to the same probes and HCR amplification. Representative images are presented in FIG. 8. Fluorescent spots appearing in the Cy5 channel were from Cy5-tagged HCR polymers. The spots within cell boundaries were counted using a previously described algorithm (Raj et al (2008) Nature Methods 5:877-879). The left four panels in FIG. 8 are for HeLa cells transfected with the GFP template and the right four panels are for HeLa cells not transfected with this template. One cell in each of the two leftmost panels exhibited florescence in the GFP channel, indicating that those two cells were transfected with the template plasmid (transfection occurs in some of the cells and does not occur in others). When the same set of cells are viewed in the Cy5 channel (second column of panels from the left) the HCR signals are visible. In the lower panel, which corresponds to detection and signal amplification with the pair of interacting hairpin probes, the Cy5 signals are visible only in the transfected cell. In the upper panel, which corresponds to detection and signal amplification with the passively tagged probe, the transfected cell exhibits strong signals as occurred in the previous case. However, unlike in the previous case, a few spots are visible in cells that do not exhibit any GFP fluorescence (not transfected). These signals potentially represent background, or false positive signals. To be entirely sure to consider only untransfected cells for the analysis of background, we also imaged HeLa cells that were not transfected with the GFP template. When these cells were viewed in the fluorescein channel only faint autofluorescence is observed in all cells (third column of panels from the left). However, when these cells were viewed in the Cy5 channel (right-most panels), any spot would be from non-specific sources. The image in the lower right panel is presented at higher contrast in order to reveal one spot in the entire field. While the lower panel shows just one spot in one of the eight cells that are visible, in the upper panel about 13 spots are visible in a total of only 5 cells. These observations indicate that, although the magnitudes of target-specific signals in the different probe systems are about the same, the magnitude of the background signals is higher when HCR in initiated by the passively tagged probe than when HCR is initiated by the pair of interactive hairpin probes.

We also analyzed the average number of spots in the cells of each of the four categories (transfected cells/passively tagged probe; transfected cells/interacting hairpin probe pair; untransfected cells/passively tagged probe; and untransfected cells/interacting hairpin probe pair) by computational image analysis (Raj et al (2008)). We found that on average HeLa cells expressing GFP yielded more than 100 spots/cell with both kinds of probes (the average number of spots could not be determined more precisely, because in many cells the spots were so numerous that they merged with each other, and thus the algorithm could not resolve them from one other). On the other hand, in control cells that did not express GFP the passively tagged probe yielded 1.46 spots per/cell, whereas, the interacting hairpin probe pair yielded 0.62 spots per cell. Just as in the representative images in FIG. 8, this analysis also indicates that, while the specific signals obtained with the two kinds of probes are about the same, the background signal generated by passively tagged probe is higher than the background signals generated by the interacting hairpin probes.

Figure 9:
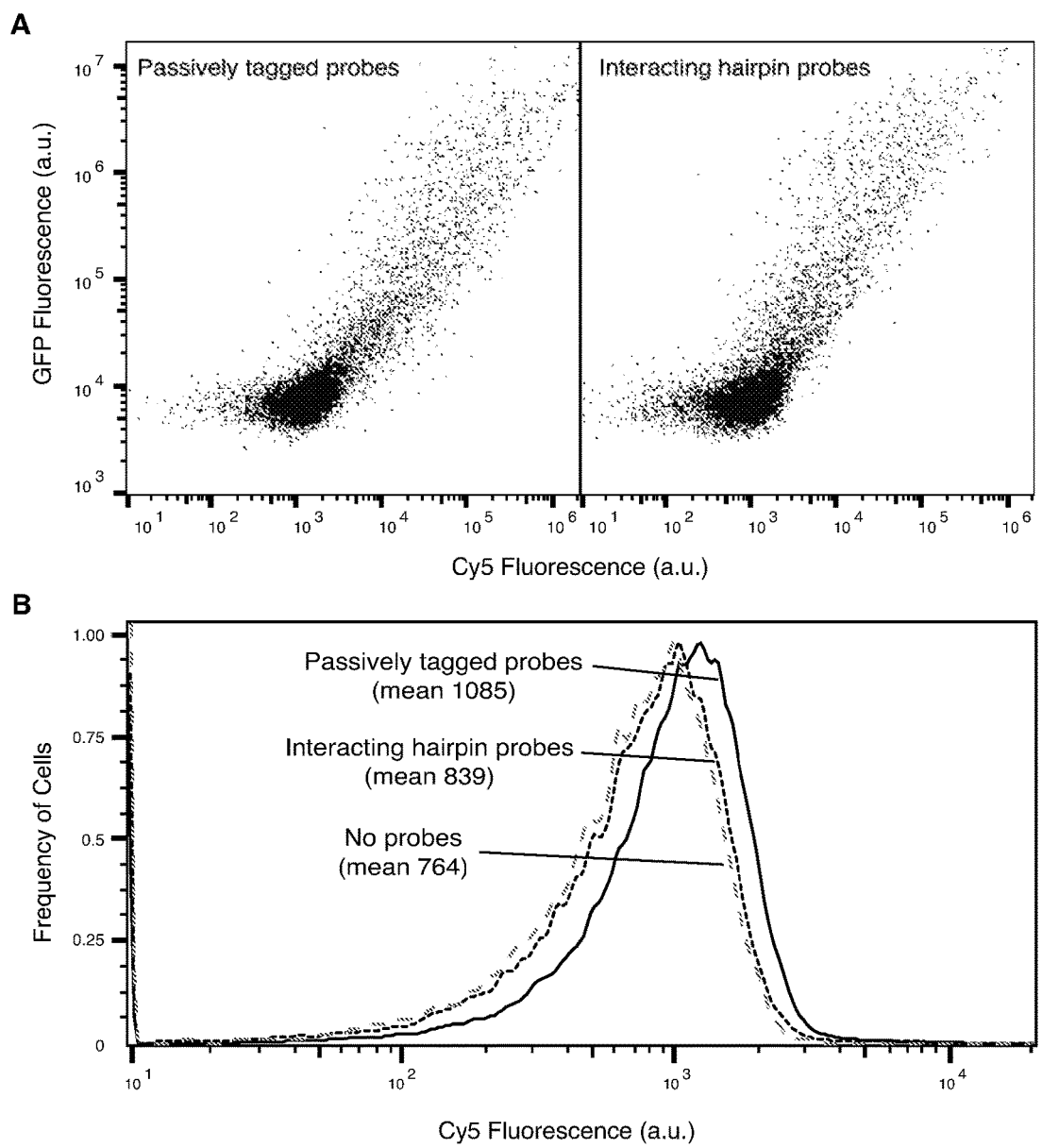
FIGS. 9A and 9B are graphs comparing target-specific signals and backgrounds signals generated in HCR using passively tagged probes and interacting hairpin probe pairs. The analysis was performed by flow cytometry.

To shed additional light on the background and on the specific signals generated by the two probe systems, we analyzed cells by flow cytometry from parallel hybridization-and-amplification reactions performed on cell suspensions. This analysis is presented in FIG. 9. In the scatter diagrams presented in the two panels of FIG. 9A, each dot represents the X-Y coordinates of the fluorescence of a single cell in the Cy5 channel and in the GFP channel, respectively. The large cluster of spots in the middle (at the intersection of $10^4$ units of GFP fluorescence and $10^3$ units of Cy5 fluorescence) represent the HeLa cells that were not transfected with the GFP plasmid and therefore did not exhibit significant levels of GFP or Cy5 fluorescence. The spots lying on the diagonal represent the transfected cells, which exhibit fluorescence in both the channels. The slope of an imaginary line representing the two distributions was about the same, indicating that the sensitivity of the two probe systems is similar. We also analyzed the Cy5 fluorescence in the cells that were not transfected. Because these cells do not exhibit significant levels of GFP fluorescence, only the Cy5 fluorescence is shown and the data is presented as continuous line histograms (FIG. 9B). In addition to the HeLa cells used with the two kinds of probes, we prepared a third category of HeLa cells that were not exposed to any probes. These histograms and the associated mean Cy5 fluorescence levels indicate, that, while the background level of fluorescence with the interacting hairpin probes is about the same as the cells that were not exposed to any probes, the background level of fluorescence with the passively tagged probes is significantly higher.

Both image-based and flow-cytometry-based analyses indicate that interactive hairpin probe pairs generate less background signal then do passively tagged probes. On the other hand, the levels of specific signals are about the same in both kinds of probes. Relatively high levels of background signals with passively tagged probes are consistent with the observations of the other laboratories discussed above.

FIG. 9B provides a quantitative comparison of background signals that are obtained with HeLa cell not exposed to any probes (mean 764 units), one passively tagged probe (mean 1085), or one pair of interacting hairpin probes (mean 839). The difference between fluorescence of cells with probes and without probes indicates the increase in the background signal that is created by each kind of probe. In the case of the passively tagged probe the difference was 301 units (1085-764), whereas in the case of interactive hairpin probes it was 75 units (839-764). In this comparison a single passively tagged probe or a single pair of interacting hairpin probe pair was used. However, as the number of probes binding to the target is increased by tiling them over the target to increase signal strength, the background signal increases substantially in the case of passively tagged probes but not very much in the case of interacting hairpin probes.

Example 2, part A describes experiments for either of two target-sequence variants that differ by a single nucleotide change using the type of system depicted schematically in FIG. 5 and described above with reference to that system. In this set of four probes, two arm-donating hairpin probes compete for whichever single target-sequence variant is present in the sample. The design of the interacting probe pairs was as follows: a first arm-donating hairpin probe (RDB6.6C) binds to the G target-sequence variant, if present, and then interacts with its arm-acceptor probe (RA6.3), which results in signal generation from HCR amplification of Cy5-labeled hairpin oligonucleotides H3 and H4, yielding a Cy5 signal; or a second arm-donating hairpin probe (LDB6.1T) binds to the A target-sequence variant, if present, and then interacts with its arm-acceptor probe (LA6.1), which results in signal generation from TMR-labeled HCR hairpin oligonucleotides H1 and H2, yielding a TMR signal. Fluorescent images from the two samples are presented in FIG. 10A. The two panels on the left show the same field of cells expressing the G variant as viewed in the Cy5 channel (top) and TMR channel (bottom). Similarly, the two panels on the right show the same field of cells expressing the A variant as viewed in the Cy5 channel (top) and TMR channel (bottom). After analysis of a number of such images, it was found that even though the same probe mixture was used to probe each of the two target-sequence variants, on average, the G variant yielded large number of Cy5 spots (86.7%) and very few TMR spots (13.3%), whereas, the A variant yielded large number of TMR spots (93.8%) and very few Cy5 spots (6.2%). (This data is also presented in the fifth row of FIG. 10B.) We also reversed the colors by making the first arm-donating hairpin probe complementary to the A target-sequence variant and the second arm-donating hairpin probe complementary to the G target sequence variant. The colors of dominant spots did indeed reverse, indicating that the right and left arm-acceptor hairpin probes and their cognate HCR pairs function in an equivalent and interchangeable manner.

Figure 10:
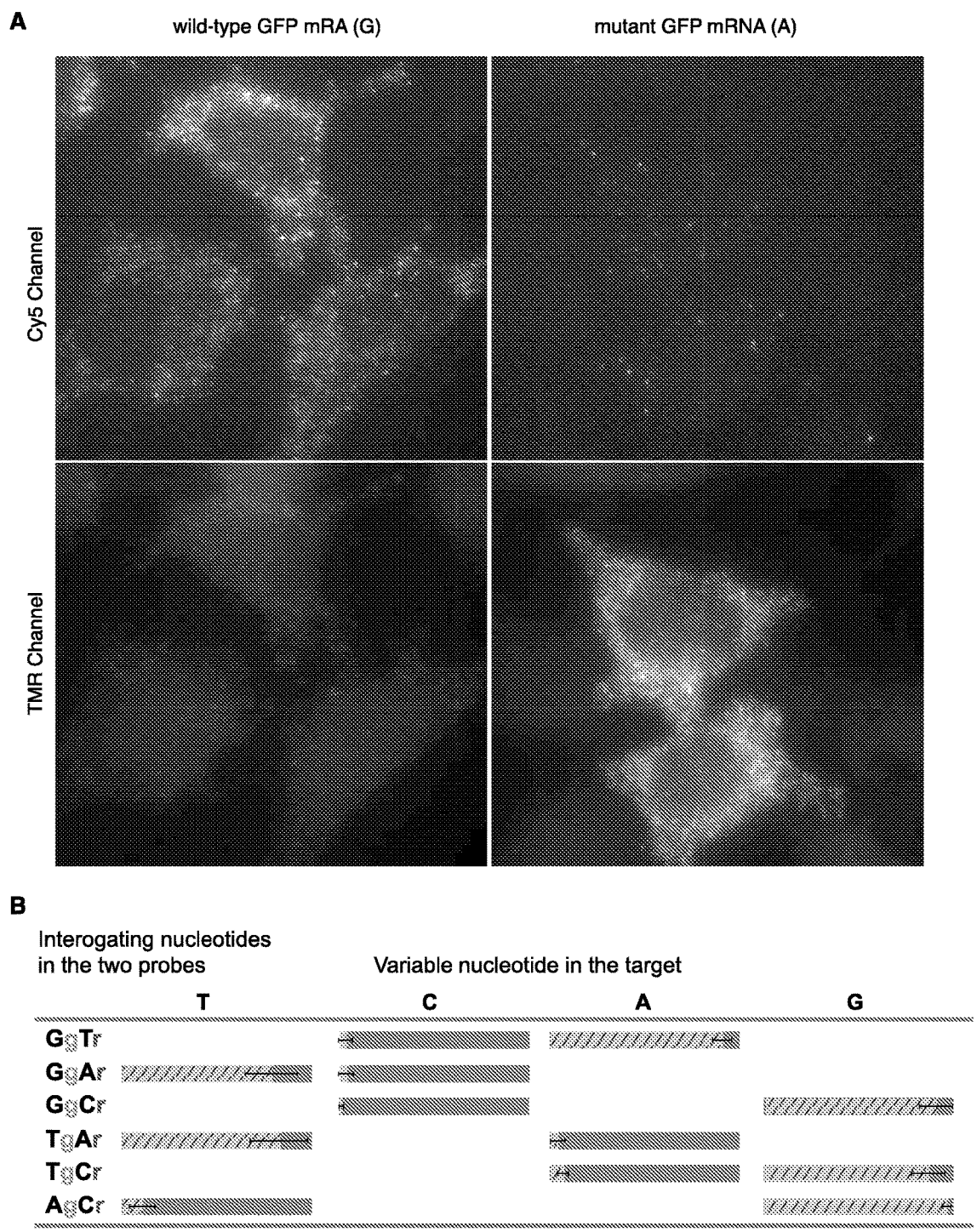
FIGS. 10A and B include microscopic images showing the simultaneous detection of single-nucleotide variations in mRNA molecules using two pairs of interacting hairpin probes and two pairs of HCR monomers. It also shows a graph depicting the quantitative levels of discrimination.

In Example 2, part B, we extended the experimentation of part A to samples containing one of four target-sequence variants; that is A, T, C or G. Against each target-sequence variant we used all six different combinations of two different arm-donating hairpin probes having loops perfectly complementary to one of the target-sequence variants. Detection assays and probes/HCR monomer systems were as described in part A. Each of the six probe mixtures was tested with each of the four target-sequence variants. As this series of experiments was designed, for each target-sequence variant three probe combinations should not yield a significant signal, because neither of the discriminatory arm-donating hairpin probes was perfectly complementary to the target-sequence variant; but three probe combinations should yield a significant signal, because one arm-donating hairpin probe was perfectly complementary to the target-sequence variant. An arm-donating probe that is perfectly complementary to the target sequence that is present should initiate HCR polymerization of the HCR monomer pair for which it was designed (either Cy5-labeled H3 and H4 or TMR-labeled H1 and H2) and yield a fluorescent signal of the appropriate color, while the other arm-donating probe in the mixture should only rarely initiate HCR polymerization by the other HCR monomer pair and yield only a minimum signal of their color. The results of Example 2B showed that that is exactly what occurred. First, assays in which neither arm-donating hairpin probe was complementary to the target-sequence variant did not yield significant fluorescent signal, an average total of 18 spots by microscopic analysis. No bar graphs are presented for these assays. On the other hand, assays in which one arm-donating hairpin probe was complementary to the target-sequence variant did yield significant signal, an average of 91 spots per cell. FIG. 10B presents the results for the latter as horizontal percent bar graphs. Each bar represents 100% of the spots detected in both colors, and the dark gray portion of each bar is the percentage of spots that were red (Cy5). The average proportion of spots in the color resulting from HCR initiation by the perfectly complementary arm-donating hairpin probe was 92%, with only 8% of the spots being in the color resulting from HCR initiation from the mismatched (single-nucleotide change) arm-donating hairpin probe. We also tested the six probe combinations with cells in which no GFP was expressed. They yielded, on average, 1.5 spots per cell. These results show that irrespective of the nature of nucleotide at the site of variation, the probe system discriminates with very high fidelity.

Figure 11:
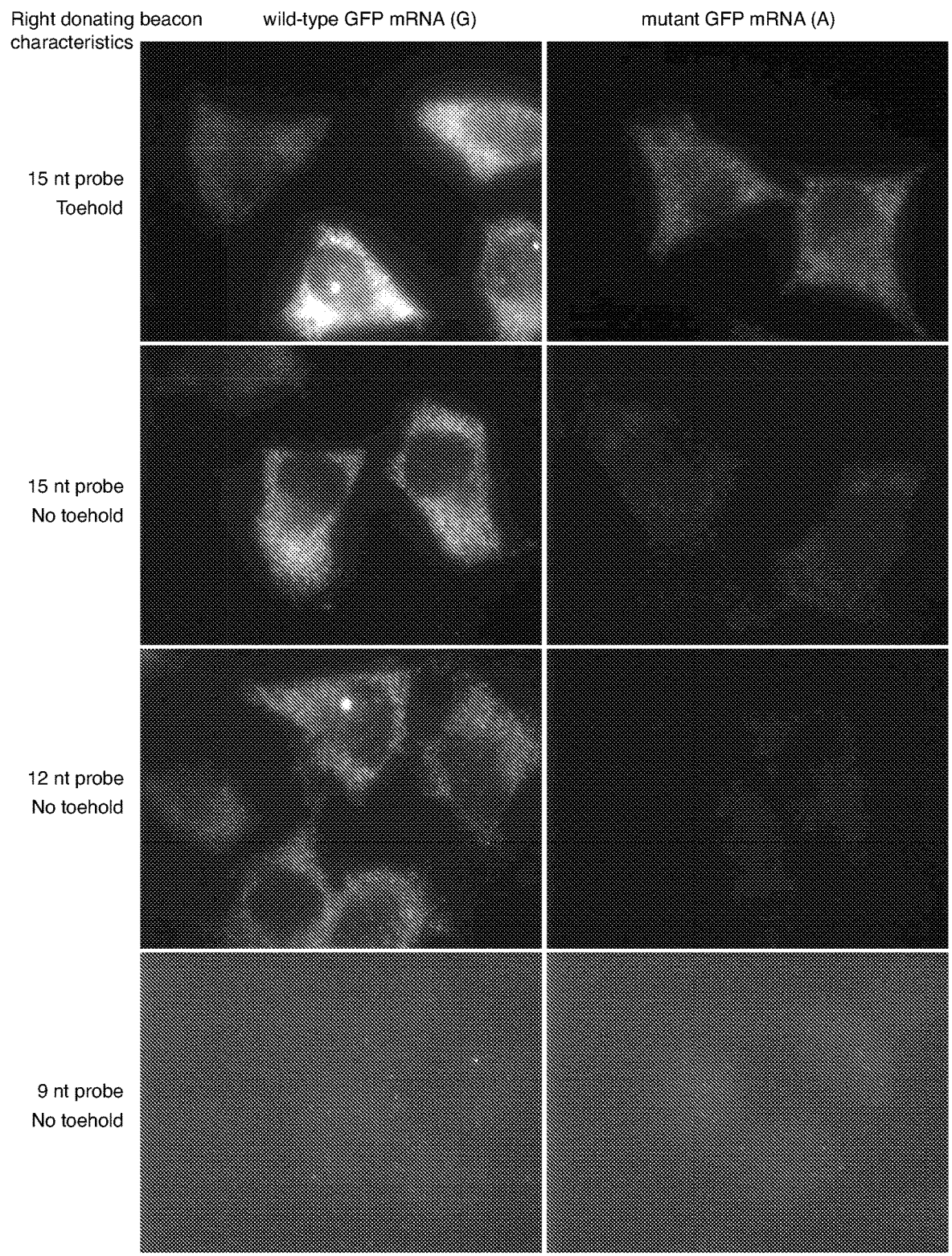
FIG. 11 is a set of microscopic images showing the simultaneous detection of single-nucleotide variations in mRNA molecules using interacting probe pairs having arm-donating probes of different designs.

Example 3 describes experiments regarding optimization of the structure of a pair of interacting hairpin probes to maximize their of the ability to discriminate between two closely related alleles, namely, a perfectly complementary target sequence and a sequence differing by a single nucleotide substitution, in a detection assay with HCR signal amplification. Key features of the interacting hairpin probes that impact their allele-discriminating ability are (a) the length of the loop of the arm-donating hairpin probe and (b) whether it contains a toehold-complementary sequence complementary to a single-stranded toehold sequence in the arm-acceptor hairpin probe for initiation of strand displacement (see FIG. 4) or does not (see FIG. 5). To demonstrate the impact of changes in these characteristics, we designed four interacting probe pairs that differed from each other by these two criteria and then tested each pair with cells expressing either the wild-type GFP mRNA, a (G) target-sequence variant, to which the arm-donating probe in each pair was perfectly complementary, or the mutant GFP mRNA, an (A) target-sequence variant, to which the arm-donating probe in each pair was mismatched by a single nucleotide. Representative microscopic images following probe hybridization and HCR signal amplification appear in FIG. 11, where the panels on the left are from assays with the perfectly complementary (G) target-sequence variant, and panels on the right are from assays with the mismatched (A) target-sequence variant. Panels in the top two rows compare use of and arm-donating hairpin probe having a 15-nucleotide-long loop with (top row) and without (second row) a toehold sequence in the arm-acceptor probe. These results show that arm-donating probes with 15-nt long loops yield strong signals (spots) for perfectly complementary target but weaker signals with the mismatched target. When the toehold-complementary sequence (and its single-stranded complementary toehold in the arm-acceptor probe) was eliminated, as shown in the second row of images, the signals from the mismatched target sequence diminished further, but the signals from the perfectly complementary target-sequence remained strong. The bottom three rows of panels in FIG. 11 compare results from arm-donating probes without toehold-complementary sequences but with stems 6 nucleotides long and a loop length of 15, 12 or 9 nucleotides. In the assay of this example, when the loop length was reduced from 15 nucleotides to 12 nucleotides, the signals from the mismatched target-sequence variant almost completely disappeared, whereas the signals from the perfectly complementary target-sequence variant remained almost as strong. However, when the loop length was reduced further to 9 nucleotides, the signals from both target-sequence variants were reduced to the background levels. The bottom two panels are presented at higher contrast then the rest in order to reveal few spots that are present in the images. These changes in probe structure and consequent changes in resulting signals illustrate how the discriminatory ability of particular pairs of interacting hairpin probes under particular assay conditions can be optimized.

Figure 12:
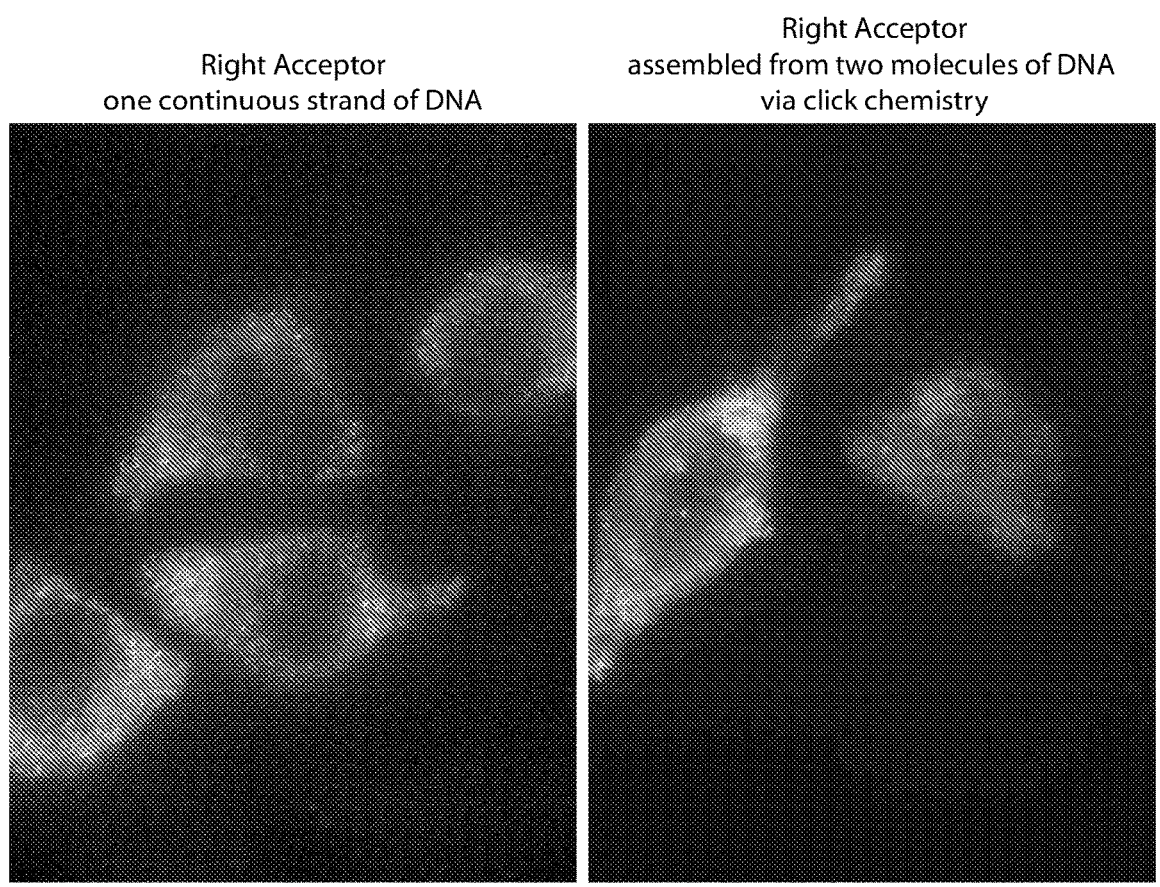
FIG. 12 is a set of microscopic images showing signals obtained by using interacting hairpin probes, where the arm-acceptor probe had only phosphodiester bonds and where the arm-acceptor probe included non-phosphodiester bonds resulting from click chemistry.

Example 4 demonstrates the ability to utilize a generic sequence to construct a probe of an interacting hairpin probe pair according to this invention. We chose arm-acceptor probe RA6.3 that was used in Example 1 and has the segments of probe 60 in FIG. 5. We used generic segments f-g'-f'-3' as a generic oligonucleotide, and we used target-complementary sequence P4-5' as a target-specific oligonucleotide. We linked the generic oligonucleotide to the target-specific oligonucleotide via click chemistry to form arm-acceptor probe RA6.3-click, which contained a click link. We compared the performance of probe RA6.3-click to the performance of "normal" (all phosphodiester internucleotide links) in the hybridization and HCR signal-amplification method of Example 1. Representative images shown in FIG. 12 demonstrate that the two kinds of arm-acceptor hairpin probes yield equivalent results. Therefore, despite a discontinuity in the phosphodiester backbone (due to 'click' links), the assembled hairpin probe and its interacting hairpin probe were able to interact when both were bound to the target sequence, undergo the required conformational change to generate an accessible HCR initiator, and initiate HCR amplification to produce HCR-amplified signal.

Example 5 demonstrates that in addition to mRNAs, other kinds of RNAs can also be detected using the interacting hairpin probes. In the experiment reported in Example 5, we targeted a small guide RNA. Small guide RNAs are used to guide the gene-editing tool Cas-9 (for Clustered regularly interspaced short palindromic repeats assisted endonuclease 9), to its target location within the genome (Cong et al. (2013) Science, 339: 819-823). Small guide RNAs have two functional elements: a portion that binds to the Cas-9 protein and a guide portion that is complementary to a target sequence within the genome. The target-sequence complementary element guides the resulting Cas-9 complex to its complementary genomic site where Cas-9 cleaves the DNA, which leads to the loss of the target gene. Example 5 describes a pair of interacting hairpin probes that target the Cas-9 guide sequence in HeLa cells engineered to express the RNA guide sequence and, when hybridized adjacently, initiate HCR signal amplification. Because the engineered guide RNA was under the control of a U6 promoter, it was expected to be localized in the nuclei of the engineered cells (Lee et al (2008) RNA 14:1823-1833). That differs from mRNAs, which are localized in the cytoplasm of cells.

Figure 13:
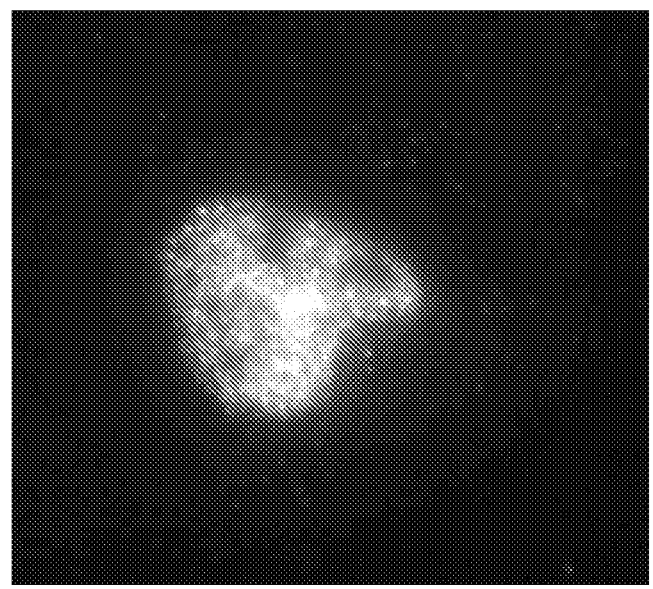
FIG. 13 is a microscopic image of signals from detection of a small guide RNA in a HeLa cell by an interacting hairpin probe pair and HCR signal amplification.

FIG. 13 shows an image of a HeLa cell in which the spots corresponding to the guide RNA are visible in the nucleus. Cells that were not transfected with this guide RNA did not yield a significant number of spots. Importantly, the observation that this RNA is localized within the nucleus, as expected from the promoter that was utilized by its parent plasmid, indicates that no matter where a target nucleic-acid sequence, here an RNA sequence, is present within a cell, interacting hairpin probes are able to recognize the target and lead to a report of its presence.

Example 6 describes a method according to this invention utilizing rolling circle amplification (RCA) rather than HCR for signal amplification. Referring first to FIG. 2, it is seen that RCA initiator I5 (there a tag on passively tagged hybridization probe 21) will prime copying of circular template CT to produce amplified product AP by RCA, and that fluorophore-labeled detector probe LP will detect the amplified product.

Example 6 describes a pair of interacting hairpin probes RDB RCA and RA RCA that hybridize adjacently on a nucleic-acid target sequence in fixed and permeabilized cells. Once hybridized, they interact to generate an initiator sequence, which in this case is RCA initiator I5. Addition of a circular template and a DNA polymerase leads to RCA signal amplification and detection as described in connection with FIG. 2. A schematic representation of the structure of such interacting hairpin probes is depicted in FIG. 7 as probes 71 and 72. A flow chart for such a method is shown in FIG. 7.

Example 7 compares the level of target sequence-specific signal and the level of background signal from flow cytometric detection of interferon gamma (IFNγ) mRNA expressed by stimulated human primary blood mononuclear cells (PBMCs) using three types of probing: a large number of short probes, all singly labeled with the same fluorophore; HCR using a large number of passively tagged probes; and HCR using half as many interacting hairpin probe pairs. PBMCs do not express IFNγ mRNA in their resting state, but when stimulated with phorbol 12-myristate 13-acetate (PMA) and ionomycin, about 15% of them respond by synthesizing IFNγ mRNA (Bushkin et al. (2015) Journal of Immunology 194: 836-841). Since the majority of cells do not express any IFNγ mRNA, this system allows for assessment of signal and background levels from the same cell populations. It will be appreciated that it is particularly important to achieve low levels of backgrounds in flow cytometry-based analyses of intracellular RNAs, because in flow cytometry only the integrated fluorescence from each cell is recorded, and unlike in microscopy, spots detection cannot be used as an aid to distinguish between specific signals and background signals.

In the tests of Example 7, fixed and permeabilized PBMCs and stimulated PBMCs were analyzed by flow cytometry following hybridization of three different types of probes and, for two probe types, HCR signal amplification. A first test of PBMCs and stimulated PBMCs included hybridization of 48 short (20-24 nucleotides long) random-coil DNA probes, each perfectly complementary to the IFNγ mRNA target sequence and labeled at its 3' end (directly labeled) with a single Cy5 fluorophore. A second test included hybridization of 48 probes having the same target-complementary sequences as in the first test, each having a 31-nucleotide long HCR initiator sequence as a 3' extension, with HCR amplification of Cy5-labeled HCR hairpin oligonucleotides H3 and H4 (Example 1). A third test included hybridization of 23 pairs of interacting hairpin probes, each pair having the same target-complementary sequences as successive probes in the first test, with HCR amplification of Cy5-labeled HCR hairpin monomers H3 and H4.

Figure 14:
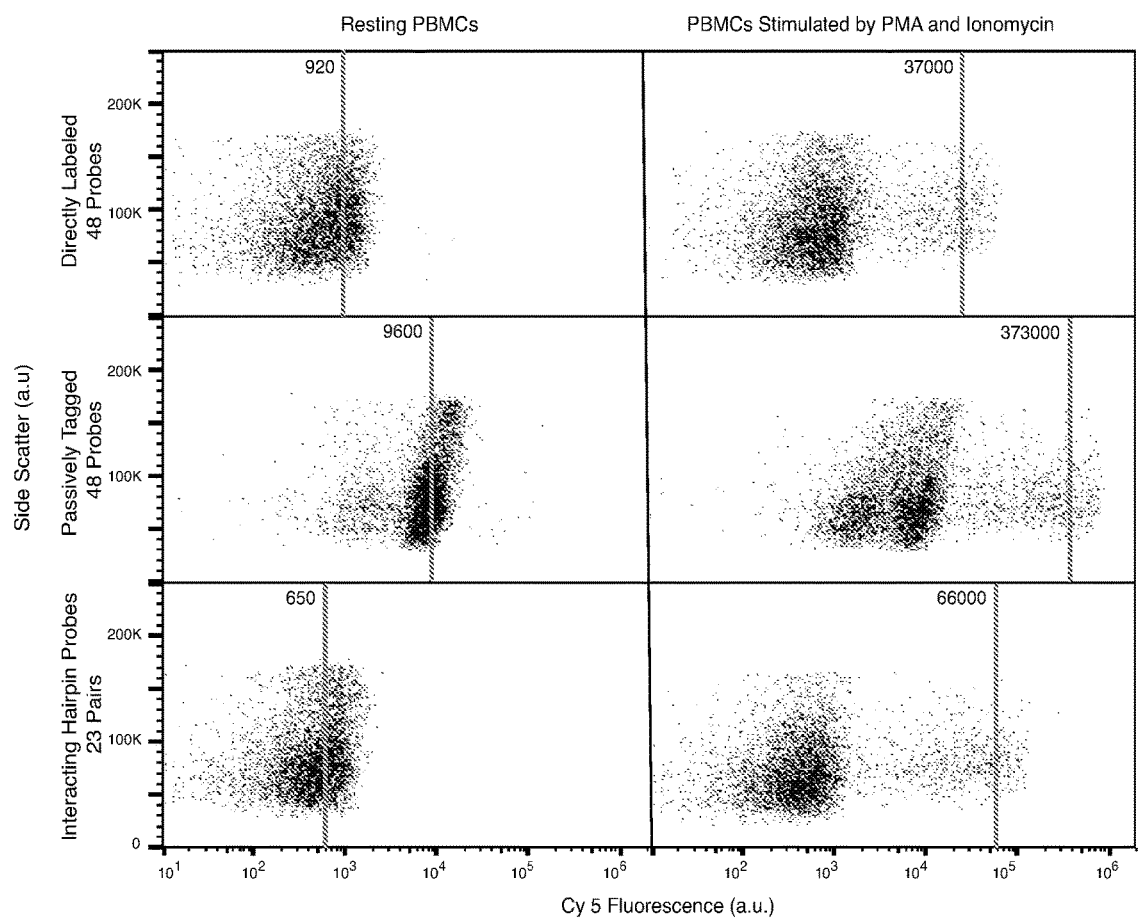
FIG. 14 is set of graphs comparing target-specific signals and background signals from flow cytometric detection using three types of probing: direct (no amplification) detection using a large number of short probes, all singly labeled with the same fluorophore; HCR using a large number of passively tagged probes; and HCR using half as many interacting hairpin probe pairs.

The results of the flow cytometry analysis are presented in FIG. 14, where the right panels represent the stimulated cells and the left panels represent resting cells. Each spot in these scatter plots represents a single cell where the abscissa represents the Cy5 fluorescence intensity of the cells and the ordinate represents the side-scatter of the same cells (the latter parameter relates to the size of the cell). The cells in the left panels appear in a single cluster which allows for the measurement of background signals, because unstimulated cells do not have any IFNγ mRNAs (Bushkin et al. 2015). The peak fluorescence intensities of these clusters are represented by the vertical bar on each panel with the peak fluorescence intensity being indicated at the top. The stimulated cells, on the other hand, diverge into two clusters, the one on the left, which represents unresponsive cells, and the one on the right, which represents cells producing IFNγ mRNA and which were thus more fluorescent (right panels). The peak fluorescence of these clusters in each panel is similarly indicated by a vertical bar. The peak fluorescences of unstimulated cells (left panels) and the peak fluorescences of the stimulated but unresponsive cells (right panels) are about the same.

The results shown in FIG. 14 reveal that, although the intensity of mRNA-specific signals increased about 10-fold as a consequence of HCR with passively tagged probes compared to the set of directly labeled probes (373,000 versus 37,000), the level of the background also increased to a similar extent (9600 versus 920), yielding the same signal-to-background ratio. However, significantly, HCR with the interacting hairpin probes not only yielded higher mRNA-specific signals compared to the set of directly labeled probes (66,000 versus 9700), the level of background was lower (650 versus 920). The signal-to-background ratios of the three probe systems were 40 for the directly labeled probes, 39 for HCR with passively tagged probes, and 102 for HCR with interacting hairpin probes. It will be appreciated that, although the absolute magnitudes of mRNA-specific signals yielded by HCR with the interacting hairpin probes were significantly lower than those of HCR with the passively tagged probes (66,000 versus 373,000), only half as many interacting hairpin probe pairs were used compared to the passively tagged probes (23 vs 48).

Comparison of FIG. 14 with FIG. 9B shows that as the number of passively tagged probes used for initiating HCR increased from one to 48, the levels of background signals increased to a great extent, whereas, in contrast, the background signals yielded by the interacting hairpin probes did not increase appreciably when the number of probe pairs increased from one pair to 23.

Example 8 demonstrates the ability of HCR with interacting hairpin probes of this invention to detect point mutations. For this demonstration we chose mutation L858R in the epidermal growth factor receptor (EGFR) mRNAs in cancer cell lines. Some EGFR mutations render the cancer susceptible to drugs that bind to EGFR, whereas other EGFR mutations in this gene render the cancer impervious to those drugs (Sharma et al. (2007) Nature Review Cancer 11:169-181). Our chosen somatic mutation L858R changes a single wild-type thymidine (T) residue to a mutant guanosine (G) residue at position 2573 of EGFR mRNA (cDNA sequence shown in Example 8) and indicates that tyrosine kinase inhibitors (TKIs) such as erlotinib and gefitinib will be effective against the cancer. For FISH with microscopic detection we selected two cells lines, H1975, which is derived from a non-small cell lung cancer and is known to harbor this mutation in one of the two copies of its EGFR gene (heterozygote); and HeLa cell line that does not contain this mutation and is thus wild-type with respect to this mutation (Kawahara et al Clinical Cancer Research (2010) 16:3163-3170). A mutant homozygote cell line is not available for this mutation.

For probing and initiation of HCR signal amplification we added to the fixed and permeabilized cells both interacting probe pairs of the four-probe system depicted in FIG. 4 and described above in connection with that figure and Example 2. The two hairpin acceptor probes were designed to bind to the target whether it is wild-type or mutant, whereas only one of the two arm-donating hairpin probes was designed to bind to each target. In this experiment, with reference to FIG. 4, right arm-donating hairpin probe 49, which is complementary to the mutant target sequence, was designed to interact with right acceptor hairpin probe 50 to initiate synthesis of HCR monomers H3 and H4, that were labeled with CY5; and left arm-donating hairpin probe 48, which is complementary to the wild-type target sequence, was designed to interact with left acceptor hairpin probe 47 to initiate synthesis of HCR monomers H1 and H2, that were labeled with TMR.

In order to demonstrate that the spots generated by interacting hairpin probe pairs generally stem from EGFR mRNAs, we simultaneously hybridized (with the two pairs of interacting hairpin probes) a set of 48 short random-coil DNA probes, each perfectly complementary to both the wild-type and mutant target sequence and labeled at its 3' end (directly labeled) with a single Texas Red fluorophore. These probes will bind to both kinds of targets and will produce signal in the Texas Red channel. They were employed as "tracer" or "marker" probes to confirm that the HCR signals were arising from the intended targets. It was expected that virtually all mRNA molecules in the cell would be detected in the Texas Red channel (Raj et al. (2008) Nature Methods 5:877-879). Specific HCR signals that emanate from EGFR mRNAs were expected to co-localize with these Texas Red signals, whereas, non-specific HCR signals were not expected to co-localize with the Texas Red signals.

Example 8 reports two experiments. In a first experiment we used a one-step hybridization reaction wherein the hybridization reaction mixture (50 µl) contained the set of short directly labeled probes, 5 ng of each arm-donating hairpin probe, and 5 ng of each acceptor hairpin probe. For a second experiment we made two changes: we performed probe hybridization in two-steps separated by washing. The reaction mixture for the first hybridization contained the acceptor probes but not the arm-donating probes, and the reaction mixture for the second hybridization contained the arm-donating hairpin probes but not the acceptor probes. For the second experiment the amount of each arm-donating hairpin probe was increased from 5 ng to 20 ng. We note that the hairpin sequences, reaction-mixture concentrations, and procedures of the foregoing experiments, although sufficient for this demonstration, were not optimized. Additionally, we did not ascertain the relative expression levels of the two alleles, which may well be imbalanced (Milani et al. (2017) Allelic imbalance in gene expression as a guide to cis-acting regulatory single nucleotide polymorphisms in cancer cells, Nucleic Acids Research 35:e34).

Figure 15:
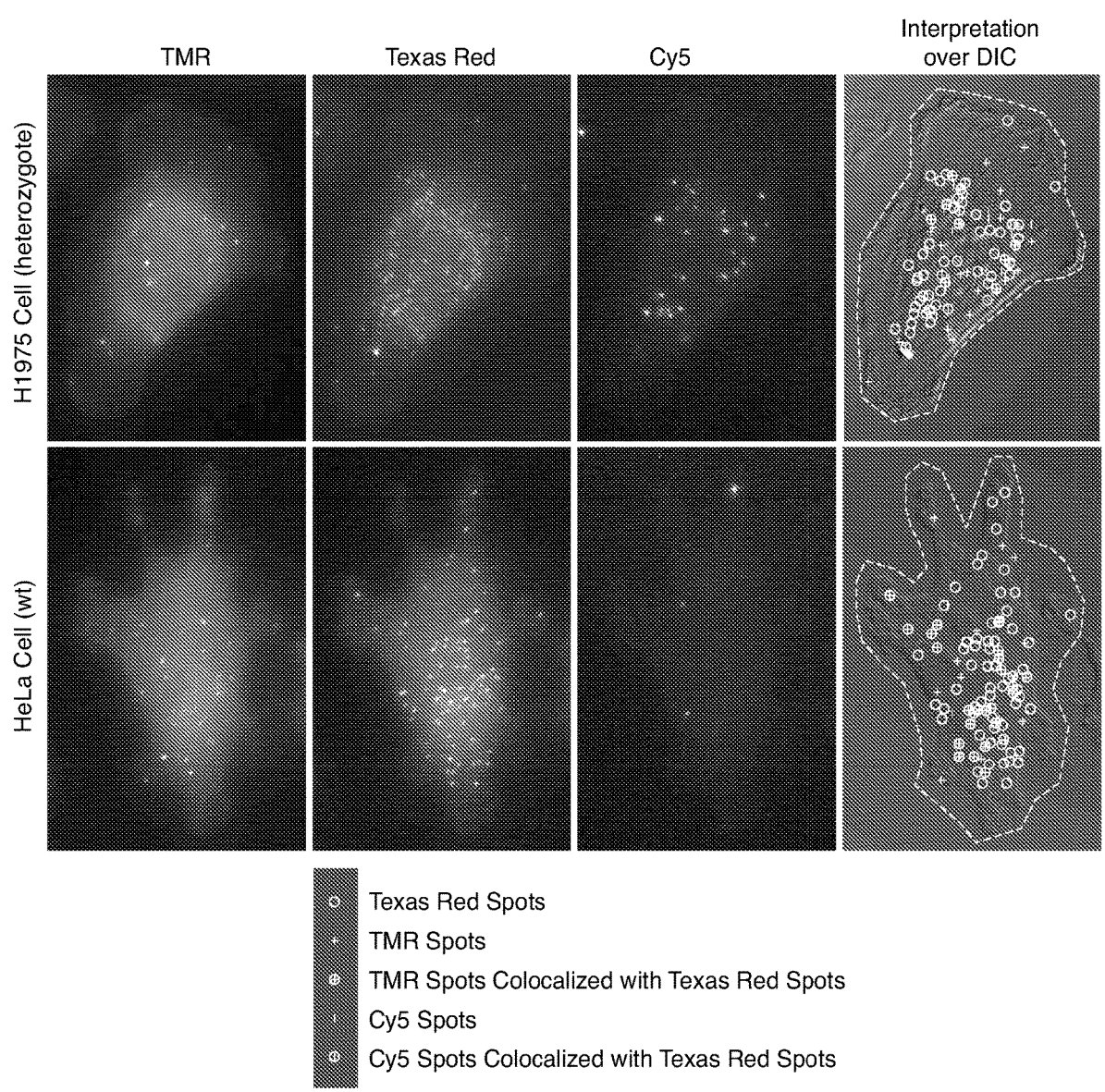
FIG. 15 is a set of microscopic images illustrating the detection of a heterozygous point mutation in EGFR mRNA.

Images and image analyses are presented from one cell each of H1975 and HeLa cell lines in FIG. 15. In this figure, the horizontal rows of panels show the images of the same cell obtained from four different channels that are indicated. The top row (H1975 cell) shows more Cy5 spots than does the bottom row (Hela cell), demonstrating successful detection of the L858R mutation in a heterozygous sample. Table 2 sets forth the number of spots counted in these experiments, namely: the Texas Red spots; the TMR spots that co-localized with the Texas Red spots and those that did not; and the Cy5 spots that co-localized with the Texas Red spots and those that did not ("Alone"). The top two rows are the single cells imaged in FIG. 15 during the first experiment. The middle two rows are averages of 60 cells from the first experiment. The bottom two rows are averages of 50 cells from the second experiment. The standard deviations were about 30% of the values reported.

In the first experiment using one-step hybridization of interacting hairpin probes, we found that on average, the H1975 cells express 42.5 molecules of EGFR mRNAs, whereas, the HeLa cells produce 18.3 molecules of this mRNA. In H1975 cells the interacting hairpin probes were able to detect 34% of the targets, whereas, in HeLa cells they are able to detect 20% of the targets. In the heterozygote cell line H1975, the probes produced signals that indicate that 66% of the detected mRNA molecules (100*((9.4/(9.4+4.9))) were mutant and the rest are wild-type, whereas in the wild-type cell line HeLa, 92% of the molecules (100*(3.3/(3.4+0.2))) were found to be wild-type and rest being the mutant. This analysis, which relies on Texas Red signals as guides, points to the exquisite specificity of the probes towards the mutation. The results of the first experiment also show that a number of spots in both TMR and Cy5 channels do not co-localize with Texas Red spots. Since these spots arise from potentially non-specific sources, and decrease the sensitivity of assays, we sought to decrease their number by performing two-step hybridization.

Comparison of TMR "Alone" and Cy5 "Alone" spots in the last two rows versus the middle two rows indicates that changing from one-step to two-step probe hybridization decreased the average number of non-co-localized spots significantly, while the specific spots (those that were co-localized with Texas red) remained about the same or increased slightly. Thus, the distinction between heterozygote and wild-type became even more accurate and reliable than it was with one-step hybridization. This distinction can be made without the knowledge of co-localization with the set of short, directly labeled probes as tracers.

The results of the two experiments suggest that mutant L858R mRNA targets are detected with higher efficiency than the wild-type targets. In one-step hybridization (60 cells) of H1975: 44% of the MUT mRNAs were detected (9.4/21.2), and 23% of the WT mRNAs were detected (4.9/21.2), whereas, in the two-step hybridization (50 cells) of H1075: 47% of the MUT mRNAs were detected (12.9/27.3), and 13% of the WT mRNAs were detected (3.6/27.3). The numerators in these calculations represent the number of spots in TMR and Cy5 channels that were co-localized with Texas Red and the denominators represent the half of total Texas Red mRNA molecules (Table 2). The lower efficiency of detection of the wild-type mRNA was also apparent in the wild-type cells line HeLa. In this case in one-step hybridization (60 cells) of HeLa: 19% of the WT mRNAs were detected (3.4/18.3), and (erroneously) only 1% responded to the mutant probe (0.2/18.3). Similarly, in the two-step hybridization (50 cells) of HeLa: 17% of the WT mRNAs were detected (3.4/20.1), and (erroneously) only 2% responded to the mutant probe (0.5/20.1). The denominators in these calculations are total Texas Red labeled mRNA molecules.

While it is possible that these differences result from an imbalance in the expression of two alleles due to an allelic imbalance, (Milani et al. 2017), another cause could be differential accessibility of the mRNA of two alleles to probes. A simple method of addressing this in order to optimize the assay is to separately normalize the number of spots for each allele. A second approach would be to "fine tune" the concentrations of the two probes, that is, increasing the concentration of the left donating beacon probe (WT) and decreasing the concentration of the right donating beacon probe (MUT), so that overall efficiency of the detection of the two mRNAs is about equal. Yet another approach would be to modify the structure of the left arm-donating probe or the left acceptor probe, or both, to increase the efficiency of initiator generation.

EXAMPLES

Example 1. Demonstration of Higher Signal-to-Background Ratios Achieved Through the Use of Interacting Hairpin Probes than is Achieved with Passively Tagged Probes In order to demonstrate the ability of interacting hairpin probe pairs to generate amplified signals specifically from intended mRNA target sequences, we expressed a heterologous mRNA encoding green fluorescent protein (GFP) in HeLa cells. GFP is normally not present in these cells. This mRNA served as the target of our probes. This system allowed us to assess target-specific signals from the cells that express the GFP mRNA and to assess background signals from HeLa cells that do not express GFP mRNA.

Sequences of oligonucleotides used in this example:

```
GFP target sequence
                                        (SEQ ID NO. 1)
5'-UCGUGACCACCCUGACCUACGGCGUGCAGUGCUUCAG

CCGCUACCCCGAC-3'

HCR hairpin oligonucleotide H3
                                        (SEQ ID No. 2)
5'-Cy5-ACAGACGACTCCCACATTCTCCAGGTGGGAGTCGTCTGT

AACATGAAGTA-3'

HCR hairpin oligonucleotide H4
                                        (SEQ ID No. 3)
5'-CTGGAGAATGTGGGAGTCGTCTGT TACTTCATGTTACAGACGACTCCCAC-Cy5-3'

Passively tagged probe
                                        (SEQ ID No. 4)
5'-GTCGGGGTAGCGGCTGAAGAAAAATACTTCATGTTACAGA

CGACTCCCAC-3'

Arm-Donating Hairpin Probe (RDB6.6)
                                        (SEQ ID No. 5)
5'-GTTACAGACGACTCCCACCACTGCACGCCGTGGGA-3'

Arm-Acceptor Hairpin Probe (RA6.3)
                                        (SEQ ID No. 6)
5'-GTCGGGGTAGCGGCTGAAGGTGGGAGTCGTCTGTAACTAC

TTCATGTTACAGACGACTCCCAC-3'
```

In the foregoing sequences, stem-forming complementary segments are underlined.

For these sets of experiments we either used a passively tagged hybridization probe against GFP mRNA analogous to the probe of Choi et al (2014), or we used a pair interacting hairpin hybridization probes according to this invention, first interacting hairpin probe RDB6.6 that contains a target-complementary sequence, and second interacting hairpin probe RA6.3. The passively tagged probe was designed such that its target-complementary segment (or probe sequence)

is the same as the target-complementary sequence (or probe sequence) in the second interacting hairpin probe RA6.3, the arm-acceptor probe. In this passively tagged probe, the target-complementary sequence (or probe sequence or probing sequence) at the 5' end is followed (towards its 3' end) by a spacer of 5 nucleotides (AAAAA) and then by an HCR initiator sequence I3, comprising sequences g',f'-3', which is an initiator for HCR hairpins H3 and H4. All oligonucleotides were obtained from Integrated DNA Technologies (IDT) (Coraville, Iowa, U.S.A.). HCR hairpin H3 was obtained with a 5' terminal amino label, and HCR hairpin H4 was obtained with a 3' terminal amino label. Oligonucleotides possessing amino labels were conjugated to Cy5 succinimidyl ester and then purified by HPLC as described before (Tyagi and Kramer (1996)). These labeled HCR hairpin monomers and the probes were further purified using denaturing polyacrylamide gel electrophoresis on a 10% polyacrylamide gel containing 8 M urea, resuspended in water, and quantified using a Nanodrop spectrophotometer. In order to ensure that the probes and the hairpin monomers were properly folded before use, the probes were diluted to 5 ng/µl and the HCR hairpin monomers were diluted to 25 nM in 2×SSC (about 100 µl solution), heated in boiling water for 2 minutes, and then allowed to cool at room temperature for 10 minutes.

The DNA template of this mRNA (plasmid pTREd2EGFP, Clontech) was transfected into HeLa cells using a standard protocol (Vargas et al. (2005)). The cells that were transfected (received the plasmid) became fluorescent due to the expression of GFP. Thereafter, the cells were detached from plastic dishes and transferred to glass coverslips where they were cultured for another day. These cells were fixed with 4% formaldehyde in 1× phosphate buffered saline (PBS), permeabilized with 70% ethanol, equilibrated with 10% formamide in 2λ saline sodium citrate (SSC) buffer (Ambion, Austin, Tex.) (probe wash buffer).

The passively tagged probe or the interacting probe pair was then added to the fixed and permeabilized cell, and the resulting mixture was incubated overnight in a humid chamber at 37° C. to hybridize the probes to the target sequence and to permit the probe-probe interactions. The hybridization reaction mixture (50 µl) contained 5 ng of each probe and 10% dextran sulfate (Sigma), 1 mg/ml *Escherichia coli* tRNA (Sigma), 2 mM ribonucleosidevanadyl complex (New England Biolabs, Ipswich, Mass.), 0.02% RNase-free bovine serum albumin (Ambion), 10% formamide and 2×SSC. After hybridization and interaction of the probe pair, the coverslips were washed twice with 1 ml of the probe wash buffer to remove unhybridized probes. Each wash was carried out at room temperature for 10 minutes. Finally, the cells were equilibrated with 50 mM $Na_2HPO_4$, 1 M NaCl, 0.05% (v/v) Tween-20, pH 7.4 (HCR buffer).

After removal of excess probes, HCR was performed in a 50 µl reaction for 4 hours at 37° C. in the humid chamber. The HCR reaction mixture contained 25 nM of each of HCR hairpin oligonucleotides H3 and H4, described earlier by Koss et al (2015) (Nature Communications 6:7294) dissolved in HCR buffer. HCR hairpin monomers were labeled with Cy5. After HCR amplification, excess (unused) HCR hairpin oligonucleotides were removed by washing in HCR buffer in the same manner as done for probe removal above. For both of the incubation steps (hybridization and HCR) a parafilm sheet was placed on a glass plate, the droplets of the reaction buffer were placed on the parafilm sheet and then coverslips were placed on the droplets with the side to which the cells are attached facing down. The coverslips were mounted and imaged as described earlier (Raj et al (2008)).

In a parallel experiment, aimed at analyzing signals by flow cytometry, cells were cultured on plastic dishes for one day after transfection and then detached. The detached cells were suspended in PBS, fixed and permeabilized. The probe pair was added and incubated for hybridization and interaction, followed by washing to remove unbound probes, performing HCR amplification, and washing again using the HCR buffer. However, since the cells were in suspension rather than attached to the coverslips, for each incubation/wash cycle, they were spun briefly in a centrifuge using a swinging tube rotor, and the supernatant was removed by aspiration and replaced by the fresh solution. After the final wash, these cells were suspended in the probe wash buffer and analyzed on a Becton Dickinson Accuri 6C Flow Cytometer in the fluorescein channel (for GFP) and in the Cy5 channel (for HCR products).

The coverslips were imaged with a 60× objective with a Nikon Eclipse Ti microscope in the DAPI, DIC, fluorescein (or GFP) and Cy5 channels. The first two channels enabled the identification of cells and their boundaries, the fluorescein channel enabled the identification of transfected cells, and the Cy5 channel was used for recording of the probe signals. Eleven optical sections were obtained for the Cy5 channel. The HCR-amplified signals appear as discrete spots. The spots within cell boundaries were counted using a previously described algorithm (Raj et al (2008)). Representative images are presented in FIG. 8. The left four panels in FIG. 8 are for HeLa cells transfected with the GFP template, and the right four panels are for HeLa cells not transfected with this template. We also analyzed cells from the parallel hybridization reactions performed on cell suspensions by flow cytometry. This analysis is presented in FIG. 9. In the scatter diagrams presented in the two upper panels of FIG. 9A, each dot represents the x-y coordinates of the fluorescence of a single cell in the Cy5 and the GFP channels respectively for reactions using the passively tagged probe (left panel) and for reactions with the interacting probe pair (right panel). We also analyzed the Cy5 fluorescence in the cells that were not transfected. Since these cells do not exhibit significant levels of GFP fluorescence only the Cy5 fluorescence is shown and the data is presented as continuous line histograms (FIG. 9B).

Example 2. Using Interacting Hairpin Probes for In Situ Detection of Allelic Variants of mRNA with Single-Molecule Sensitivity In order to demonstrate the utility of interacting hairpin probes for the detection of single-nucleotide variations of a target sequence, we created four single-nucleotide variants of the GFP coding sequence by mutating the wild-type d2EGFP sequence (Clontech) using a site-directed mutagenesis procedure (Change-IT, Affymetrix) at a particular location so that none of the changes would negatively impact its fluorescence. We substituted either, an adenosine, a cytosine, or a thymidine for the guanosine that is normally present at position 207 of the d2EGFP coding sequence. The sequence context of the nucleotide that was changed (underlined) is CCTACGGCGTGCAGTGCTTC (SEQ ID NO: 47). The plasmids encoding these four GFP variants were separately transfected into HeLa cells as described in Example 1. It was confirmed that each variant of yielded GFP-fluorescent cells.

The sequences of the oligonucleotides in this example:

```
GFP target sequence variants
                                        (SEQ ID NO. 1)
(G variant) 5'-UCGUGACCACCCUGACCUACGGCGUGCAGUG

CUUCAGCCGCUACCCCGAC-3'

(C variant)
                                        (SEQ ID No. 7)
5'-UCGUGACCACCCUGACCUACGGCGUCCAGUG

CUUCAGCCGCUACCCCGAC-3'

(A variant)
                                        (SEQ ID No. 8)
5'-UCGUGACCACCCUGACCUACGGCGUACAGUG

CUUCAGCCGCUACCCCGAC-3'

(T variant)
                                        (SEQ ID No. 9)
5'-UCGUGACCACCCUGACCUACGGCGUTCAGUG

CUUCAGCCGCUACCCCGAC-3'

Right arm-donating hairpin probe variants
C variant RDB6.6C
                                        (SEQ ID No. 5)
5'-GTTACAGACGACTCCCACCACTGCACGCCGTGGGA-3'

T variant RDB6.6T
                                        (SEQ ID No. 10)
5'-GTTACAGACGACTCCCACCACTGTACGCCGTGGGA-3'

A variant RDB6.6A
                                        (SEQ ID No. 11)
5'-GTTACAGACGACTCCCACCACTGAACGCCGTGGGA-3'

G variant RDB6.6G
                                        (SEQ ID No. 12)
5'-GTTACAGACGACTCCCACCACTGGACGCCGTGGGA-3'

Right arm-acceptor hairpin probe RA6.3
                                        (SEQ ID No. 6)
5'-GTCGGGGTAGCGGCTGAAGGTGGGAGTCGTCTGTAAC

TACTTCATGTTACAGACGACTCCCAC-3'

HCR hairpin oligonucleotide H3
                                        (SEQ ID No 2)
5'-Cy5-ACAGACGACTCCCACATTCTCCAGGTGGGAGTCGTCTGT

AACATGAAGTA-3'

HCR hairpin oligonucleotide H4
                                        (SEQ ID No. 3)
5'-CTGGAGAATGTGGGAGTCGTCTGTTACTTCATGTTACAGACGAC TCCCAC-Cy5 -3'

Left arm-donating hairpin probe variants
T variant LDB6.1T
                                        (SEQ ID No. 13)
5'-ACGAGGCACTGTACGCCCCTCGTAAATCCTCATCAATCATC-3'

C variant LDB6.1C
                                        (SEQ ID No. 14)
5'-ACGAGGCACTGCACGCCCCTCGTAAATCCTCATCAATCATC-3'

A variant LDB6.1A
                                        (SEQ ID No. 15)
5'-ACGAGGCACTGAACGCCCCTCGTAAATCCTCATCAATCATC-3'

G variant LDB6.1G
                                        (SEQ ID No. 16)
5'-ACGAGGCACTGGACGCCCCTCGTAAATCCTCATCAATCATC-3'

Left arm-acceptor hairpin probe LA6.1
                                        (SEQ ID No. 17)
5'-CCTCGTAAATCCTCATCAATCATCCAGTAAACCGCCGATGATTGA

TGAGGATTTACGAGG GTAGGTCAGGGTGGTCACGA-3'

HCR hairpin oligonucleotide H1
                                        (SEQ ID No. 18)
5'-GGCGGTTTACTGGATGATTGATGAGGATTTACGAGGAGCTCAGT

CCATCCTCGTAAATCCTCATCAATCATC-TMR-3'

HCR hairpin oligonucleotide H2
                                        (SEQ ID No. 19)
5'-TMR-CCTCGTAAATCCTCATCAATCATCCAGTAAACCGCCGATGA

TTGATGAGGATTTACGAGGATGGACTGAGCT-3'
```

In the wild-type GFP target sequence and arm-donating probes, the variable nucleotide is bolded. Underlined sequence segments indicate arms of hairpin stems.

A. Probing Either of Two Target Variants with Two Interacting Probe Pairs

We first separately probed cells expressing the G variant (wild-type) and cells expressing the A variant of GFP mRNA with a set of two interacting hairpin probe pairs (four probes consisting of RA6.3, LA6.1, RDB6.6C, whose loop sequence is complementary to the G target-sequence variant, and LDB6.1T, whose loop is complementary to the A target sequence variant). Utilizing this probe set, if arm-donating probe RDB6.6C binds such that its stem opens, its donating arm can then interact with arm-acceptor probe RA6.3, freeing its HCR initiator sequence, which can then initiate HCR amplification of Cy5-labeled hairpin oligonucleotides H3 and H4, yielding a Cy5 signal. However, if instead arm-donating probe LDB6.1T binds such that its stem opens, its donating arm can to it then interact with arm-acceptor probe LA6.1, freeing its HCR initiator sequence, which can then initiate HCR amplification of TMR-labeled HCR hairpin oligonucleotides H1 and H2, yielding a tetramethylrhodaimine (TMR) signal.

The cells and the probes were prepared, and the hybridization-interaction incubation of each sample (G variant or A variant) was performed as in Example 1 using all four probes in each case. After removal of excess probes by washing as described in Example 1, HCR amplification was performed on each sample as described in Example 1, during which two sets of HCR hairpins Cy5-labeled H3 and H4, and TMR-labeled H1 and H2 were present. After removing excess (unused) HCR hairpin oligonucleotides, the coverslips were imaged with a 100× objective in a Zeiss Axiovert microscope in DAPI, DIC, TMR and Cy5 channels. Representative images obtained from the TMR and the Cy5 channels are presented for both samples in FIG. 10A. The results are described above in the Explanation of the Examples section. We repeated the foregoing experiment with the interrogating nucleotides of the arm-donating hairpins reversed; that is, with probe RDB6.6C replaced by probe RDB6.6T (complementary to the A target-sequence variant) and with probe LDB6.1T replaced with probe LDB6.1C (complementary to the G target-sequence variant) to wee if the color of dominant spots would reverse, which they did.

B. Probing Other Target Variants with Two Interacting Probe Pairs

We repeated Example 2A for all four variants of the GFP mRNA target sequence. We tested a sample with each target-sequence variant using six different probe mixtures, which differed in their six combination of two arm-donating hairpin probes. All assays included acceptor probes LA6.1 and RA6.3, as well as HCR hairpin oligonucleotides H1, H2, H3 and H4. The two arm-donating probes for each of the six combinations are identified in Table 1.

TABLE 1

| System Designation | Complementary Target-Sequence Variants | Left Arm-Donating Probe | Right Arm-Donating Probe |
|---|---|---|---|
| GgTr | C and A | LDB6.1G | RDB6.6T |
| GgAr | C and T | LDB6.1G | RDB6.6A |
| GgCr | C and G | LDB6.1G | RDB6.6C |
| TgAr | A and T | LDB6.1T | RDB6.6A |
| TgCr | A and G | LDB6.1T | RDB6.6C |
| AgCr | T and G | LDB6.1A | RDB6.6C |

In the system designation in Table 1, the capital letters identify, for each of the two arm-donating hairpin probes in the two interacting probe pairs, the loop nucleotide that is opposite the target-sequence variable nucleotide, and the color of the signal resulting from its opening, that is, either green (TMR) or red (Cy5).

Each of the six probe mixtures in Table 1 was tested with each of the four target sequences. For each probe mixture, two target-sequence variants are complementary to one of the two arm-donating probes, and two target-sequence variants are not complementary to either of the arm-donating probes, that is, they are non-cognate target-sequence variants. For example, the probe system designated GgTr included an arm-donating probe, which we call the left arm-donating probe, having a loop complementary to target-sequence variant C and an arm-donating probe, which we call the right arm-donating probe, having a loop sequence complementary to target-sequence variant A, so those two target-sequence variants were the cognate variants, while target-sequence variants G and T were the non-cognate variants. Assays that included non-cognate target-sequence variants did not yield significant fluorescent signals from either the TMR fluorophore resulting from hybridization and opening of the left arm-donating hairpin probe or the Cy5 fluorophore resulting from hybridization and opening of the right arm-donating hairpin probe. Results of assays that included cognate target-sequence variants are presented in FIG. 10B. In the horizontal percent bars (each bar representing 100%) in FIG. 10B, the hatched region with light grey background represents the percentage of green spots (TMR) and the continuous dark grey portion represents the percentage of red spots (Cy5).

Example 3. Optimization of the Allele-Discriminating Ability of Interacting Hairpin Probes We tested four pairs of interacting hairpin probes in detection assays using cells expressing either one of two target-sequence variants: GFP mRNA (G) (SEQ ID No. 1), that was perfectly complementary to the loop of the arm-donating hairpin probe, or GFP mRNA (A) (SEQ ID No. 8), that was mismatched to the loop of the arm-donating hairpin probe by a single nucleotide. The sequences of the oligonucleotides used in this example were as follows:

GFP target sequence variants
(G variant)
(SEQ ID NO. 1)
5'-UCGUGACCACCCUGACCUACGGCGUGCAGUG

CUUCAGCCGCUACCCCGAC-3'

(A variant)
(SEQ ID No. 8)
5'-UCGUGACCACCCUGACCUACGGCGUACAGUG

CUUCAGCCGCUACCCCGAC-3'

First probe pair
Arm-Donating Hairpin Probe RDB6.3
(SEQ ID No. 20)
5'-GTTACAGACGACTCCCA

CAGTCCAGCACTGCACGCCGTGGACTG-3'

Arm-Acceptor Hairpin Probe RA6.2
(SEQ ID No. 21)
5'-ATGTGGTCGGGGTAGCGGCTGAGGACT GTGGGAGTCGTCTGTAAC

TACTTCATGTTACAGACGACTCCCAC-3'

Second probe pair
Arm-Donating Hairpin Probe RDB6.1
(SEQ ID No. 22)
5'-GTTACAGACGACTCCCACAGCACTGCACGCCGTGTGGGA-3'

Arm-Acceptor Hairpin Probe RA6.0
(SEQ ID No. 23)
5'-ATGTGGTCGGGGTAGCGGCTGA GTGGGAGTCGTCTGTAAC

TACTTCATGTTACAGACGACTCCCAC-3'

Third probe pair
Arm-Donating Hairpin Probe RDB6.5
(SEQ ID No. 24)
5'-GTTACAGACGACTCCCACAGCACTGCACGCGTGGGA-3'

ARM-Acceptor Hairpin Probe RA6.0
(SEQ ID No. 23)
5'-ATGTGGTCGGGGTAGCGGCTGAGTGGGAGTCGTCTGTAAC

TACTTCATGTTACAGACGACTCCCAC-3'

Fourth probe pair
ARM-Donating Hairpin Probe RDB6.7
(SEQ ID No. 25)
5'-GTTACAGACGACTCCCACACTGCACGCGTGGGA-3'

ARM-Acceptor Hairpin Probe RA6.0
(SEQ ID No. 23)
5'-ATGTGGTCGGGGTAGCGGCTGAGTGGGAGTCGTCTGTAAC

TACTTCATGTTACAGACGACTCCCAC-3'

HCR hairpin oligonucleotide H3
(SEQ ID No. 2)
5'-Cy5-ACAGACGACTCCCACATTCTCCAGGTGGGAGTCGTCTGT

AACATGAAGTA-3'

HCR hairpin oligonucleotide H4
(SEQ ID No. 3)
5'-CTGGAGAATGTGGGAGTCGTCTGT

TACTTCATGTTACAGACGACTCCCAC-Cy5-3'

In the foregoing sequences the hairpin arm sequences are underlined.

In the first pair of probes, arm-donating hairpin probe RDB6.3 contained a 15-nt long loop sequence, and it contained a 5-nt long toehold-complementary sequence. Its interacting probe, arm-acceptor hairpin probe RA6.2 contained a 5-nt long toehold sequence. Referring to the sequence of probe RA6.2, the 22 nucleotides at the 5' end are complementary to the target sequence, and the next five nucleotides (GGACT) are the toehold sequence. In the second probe pair arm-donating hairpin probe RDB6.1 contained a 15-nt long loop sequence but no toehold-complementary sequence; and arm-acceptor hairpin probe RA6.0 contained no toehold sequence. In the third probe pair arm-donating hairpin probe RDB6.5 contained a 12-nt long loop sequence but no toehold-complementary sequence; and arm-acceptor probe RA6.0 contained no toehold sequence. Finally, in the fourth probe pair arm-donating hairpin probe RDB6.7 contained a 9-nt long loop sequence but no toehold-complementary sequence; and arm-acceptor probe RA6.0 contained no toehold sequence.

Each HCR detection method utilized, in addition to one of the target-sequence variants and one of the interacting hairpin probe pairs described above, a single pair of HCR hairpin oligonucleotides, H3 and H4. Reactions were carried out as described in Example 2. Results are presented in FIG. 11, in which each panel is a microscopic image of cells following probe hybridization and HCR signal amplification. The mRNA target-sequence variant is shown above each column of panels, and the characteristics of the arm-donating hairpin probe in each row of panels are indicated on the left of the panels.

Example 4. Linking Generic Hairpins to Target Specific Probes Via Non-Phosphodiester Bonds In order to investigate the possibility of preparing arm-acceptor probes from a generic hairpin and a target-complementary sequence specific to a particular target, we synthesized a version of arm-acceptor probe RA6.3 using click chemistry and compared its performance to "normal" arm-acceptor probe RA6.3 containing only phosphodiester bonds. Of the two components, the generic acceptor hairpin oligonucleotide was obtained with a 5' amino group, and the acceptor target-complementary sequence oligonucleotide was obtained with a 3' amino group. The sequences of the oligonucleotides used in this example were as follows:

```
Arm-acceptor probe generic hairpin
                                        (SEQ ID No. 26)
5'-Amino-GTGGGAGTCGTCTGTAAC

TACTTCATGTTACAGACGACTCCCAC-3'

Arm-acceptor probe specific target-complementary
sequence
                                        (SEQ ID No. 27)
5'-GTCGGGGTAGCGGCTGAAG-Amino-3'

Arm-acceptor probe RA6.3
                                        (SEQ ID No. 6)
5'-GTCGGGGTAGCGGCTGAAGGTGGGAGTCGTCTGTAAC

TACTTCATGTTACAGACGACTCCCAC-3'

GFP target sequence
                                        (SEQ ID NO. 1)
5'-UCGUGACCACCCUGACCUACGGCGUGCAGUGCUUCA

GCCGCUACCCCGAC-3'

Arm-donating hairpin probe RDB6.6
                                        (SEQ ID No. 5)
5'-GTTACAGACGACTCCCACCACTGCACGCCGTGGGA-3'

HCR hairpin oligonucleotide H3
                                        (SEQ ID No. 2)
5'-Cy5-ACAGACGACTCCCACATTCTCCAGGTGGGAGTCGTCTGT

AACATGAAGTA-3'

HCR hairpin oligonucleotide H4
                                        (SEQ ID No. 3)
5'-CTGGAGAATGTGGGAGTCGTCTGT TACTTCATGTTACAGACGACTCCCAC-Cy5-3'
```

In the foregoing sequences, stem arm sequences are underlined.

The 3' amino group of the target-complementary sequence oligonucleotide was modified to an azide functionality by using 4-azidobutyrate-N-hydroxysuccinimidyl ester (Sigma-Aldrich). Separately, the amino group at the 5'-terminus of the generic acceptor hairpin was conjugated to dibenzocyclooctyne (DBCO) using dibenzocyclooctyne-N-hydroxysuccinimidyl ester (Sigma-Aldrich). Both modified oligonucleotides were purified by high-pressure liquid chromatography. The two oligonucleotides were linked to each other by mixing them in equimolar ratios and incubating them overnight in buffer composed of 50 mM KCl, 2.5 mM MgCl$_2$, and 10 mM Tris-HCl (pH 8.0). We refer to the full-length conjugated oligonucleotide probe as RA6.3-click. It was purified using denaturing polyacrylamide gel electrophoresis using a 12% polyacrylamide gel containing 8 M urea, resuspended in water, and quantified using a Nanodrop spectrophotometer. RA6.3-click was folded into its hairpin conformation by heating and cooling as described earlier. Properly folded arm-acceptor probe RA6.3-click was then used in combination with arm-donating hairpin probe RDB6.6 and HCR monomers H3, H4 in a hybridization assay with HCR signal amplification and microscopic detection to image cells expressing wild-type GFP mRNA target-sequence variant G (SEQ ID No. 1) as described in Example 1. In parallel, we utilized "normal" arm-acceptor probe RA6.3 in the same assay method to image the cells expressing the same GFP mRNA. Representative images shown in FIG. 12.

Example 5. Detection of a Small Guide RNAs

We expressed a guide RNA target sequence against the Cox-2 gene in HeLa cells. This sequence was inserted in plasmid pGL3-U6-sgRNA-PGK-puromycin (Addgene) and the engineered plasmid was transfected into HeLa cells. Following transfection, cells were fixed and permeabilized as described in Example 1.

To detect the Cox-2 guide RNA, we designed a pair of interacting hairpin probes that initiate HCR amplification in the method of Example 1. These probes were prepared and purified as described in Example 1. The sequences of the oligonucleotides used in this example were as follows:

```
Cox-2 Guide RNA Target Sequence
                                        (SEQ ID No. 28)
5'-CCGGUGUACGUCUUUAGAGGGUCGGUUUUAGAGCUAGAAAUA

GCAAGUUAAAAUAAGGCUAGUCCGUUAUCAACUUG-3'

Arm-Donating Hairpin Probe for Cox-2
Guide RNA Target Sequence
                                        (SEQ ID No. 29)
5'-GTTACAGACGACTCCCACAGACGAATACA GCG

CGACCCTCTAAAGACGTTGTATTCGTCT-3'
```

Arm-Acceptor Probe for Cox-2 Guide RNA
Target Sequence (SEQ ID No. 30)
5'-TTAACTTGCTATTTCTAGCTCTAACGCTGTATTCGTCT

GTGGGAGTCGTCTGTAACTACTTCATGTTACAGACGACTCCCAC-3'

HCR hairpin oligonucleotide H3
(SEQ ID No. 2)
5'-Cy5-ACAGACGACTCCCACATTCTCCAGGTGGGAGTCGTCTGT

AACATGAAGTA-3'

HCR hairpin oligonucleotide H4
(SEQ ID No. 3)
5'-CTGGAGAATGTGGGAGTCGTCTGT

TACTTCATGTTACAGACGACTCCCAC-Cy5-3'

In the foregoing sequences, stem arm sequences are underlined.

Hybridization and interaction of the hairpin probe pair, HCR amplification, and imaging were performed as described in Example 1. Results are presented in FIG. 12, which shows an image of a HeLa cell in which the spots corresponding to the guide RNA are visible in the nucleus. The cells that were not transfected with this guide RNA did not yield a significant number of spots (not shown).

Example 6. Using Interacting Hairpin Probes in Combination with Rolling Circle Amplification This example describes reagents and a method for use of a pair of interacting hairpin probes to initiate signal amplification by rolling circle amplification (RCA) for detection of a nucleic-acid target sequence by sm-FISH. The target in this example is an array 3 sequence in an engineered GFP gene described earlier by Vargas et al (2011) Cell 147:1054-1065). A Chinese hamster cell line stably expressing a GFP-array3 construct is cultured on glass coverslips and then fixed and permeabilized in the same manner as described in previous Examples for HeLa cells.
The sequences of the oligonucleotides to be used are as follows:

Array 3 target sequence
(SEQ ID No. 31)
5'-UCGACGCGGAGACCACGCUCGGCUUGUCUUUCGCGCGCAAUGC

GACGCACGCGGAUAGUUAGCUGCGGCGACGAGGCACC-3'

Oligonucleotide for circular template
(SEQ ID No. 32)
5'-TTTAAGCGTCTTAACTATTAGCGTCCAGTGAATGCGAGTCCGTC

TAAGAGAGTAGTACAGCAGCCGTCAAGAGTGTCTAGTTCTGTCATA-3'

Splint oligonucleotide for circular template
(SEQ ID No. 33)
5'-TAAGACGCTTAAATATGACAGAACTA-3'

Arm-donating hairpin oligonucleotide, RDB RCA
(SEQ ID No. 34)
5'-GCTTAAATATGACAGAACTAAGTCCGAAAGACAAGCCGAGCGTG

GTCTCCGGACT-3'

Arm-acceptor hairpin oligonucleotide, RA RCA
(SEQ ID No. 35)
5'-CCGCGTGCGTCGCATTGCGCGC GGACT

TAGTTCTGTCATATTTAAGCTAAGACGCTTAAATATGACAGAACTA-3'

Detector Probe for RCA product
(SEQ ID No. 36)
5'-TGCGAGTCCGTCTAAGAGAG-TMR-3'

To create a circular template for RCA a linear oligonucleotide (SEQ ID No. 32) is phosphorylated at its 5' end using T7 polynucleotide kinase (New England Biolabs, Ipswich, Mass., U.S.A.), annealed to a splint oligonucleotide (SEQ ID No. 33), and then ligated using T4 DNA ligase (New England Biolabs) following manufacturer's instructions. The circularized template DNA is then dissociated from the splint oligonucleotide by denaturation for 10 min at 100° C. in 85% formamide, followed by purification by electrophoresis on a 10% polyacrylamide gel containing 8 M urea. The pair of interacting hairpin probes is purified and prepared was described in Example 1.

The interacting hairpin probe pair, arm-donating hairpin probe RDB RCA and arm-acceptor probe RA RCA, is hybridized to the target sequence in the fixed and permeabilized cells (5 ng of each probe for each 50 µl hybridization reaction), and allowed to interact. Excess (unbound) probes are removed in the manner described in Example 1. The circularized template oligonucleotide (5 ng in 50 µl hybridization reaction mixture) is then added and hybridized for 1 hour at 37° C. Unbound (excess) circularized template is removed by two rounds of washing with probe wash buffer. The sample then is equilibrated with polymerase buffer composed of 50 mM Tris-HCl (pH 7.5), 10 mM $MgCl_2$, 10 mM $(NH_4)_2SO_4$, 4 mM DTT, 250 ng/µl BSA, 0.05% Tween-20, and 0.25 mM of each of the four nucleotide triphosphates. RCA signal amplification is carried out in 50 µl of the same buffer in presence of 0.125 U/µl phi29 DNA polymerase (New England Biolabs) for 1 hour at 37° C. The coverslips are then transferred to a solution containing a TMR-labeled detector probe (SEQ ID No. 36) for the RCA product (5 ng in 50 µl of probe wash buffer) and incubated in the solution for 30 minutes at 37° C. Excess (unbound) copies of the detector probe are removed by two washes with the probe wash buffer, and the coverslips are mounted for microscopic observation, which is performed as described in Example 1. In this procedure it is important to use a DNA polymerases with high processivity and high strand-displacement ability. In this regard the DNA polymerase bacteriophage φ29 (New England Biolabs) is a suitable choice.

A number of variations are possible for steps of the method described above. For example, instead of using a preformed circular template, a linear version of the circular template can be used. In that case, the single-stranded RCA initiator sequence resulting from interaction of the interacting hairpin probes will serve as the splint, and circularization will be achieved by an in-situ ligation step. This will reduce the effort required for oligonucleotide preparation. Furthermore, instead of using a linear detector probe for RCA product detection as described above, which requires the washing steps for removal of the excess detector probe, a homogeneous detection probe, preferably a molecular beacon probe, can be utilized. This will obviate the last washing steps, if desired.

Example 7. Using HCR with Interacting Hairpin Probes and Flow Cytometric Detection of mRNAs It is more critical to achieve low levels of backgrounds in flow cytometry-based analyses of intracellular RNAs than in microscopy-based analyses, because in flow cytometry only the integrated fluorescence from each cell is recorded, and unlike in microscopy the spots detection cannot be used as an aid to distinguish between specific signals and background signals. To demonstrate that HCR detection with interacting hairpin probes yields higher signals-to-background ratios in flow cytometry than HCR detection with passively tagged probes and detection with directly labeled probes, we detected IFNγ mRNA in primary blood mononuclear cells (PBMCs) with all three probe types. PBMCs do not express IFNγ mRNA in their resting state, but when they are stimulated with phorbol 12-myristate 13-acetate (PMA) and ionomycin, about 15% of them respond by synthesizing IFNγ mRNA (Bushkin et al. (2015) Journal of Immunology 19: 836-841). Since the majority of cells do not express any IFNg mRNA, this system allows for assessment of signal and background levels from the same cell populations.

Probe Sequences and Synthesis

The sequence of IFNγ mRNA, set forth as the corresponding cDNA sequence is shown below:

Probe sequences were as follows:
Forty-Eight Short, Directly Labeled Probes

The reverse complements of the underlined and gray-shaded sequences in the IFNγ cDNA sequence above.
Passively Labeled HCR Probes The same set of sequences were also used for the target complementary regions of the passively tagged HCR probes. However, at their 3' ends, there was appended the following sequence AAAAATACTTCATGTTACAGACGACTCC-CAC (SEQ ID No. 38), which serves as an initiator of HCR.
Twenty-Three Right Arm-Donating Hairpin Probes Their general sequences were: GTTACAGACGACTCC-CACNNN...NNNGTGGGA (SEQ ID No. 39), where NNN...NNN indicates the reverse complement of one of 23 underlined sequences in the IFNγ cDNA sequence above, where the sequence to the left of NNN...NNN, namely, GTTACAGACGACTCCCA (SEQ. ID No. 40) is the right arm of each probe (corresponding to the regions f' and e' in

```
                                                    (SEQ ID No. 37)
GTGCAGCACATTGTTCTGATCATCTGAAGATCAGCTATTAGAAGAGAAAGATCA

GTTAAGTCCTTTGGACCTGATCAGCTTGATACAAGAACTACTGATTTCAACTTCTT

TGGCTTAATTCTCTCGGAAACGATGAAATATACAAGTTATATCTTGGCTTTTCAG

CTCTGCATCGTTTTGGGTTCTCTTGGCTGTTACTGCCAGGACCCATATGTAAAAG

AAGCAGAAAACCTTAAGAAATATTTTAATGCAGGTCATTCAGATGTAGCGGATA

ATGGAACTCTTTTCTTAGGCATTTTGAAGAATTGGAAAGAGGAGAGTGACAGAA

AAATAATGCAGAGCCAAATTGTCTCCTTTTACTTCAAACTTTTTAAAAACTTTAA

AGATGACCAGAGCATCCAAAAGAGTGTGGAGACCATCAAGGAAGACATGAATG

TCAAGTTTTTCAATAGCAACAAAAAGAAACGAGATGACTTCGAAAAGCTGACTA

ATTATTCGGTAACTGACTTGAATGTCCAACGCAAAGCAATACATGAACTCATCCA

AGTGATGGCTGAACTGTCGCCAGCAGCTAAAACAGGGAAGCGAAAAAGGAGTC

AGATGCTGTTTCGAGGTCGAAGAGCATCCCAGTAATGGTTGTCCTGCCTGCAATA

TTTGAATTTTAAATCTAAATCTATTTATTAATATTTAACATTATTTATATGGGGAA

TATATTTTTAGACTCATCAATCAAATAAGTATTTATAATAGCAACTTTTGTGTAAT

GAAAATGAATATCTATTAATATATGTATTATTTATAATTCCTATATCCTGTGACTG

TCTCACTTAATCCTTTGTTTTCTGACTAATTAGGCAAGGCTATGTGATTACAAGGC

TTTATCTCAGGGGCCAACTAGGCAGCCAACCTAAGCAAGATCCCATGGGTTGTGT

GTTTATTTCACTTGATGATACAATGAACACTTATAAGTGAAGTGATACTATCCAG

TTACTGCCGGTTTGAAAATATGCCTGCAATCTGAGCCAGTGCTTTAATGGCATGT

CAGACAGAACTTGAATGTGTCAGGTGACCCTGATGAAAACATAGCATCTCAGGA

GATTTCATGCCTGGTGCTTCCAAATATTGTTGACAACTGTGACTGTACCCAAATG

GAAAGTAACTCATTTGTTAAAATTATCAATATCTAATATATATGAATAAAGTGTA

AGTTCACAACTA
```

FIG. 3A), and where the sequence to the right of NNN...NNN, namely, GTGGGA (SEQ ID No. 41) is complementary to a part of this sequence (corresponding to region e in FIG. 3A).

Twenty-Three Right Acceptor Hairpin Probes

Their sequences were the reverse complements of the shaded sequences in the IFNγ cDNA sequence above, excluding the first one, to each of which was appended at its 3' end the generic arm-acceptor probe hairpin (SEQ ID No. 26) described in Example 4.

A Cy5 fluorophore was conjugated to the 3' end of each of the short, directly labeled probes. Each right arm-donating hairpin probe was prepared by fully automated DNA synthesis (IDT DNA Inc.). Each right acceptor probe, on the other hand, was prepared by ligating the target specific portion of the probe with the generic right acceptor hairpin by click chemistry. For this we started with a pool of 23 oligonucleotides (having the reverse complements of the shaded sequences in the IFNγ cDNA sequence above, excluding the first and the last ones) each at an equimolar concentration, and then and linked them with the generic arm-acceptor probe hairpin (SEQ ID No. 26) at their 3'-ends as described in Example 4. After their synthesis via click chemistry, the right acceptor probes were purified by polyacrylamide gel electrophoresis as described in Example 4. The right arm-donating hairpin probes and right acceptor probes (each as a pool) were heated to 95° C. for 2 minutes and allowed to cool at room temperature for 10 min in 2×SSC (in separate tubes) to ensure that they had properly formed their respective hairpins.

PBMC's were purified from blood. A portion was not stimulated ("resting"), and a portion was stimulated with PMA and ionomycin. Both unstimulated cells and stimulated cells were fixed with formaldehyde, and permeabilized with alcohol and probed with the set of short, directly labeled probes as described in Bushkin et al (2015) Journal of Immunology 194: 836-841). In a parallel set of hybridization reactions, we also probed the cells with the set of passively tagged HCR probes and with the set of interacting hairpin probes. For each 50 μl hybridization reaction, we used 25 ng of the short, directly labeled probes or, 250 ng of the passively tagged probes or, 250 ng of right donating beacon probe set together with 250 ng of the right acceptor probe set. As discussed earlier, each probe set was composed of equimolar concentrations of multiple probes. After an overnight hybridization at 37° C., cells were washed twice in the probe wash buffer. While the reactions with the short, directly labeled probes were analyzed after this step, the reactions with the passively tagged HCR probes and with interacting hairpin probes were washed with the HCR buffer and subjected to HCR amplification using HCR hairpins H3 and H4 labeled with Cy5 for 2 hr at 37° C. as described in Example 1. After HCR the cells were washed twice with the HCR buffer and once with the probe wash buffer and analyzed. The flow cytometry analysis was performed as described in Example 1.

The results of the flow cytometry analysis are presented in FIG. 14. Panels in the right column represent the stimulated cells, and panels in the left column represent resting cells. Panels in the top row resulted from probing with the set of short, directly labeled probes. Panels in the middle row resulted from probing with the set of passively tagged HCR probes. Panels in the bottom row resulted from the set of interacting hairpin HCR probes. Each spot in these scatter plots represents a single cell, where the abscissa represents the Cy5 fluorescence of the cells and the ordinate represents the side-scatter of the same cells (the latter parameter relates to the size of the cells).

The cells in the left panels appear in single clusters whose peak fluorescence intensities are represented by the vertical bar on each panel. The values of peak intensity were 920 fluorescence units for the set short, directly labeled probes, 9600 units for the set of passively labeled HCR probes, and 650 for the set of interacting hairpin HCR probes. The stimulated cell in the right panels, on the other hand, diverge into two clusters. The left cluster represents unresponsive cells, and the right cluster represents cells producing IFNγg mRNA and which were thus more fluorescent. The peak fluorescence of the right cluster in each panel is indicated by a vertical bar. The values for those peak intensities were 37,000 arbitrary fluorescence units (a.u.) for the set of short, directly labeled probes, 373,000 units for the set of passively labeled HCR probes, and 66,000 units for the set of interacting hairpin HCR probes.

Example 8. Detecting Mutation L858R in the Epidermal Growth Factor Receptor (EGFR) mRNAs in Cancer Cell Lines Cell line H1975 and the HeLa cell line were obtained from ATCC (Manasas, Va.) and cultured according to the supplier's instructions. Cell line H1075 harbors somatic mutation L858R in one of the two copies of the EFGR gene (heterozygote), while the HeLa cell line does not contain that mutation. The mutation changes a thymidine (T) residue to a guanosine (G) residue at position 2573 of EGFR mRNA.

Probe Sequences and Synthesis

The sequence of EGFR mRNA, set forth as the corresponding cDNA sequence, is shown below:

(SEQ ID No. 42)
```
ATGCGACCCTCCGGGACGGCCGGGGCAGCGCTCCTGGCGCTGCTGGCTGCGCTCT

GCCCGGCGAGTCGGGCTCTGGAGGAAAAGAAAGTTTGCCAAGGCACGAGTAACA

AGCTCACGCAGTTGGGCACTTTTGAAGATCATTTTCTCAGCCTCCAGAGGATGTT

CAATAACTGTGAGGTGGTCCTTGGGAATTTGGAAATTACCTATGTGCAGAGGAAT

TATGATCTTTCCTTCTTAAAGACCATCCAGGAGGTGGCTGGTTATGTCCTCATTGC

CCTCAACACAGTGGAGCGAATTCCTTTGGAAAACCTGCAGATCATCAGAGGAAA

TATGTACTACGAAAATTCCTATGCCTTAGCAGTCTTATCTAACTATGATGCAAAT

AAAACCGGACTGAAGGAGCTGCCCATGAGAAATTTACAGGAAATCCTGCATGGC

GCCGTGCGGTTCAGCAACAACCCTGCCCTGTGCAACGTGGAGAGCATCCAGTGG
```

```
CGGGACATAGTCAGCAGTGACTTTCTCAGCAACATGTCGATGGACTTCCAGAACC

ACCTGGGCAGCTGCCAAAAGTGTGATCCAAGCTGTCCCAATGGGAGCTGCTGGG

GTGCAGGAGAGGAGAACTGCCAGAAACTGACCAAAATCATCTGTGCCCAGCAGT

GCTCCGGGCGCTGCCGTGGCAAGTCCCCCAGTGACTGCTGCCACAACCAGTGTGC

TGCAGGCTGCACAGGCCCCCGGGAGAGCGACTGCCTGGTCTGCCGCAAATTCCG

AGACGAAGCCACGTGCAAGGACACCTGCCCCCCACTCATGCTCTACAACCCCAC

CACGTACCAGATGGATGTGAACCCCGAGGGCAAATACAGCTTTGGTGCCACCTG

CGTGAAGAAGTGTCCCCGTAATTATGTGGTGACAGATCACGGCTCGTGCGTCCGA

GCCTGTGGGCCGACAGCTATGAGATGGAGGAAGACGGCGTCCGCAAGTGTAAG

AAGTGCGAAGGGCCTTGCCGCAAAGTGTGTAACGGAATAGGTATTGGTGAATTT

AAAGACTCACTCTCCATAAATGCTACGAATATTAAACACTTCAAAAACTGCACCT

CCATCAGTGGCGATCTCCACATCCTGCCGGTGGCATTTAGGGGTGACTCCTTCAC

ACATACTCCTCCTCTGGATCCACAGGAACTGGATATTCTGAAAACCGTAAAGGA

AATCACAGGGTTTTTGCTGATTCAGGCTTGGCCTGAAAACAGGACGGACCTCCAT

GCCTTTGAGAACCTAGAAATCATACGCGGCAGGACCAAGCAACATGGTCAGTTT

TCTCTTGCAGTCGTCAGCCTGAACATAACATCCTTGGGATTACGCTCCCTCAAGG

AGATAAGTGATGGAGATGTGATAATTTCAGGAAACAAAAATTTGTGCTATGCAA

ATACAATAAACTGGAAAAAAACTGTTTGGGACCTCCGGTCAGAAAACCAAAATTA

TAAGCAACAGAGGTGAAAACAGCTGCAAGGCCACAGGCCAGGTCTGCCATGCCT

TGTGCTCCCCCGAGGGCTGCTGGGGCCCGGAGCCCAGGGACTGCGTCTCTTGCCG

GAATGTCAGCCGAGGCAGGGAATGCGTGGACAAGTGCAACCTTCTGGAGGGTGA

GCCAAGGGAGTTTGTGGAGAACTCTGAGTGCATACAGTGCCACCCAGAGTGCCT

GCCTCAGGCCATGAACATCACCTGCACAGGACGGGGACCAGACAACTGTATCCA

GTGTGCCCACTACATTGACGGCCCCCACTGCGTCAAGACCTGCCCGGCAGGAGTC

ATGGGAGAAAACAACACCCTGGTCTGGAAGTACGCAGACGCCGGCCATGTGTGC

CACCTGTGCCATCCAAACTGCACCTACGGATGCACTGGGCCAGGTCTTGAAGGCT

GTCCAACGAATGGGCCTAAGATCCCGTCCATCGCCACTGGGATGGTGGGGCCC

TCCTCTTGCTGCTGGTGGTGGCCCTGGGGATCGGCCTCTTCATGCGAAGGCGCCA

CATCGTTCGGAAGCGCACGCTGCGGAGGCTGCTGCAGGAGAGGGAGCTTGTGGA

GCCTCTTACACCCAGTGGAGAAGCTCCCAACCAAGCTCTCTTGAGGATCTTGAAG

GAAACTGAATTCAAAAAGATCAAAGTGCTGGGCTCCGGTGCGTTCGGCACGGTG

TATAAGGGACTCTGGATCCCAGAAGGTGAGAAAGTTAAAATTCCCGTCGCTATC

AAGGAATTAAGAGAAGCAACATCTCCGAAAGCCAACAAGGAAATCCTCGATGA

AGCCTACGTGATGGCCAGCGTGGACAACCCCCACGTGTGCCGCCTGCTGGGCAT

CTGCCTCACCTCCACCGTGCAGCTCATCACGCAGCTCATGCCCTTCGGCTGCCTC

CTGGACTATGTCCGGGAACACAAAGACAATATTGGCTCCCAGTACCTGCTCAACT

GGTGTGTGCAGATCGCAAAGGGCATGAACTACTTGGAGGACCGTCGCTTGGTGC

ACCGCGACCTGGCAGCCAGGAACGTACTGGTGAAAACACCGCAGCATGTCAAGA

TCACAGATTTTGGGC(T)GGCCAAACTGCTGGGTGCGGAAGAGAAAGAATACCAT
```

-continued

GCAGAACGAGGCAAAGTGCCTATCAAGTGGATGGCATTGGAATCAATTTTACAC

AGAATCTATACCCACCAGAGTGATGTCTGGAGCTACGGGGTGACTGTTTGGGAG

TTGATGACCTTTGGATCCAAGCCATATGACGGAATCCCTGCCAGCGAGATCTCCT

CCATCCTGGAGAAAGGAGAACGCCTCCCTCAGCCACCCATATGTACCATCGATGT

CTACATGATCATGGTCAAGTGCTGGATGATAGACGCAGATAGTCGCCCAAAGTT

CCGTGAGTTGATCATCGAATTCTCCAAAATGGCCCGAGACCCCCAGCGCTACCTT

GTCATTCAGGGGATGAAAGAATGCATTTGCCAAGTCCTACAGACTCCAACTTCT

ACCGTGCCCTGATGGATGAAGAAGACATGGACGACGTGGTGGATGCCGACGAGT

ACCTCATCCCACAGCAGGGCTTCTTCAGCAGCCCCTCCACGTCACGGACTCCCCT

CCTGAGCTCTCTGAGTGCAACCAGCAACAATTCCACCGTGGCTTGCATTGATAGA

AATGGGCTGCAAAGCTGTCCCATCAAGGAAGACAGCTTCTTGCAGCGATACAGC

TCAGACCCCACAGGCGCCTTGACTGAGGACAGCATAGACGACACCTTCCTCCCA

GTGCCTGAATACATAAACCAGTCCGTTCCCAAAAGGCCCGCTGGCTCTGTGCAGA

ATCCTGTCTATCACAATCAGCCTCTGAACCCCGCGCCCAGCAGAGACCCACACTA

CCAGGACCCCCACAGCACTGCAGTGGGCAACCCCGAGTATCTCAACACTGTCCA

GCCCACCTGTGTCAACAGCACATTCGACAGCCCTGCCCACTGGGCCCAGAAAGG

CAGCCACCAAATTAGCCTGGACAACCCTGACTACCAGCAGGACTTCTTTCCCAAG

GAAGCCAAGCCAAATGGCATCTTTAAGGGCTCCACAGCTGAAAATGCAGAATAC

CTAAGGGTCGCGCCACAAAGCAGTGAATTTATTGGAGCATGA

The thymidine residue subject to the L858R mutation is bolded and in parentheses.

Forty-Eight Short, Directly Labeled Probes

The reverse complements of the underlined sequences in the EGFR cDNA sequence above. Twenty-four are 5' to the shaded sequence that includes the nucleotide (T) subject to mutation, and 24 are 3' to that sequence.

```
Right arm-donating hairpin probe EGFR 3.1 (mutant)
                                        (SEQ_ID No. 43)
GTTACAGACGACTCCCACAGTCC GTTTGGCC(C)GCCCAAAATGGACT.
```

The sequences that form a stem are underlined. The nucleotides that form a single-stranded loop and are complementary to the mutant target are bolded. The nucleotide of the single-nucleotide mutation is in parentheses.

```
Left arm-donating hairpin probe EGFR 3.0
(wild-type)
                                        (SEQ ID N. 44)
TAGGTGTTTGGCC(A)GCCCAAAATACCTACCTCGTAAATCCTCATCAAT

CATC.
```

The sequences that form a stem are underlined. The nucleotides that form a single-stranded loop and are complementary to the wild-type target are bolded. The nucleotide that is subject to mutation is in parentheses.

```
Right acceptor hairpin probe EGFR 3.0
                                        (SEQ ID No. 45)
CTCCTTCTGCATGGTATTCTTTCTCTTCCGCACCCAGCAGGACT

GTGGGAGTCGTCTGTAACTACTTCATGTTACAGACGACTCCCAC.
```

The sequences that form a stem are underlined. The nucleotides that are complementary to the mutant and wild-type targets are bolded.

```
Left acceptor hairpin probe EGFR 3.0
                                        (SEQ ID No. 46)
CCTCGTAAATCCTCATCAATCATCCAGTAAACCGCCGATGATTGAT

GAGGATTTAGGAGGTAGGTCTGTGATCTTGACATGCTGCGGTGT.
```

The sequences that form a stem are underlined. The nucleotides that are complementary to the mutant and wild-type targets are bolded.

The interacting hairpin probes were obtained from IDT DNA Inc. and then purified by polyacrylamide gel electrophoresis as described in Example 4. The right arm-donating hairpin probes and right acceptor probes were heated to 95° C. for 2 minutes and allowed to cool at room temperature for 10 min in 2×SSC (in separate tubes) to ensure that they have properly formed their respective hairpins. The short, directly labeled probes were obtained with 3' amino groups from Biosearch LGC and then coupled to Texas Red dye. The labeled probes were purified as described by Raj et al. (2008).

The cells were cultured on coverslips, fixed and permeabilized as described in Example 1.

In a first experiment the probe hybridization reaction mixture (50 µl) contained 25 ng of pooled short, directly labeled probes, 5 ng each of right arm-donating hairpin probe EGFR 3.1 (mutant), left arm-donating hairpin probe EGFR 3.1 (wild-type), right acceptor hairpin probe EGFR 3.0, and left acceptor hairpin probe EGFR 3.0. In addition to these probes, the hybridization mixture also contained 10% dextran sulfate (Sigma), 1 mg/ml *Escherichia coli* tRNA (Sigma), 2 mM ribonucleosidevanadyl complex (New England Biolabs, Ipswich, Mass.), 0.02% RNase-free bovine serum albumin (Ambion), 10% formamide and 2×SSC. This hybridization reaction mixture was placed over a stretched parafilm, and a coverslip was laid over it with cells facing down, followed by incubation at 50° C. overnight in a humid chamber. The coverslips were washed twice with probe wash buffer and once with HCR buffer.

In a second experiment probes hybridization was performed in two steps, and the concentration of the arm-donating hairpin probes was increased. In the first step the hybridization reaction mixture included the left and right acceptor probes but not the arm-donating hairpin probes. After this hybridization, which was performed under the same conditions as specified above but for 6 hr, excess acceptor probes were removed by two successive washes of coverslips with the probe wash buffer. Thereafter, a second hybridization was performed with a reaction mixture that included 20 ng of each of the right and left arm-donating hairpin probes but not the acceptor probes. The second hybridization was performed overnight. The Texas Red-labeled probes were included in both hybridization reactions. Excess arm-donating probes were removed by washing.

Next, in both experiments, HCR amplification was performed in HCR buffer as described in Example 1. The HCR reaction mixture included two sets of HCR hairpin oligonucleotides: Cy5-labeled H3 and H4, and TMR-labeled H1 and H2. After removing excess (unused) HCR hairpin oligonucleotides, the coverslips were imaged with a 63× objective with 1.4 numerical aperture in a Zeiss Axiovert microscope in DIC, DAPI, TMR, Texas Red and Cy5 channels, using a Prime Photometric sCMOS camera. In the TMR, Texas Red and Cy5 channels 16 optical sections separated from each other by 0.2 µm were acquired. These z-stacks were analyzed by a custom MATLAB image processing program that identifies spots in 3-D in each channel and then identifies the spots that are co-localized between each pairs of channels (Vargas et al. 2011). Spots that were co-localized in all three spots were rarely found.

Images and image analyses from the first experiment are presented from one cell each of cell line H1975 (top row) and the HeLa cell line (bottom row) in FIG. 15. The horizontal panels in each row show the images of the same cell obtained from four different channels (TMR, Texas Red, Cy5 and DIC) as indicated. The images are maximum intensity projections derived from the z-stacks, except for the DIC panels on the right, which correspond to the central layers of the z-stacks. The DIC panels display locations of each kind of spot that were identified with a key presented at the bottom of the figure.

Table 2 presents the results of counting spots in images of single cells from the two experiments. The number of spots are presented in different categories of spots: the total number of Texas Red spots, the number of TMR spots that were not co-localized ("Alone") with Texas Red spots, the number of Cy5 spots that were not co-localized with Texas Red spots, the number of TMR spots that were co-localized with Texas Red spots, and the number of Cy5 spots that were co-localized with Texas Red spots. The top two rows are the counts of single cells in the first experiment (one-step probes hybridization), namely the cells shown in FIG. 15. The next two rows are averages of the counts of 60 cells from the first experiment. The bottom two rows are averages of the counts of 50 cells from the second experiment (two-step probes hybridization). The standard deviations were about 30% of the values reported.

TABLE 2

Number of spots detected in single cells

| | | | Texas Red Total | TMR Alone | Cy5 Alone | Texas Red Co-localized with TMR | Texas Red Co-localized with Cy5 |
|---|---|---|---|---|---|---|---|
| One-step hybridization | Exemplary Cells (FIG. 15) | H1975 | 58 | 22 | 16 | 9 | 7 |
| | | HeLa | 84 | 16 | 2 | 23 | 0 |
| | Averages from 60 cells | H1975 | 42.5 | 17.0 | 13.2 | 4.9 | 9.4 |
| | | HeLa | 18.3 | 10.5 | 4.9 | 3.4 | 0.2 |
| Two-step hybridization | Averages from 50 cells | H1975 | 54.7 | 4.1 | 4.7 | 3.6 | 12.9 |
| | | HeLa | 20.1 | 4.1 | 0.9 | 3.4 | 0.5 |

The invention claimed is:

1. A pair of interacting hairpin oligonucleotide probes capable of hybridizing adjacently on a nucleic acid target sequence in fixed and permeabilized cells and interacting to generate a single-stranded initiator sequence capable of initiating a hybridization chain reaction (HCR) or rolling circle amplification (RCA) amplification, said probe pair comprising
   a first, arm-donating hairpin probe that is a stem-and-loop oligonucleotide having a double-stranded stem comprising two complementary arm sequences flanking a target-sequence-complementary single-stranded loop sequence, wherein one of the arm sequences (donating arm) includes a single-stranded extension, and
   a second, arm-acceptor hairpin probe that is a stem-and-loop oligonucleotide having a double-stranded stem comprising two complementary arm sequences flanking a single-stranded loop sequence, the loop and one arm comprising an HCR or RCA initiator sequence, the other arm having a single-stranded extension comprising at least a terminal target-sequence-complementary sequence, said second probe being capable of hybridizing to said target sequence adjacently to said first probe,
   wherein, when free in solution or bound non-specifically, the probes are capable of maintaining their stem-loop structures,
   wherein, hybridization of the first probe's loop sequence to the target sequence opens that probe's stem, but hybridization of second probe's terminal target-sequence-complementary sequence to the target sequence does not open that probe's stem, and
   wherein, if the first and second probes are correctly hybridized adjacently on the target sequence, the donating arm of the first probe is single-stranded and capable of hybridizing with the second probe's arm having the single-stranded extension, thereby rendering its HCR or RCA initiator sequence single-stranded.

2. The probe pair according to claim 1, wherein the single-stranded extension of the arm-acceptor probe includes a toehold sequence complementary to the stem-forming portion of the donating arm of the arm-donating probe.

3. The probe pair according to claim 1, wherein the single-stranded extension of the arm-acceptor probe includes only the terminal target-sequence-complementary sequence.

4. The probe pair according to claim 1, wherein the probes are DNA probes.

5. A set of multiple probe pairs according to claim 1, wherein each probe pair hybridizes adjacently to a different subsequence of the target sequence, and wherein each probe pair interacts to generate the same single-stranded HCR initiator sequence.

6. A set of two probe pairs according to claim 1 for detecting two allelic variants of a target sequence, comprising
   a first probe pair that includes an arm-donating probe that hybridizes only to the first allelic variant of said target sequence and an arm-acceptor probe that hybridizes to said target sequence 3' to where that arm-donating probe hybridizes, wherein said first probe pair interacts to generate a first single-stranded HCR initiator sequence; and
   a second probe pair that includes an arm-donating probe that hybridizes only to the second allelic variant of said target sequence an arm-acceptor probe that hybridizes to said target sequence 5' to where that arm-donating probe hybridizes, wherein said second probe pair interacts to generate a second single-stranded HCR initiator sequence that is different from the first single-stranded HCR initiator sequence.

7. A set of two probe pairs according to claim 1 that share the same arm-donating first probe, wherein both arm sequences are donating arms that include single-stranded extensions, wherein, if the first probe and both second probes are correctly hybridized adjacently on the target sequence, each donating arm of the first probe is single-stranded and capable of hybridizing with one second probe's arm having the single-stranded extension, thereby rendering its HCR or RCA initiator sequence single-stranded, and wherein each probe pair interacts to generate a single-stranded HCR initiator sequence for the same pair of HCR monmers.

8. An oligonucleotide set comprising at least one pair of probes according to claim 1 for a selected target sequence and a pair of HCR hairpin oligonucleotide monomers, both labeled with the same fluorophore, that, when free in solution, are capable of maintaining their hairpin structures,
wherein the initiator sequence generated by each of said at least probe pair, is capable of initiating HCR amplification with said monomer pair.

9. An oligonucleotide set comprising two probe pairs according to claim 3,
a first pair of HCR hairpin oligonucleotide monomers, both labeled with a first fluorophore of a first color, and
a second pair of HCR hairpin oligonucleotide monomers, both labeled with a second fluorophore of a different color,
wherein when free in solution, both monomer pairs are capable of maintaining their hairpin structures, and
wherein the first single-stranded initiator sequence is capable of initiating HCR amplification with the first pair of HCR hairpin monomers but not with the second pair, and the second single-stranded initiator sequence is capable of initiating HCR amplification with the second pair of HCR hairpin monomers but not with the first pair.

10. A sm-FISH method for detecting a target sequence in a sample of cells that include, or are suspected of including, nucleic acid target molecules containing the target sequence, comprising:
a) fixing and permeabilizing cells in the sample;
b) washing the fixed and permeabilized cells;
c) incubating the sample containing the washed cells with at least one pair of interacting hairpin hybridization probes according to claim 1 to produce a single-stranded initiator sequence for HCR polymerization or for RCA polymerization;
d) optionally, washing the incubated cells to remove unhybridized probes;
e) after step c) or, if included, step d), adding polymerization reagents and incubating to produce an amplified product, said polymerization reagents comprising, for HCR signal amplification, at least one pair of fluorophore-labeled HCR monomers or, for RCA signal amplification, at least one circular DNA template and DNA polymerase;
f) washing away excess (unused) HCR hairpin oligonucleotide monomers or excess (unused) RCA circular template;
g) for RCA signal amplification, adding and incubating a fluorophore-labeled detector probe for each target sequence; and
h) detecting fluorescence in said cells by microscopy or by flow cytometry.

11. The method according to claim 10, wherein the at least one pair of interacting hairpin hybridization probes consists of a single pair.

12. The method according to claim 10, wherein the cells include, or suspected of including, one or both of two allelic variants of a target sequence, and wherein the at least one pair of interacting hairpin probes comprises two pairs of interactive hairpin probes that comprises:
a first probe pair that includes an arm-donating probe that hybridizes only to the first allelic variant of said target sequence and an arm-acceptor probe that hybridizes to said target sequence 3' to where that arm-donating probe hybridizes, wherein said first probe pair interacts to generate a first single-stranded HCR initiator sequence; and
a second probe pair that includes an arm-donating probe that hybridizes only to the second allelic variant of said target sequence and an arm-acceptor probe that hybridizes to said target sequence 5' to where that arm-donating probe hybridizes, wherein said second probe pair interacts to generate a second single-stranded HCR initiator sequence that is different from the first single-stranded HCR initiator sequence.

13. The probe pair according to claim 2, wherein the probes are DNA probes.

14. The probe pair according to claim 3, wherein the probes are DNA probes.

15. The probe pair according to claim 1, wherein the donating arm of the first probe is complementary to the arm-acceptor hairpin probe's arm that has the single-stranded region.

* * * * *

SEQUENCE LISTING

<160> NUMBER OF SEQ ID NOS: 47

<210> SEQ ID NO 1
<211> LENGTH: 50
<212> TYPE: RNA
<213> ORGANISM: Artificial Sequence
<220> FEATURE:
<223> OTHER INFORMATION: GFP target sequence

```
<400> SEQUENCE: 1
ucgugaccac ccugaccuac ggcgugcagu gcuucagccg cuaccccgac        50

<210> SEQ ID NO 2
<211> LENGTH: 50
<212> TYPE: DNA
<213> ORGANISM: Artificial Sequence
<220> FEATURE:
<223> OTHER INFORMATION: HCR hairpin oligonucleotide H3

<400> SEQUENCE: 2
acagacgact cccacattct ccaggtggga gtcgtctgta acatgaagta        50

<210> SEQ ID NO 3
<211> LENGTH: 50
<212> TYPE: DNA
<213> ORGANISM: Artificial Sequence
<220> FEATURE:
<223> OTHER INFORMATION: HCR hairpin oligonucleotide H4

<400> SEQUENCE: 3
ctggagaatg tgggagtcgt ctgttacttc atgttacaga cgactcccac        50

<210> SEQ ID NO 4
<211> LENGTH: 50
<212> TYPE: DNA
<213> ORGANISM: Artificial Sequence
<220> FEATURE:
<223> OTHER INFORMATION: Passively tagged probe

<400> SEQUENCE: 4
gtcggggtag cggctgaaga aaaatacttc atgttacaga cgactcccac        50

<210> SEQ ID NO 5
<211> LENGTH: 35
<212> TYPE: DNA
<213> ORGANISM: Artificial Sequence
<220> FEATURE:
<223> OTHER INFORMATION: Arm-Donating Hairpin Probe (RDB6.6)

<400> SEQUENCE: 5
gttacagacg actcccacca ctgcacgccg tggga                        35

<210> SEQ ID NO 6
<211> LENGTH: 63
<212> TYPE: DNA
<213> ORGANISM: Artificial Sequence
<220> FEATURE:
<223> OTHER INFORMATION: Arm-Acceptor Hairpin Probe (RA6.3)

<400> SEQUENCE: 6
gtcggggtag cggctgaagg tgggagtcgt ctgtaactac ttcatgttac agacgactcc    60
cac                                                                  63

<210> SEQ ID NO 7
<211> LENGTH: 50
<212> TYPE: DNA
<213> ORGANISM: Artificial Sequence
<220> FEATURE:
<223> OTHER INFORMATION: GFP target sequence variants-C variant

<400> SEQUENCE: 7
ucgugaccac ccugaccuac ggcguccagu gcuucagccg cuaccccgac        50
```

<210> SEQ ID NO 8
<211> LENGTH: 50
<212> TYPE: DNA
<213> ORGANISM: Artificial Sequence
<220> FEATURE:
<223> OTHER INFORMATION: GFP target sequence variants- A variant

<400> SEQUENCE: 8
ucgugaccac ccugaccuac ggcguacagu gcuucagccg cuaccccgac          50

<210> SEQ ID NO 9
<211> LENGTH: 50
<212> TYPE: DNA
<213> ORGANISM: Artificial Sequence
<220> FEATURE:
<223> OTHER INFORMATION: GFP target sequence variants - T variant

<400> SEQUENCE: 9
ucgugaccac ccugaccuac ggcgutcagu gcuucagccg cuaccccgac          50

<210> SEQ ID NO 10
<211> LENGTH: 35
<212> TYPE: DNA
<213> ORGANISM: Artificial Sequence
<220> FEATURE:
<223> OTHER INFORMATION: T variant RDB6.6T

<400> SEQUENCE: 10
gttacagacg actcccacca ctgtacgccg tggga                         35

<210> SEQ ID NO 11
<211> LENGTH: 35
<212> TYPE: DNA
<213> ORGANISM: Artificial Sequence
<220> FEATURE:
<223> OTHER INFORMATION: A variant RDB6.6A

<400> SEQUENCE: 11
gttacagacg actcccacca ctgaacgccg tggga                         35

<210> SEQ ID NO 12
<211> LENGTH: 35
<212> TYPE: DNA
<213> ORGANISM: Artificial Sequence
<220> FEATURE:
<223> OTHER INFORMATION: G variant RDB6.6G

<400> SEQUENCE: 12
gttacagacg actcccacca ctggacgccg tggga                         35

<210> SEQ ID NO 13
<211> LENGTH: 41
<212> TYPE: DNA
<213> ORGANISM: Artificial Sequence
<220> FEATURE:
<223> OTHER INFORMATION: T variant LDB6.1T

<400> SEQUENCE: 13
acgaggcact gtacgcccct cgtaaatcct catcaatcat c                  41

<210> SEQ ID NO 14
<211> LENGTH: 41
<212> TYPE: DNA
<213> ORGANISM: Artificial Sequence
<220> FEATURE:
<223> OTHER INFORMATION: C variant LDB6.1C

```
<400> SEQUENCE: 14
acgaggcact gcacgcccct cgtaaatcct catcaatcat c                          41

<210> SEQ ID NO 15
<211> LENGTH: 41
<212> TYPE: DNA
<213> ORGANISM: Artificial Sequence
<220> FEATURE:
<223> OTHER INFORMATION: A variant LDB6.1A

<400> SEQUENCE: 15
acgaggcact gaacgcccct cgtaaatcct catcaatcat c                          41

<210> SEQ ID NO 16
<211> LENGTH: 41
<212> TYPE: DNA
<213> ORGANISM: Artificial Sequence
<220> FEATURE:
<223> OTHER INFORMATION: G variant LDB6.1G

<400> SEQUENCE: 16
acgaggcact ggacgcccct cgtaaatcct catcaatcat c                          41

<210> SEQ ID NO 17
<211> LENGTH: 80
<212> TYPE: DNA
<213> ORGANISM: Artificial Sequence
<220> FEATURE:
<223> OTHER INFORMATION: Left arm-acceptor hairpin probe LA6.1

<400> SEQUENCE: 17
cctcgtaaat cctcatcaat catccagtaa accgccgatg attgatgagg atttacgagg      60
gtaggtcagg gtggtcacga                                                  80

<210> SEQ ID NO 18
<211> LENGTH: 72
<212> TYPE: DNA
<213> ORGANISM: Artificial Sequence
<220> FEATURE:
<223> OTHER INFORMATION: HCR hairpin oligonucleotide H1

<400> SEQUENCE: 18
ggcggtttac tggatgattg atgaggattt acgaggagct cagtccatcc tcgtaaatcc      60
tcatcaatca tc                                                          72

<210> SEQ ID NO 19
<211> LENGTH: 72
<212> TYPE: DNA
<213> ORGANISM: Artificial Sequence
<220> FEATURE:
<223> OTHER INFORMATION: HCR hairpin oligonucleotide H2

<400> SEQUENCE: 19
cctcgtaaat cctcatcaat catccagtaa accgccgatg attgatgagg atttacgagg      60
atggactgag ct                                                          72

<210> SEQ ID NO 20
<211> LENGTH: 44
<212> TYPE: DNA
<213> ORGANISM: Artificial Sequence
<220> FEATURE:
<223> OTHER INFORMATION: Arm-Donating Hairpin Probe RDB6.3

<400> SEQUENCE: 20
```

-continued gttacagacg actcccacag tccagcactg cacgccgtgg actg           44

<210> SEQ ID NO 21
<211> LENGTH: 71
<212> TYPE: DNA
<213> ORGANISM: Artificial Sequence
<220> FEATURE:
<223> OTHER INFORMATION: Arm-Acceptor Hairpin Probe RA6.2

<400> SEQUENCE: 21
atgtggtcgg ggtagcggct gaggactgtg ggagtcgtct gtaactactt catgttacag     60
acgactccca c                                                         71

<210> SEQ ID NO 22
<211> LENGTH: 39
<212> TYPE: DNA
<213> ORGANISM: Artificial Sequence
<220> FEATURE:
<223> OTHER INFORMATION: Arm-Donating Hairpin Probe RDB6.1

<400> SEQUENCE: 22
gttacagacg actcccacag cactgcacgc cgtgtggga                 39

<210> SEQ ID NO 23
<211> LENGTH: 66
<212> TYPE: DNA
<213> ORGANISM: Artificial Sequence
<220> FEATURE:
<223> OTHER INFORMATION: Arm-Acceptor Hairpin Probe RA6.0

<400> SEQUENCE: 23
atgtggtcgg ggtagcggct gagtgggagt cgtctgtaac tacttcatgt tacagacgac     60
tcccac                                                               66

<210> SEQ ID NO 24
<211> LENGTH: 36
<212> TYPE: DNA
<213> ORGANISM: Artificial Sequence
<220> FEATURE:
<223> OTHER INFORMATION: Arm-Donating Hairpin Probe RDB6.5

<400> SEQUENCE: 24
gttacagacg actcccacag cactgcacgc gtggga                    36

<210> SEQ ID NO 25
<211> LENGTH: 33
<212> TYPE: DNA
<213> ORGANISM: Artificial Sequence
<220> FEATURE:
<223> OTHER INFORMATION: ARM-Donating Hairpin Probe RDB6.7

<400> SEQUENCE: 25
gttacagacg actcccacac tgcacgcgtg gga                       33

<210> SEQ ID NO 26
<211> LENGTH: 44
<212> TYPE: DNA
<213> ORGANISM: Artificial Sequence
<220> FEATURE:
<223> OTHER INFORMATION: Arm-acceptor probe generic hairpin

<400> SEQUENCE: 26
gtgggagtcg tctgtaacta cttcatgtta cagacgactc ccac           44

<210> SEQ ID NO 27
<211> LENGTH: 19
<212> TYPE: DNA
<213> ORGANISM: Artificial Sequence
<220> FEATURE:
<223> OTHER INFORMATION: Arm-acceptor probe specific target-
      complementary sequence

<400> SEQUENCE: 27
gtcggggtag cggctgaag                                                  19

<210> SEQ ID NO 28
<211> LENGTH: 77
<212> TYPE: RNA
<213> ORGANISM: Artificial Sequence
<220> FEATURE:
<223> OTHER INFORMATION: Cox-2 Guide RNA Target Sequence

<400> SEQUENCE: 28
ccgguguacg ucuuuagagg gucgguuuua gagcuagaaa uagcaaguua aaauaaggcu     60
aguccguuau caacuug                                                    77

<210> SEQ ID NO 29
<211> LENGTH: 60
<212> TYPE: DNA
<213> ORGANISM: Artificial Sequence
<220> FEATURE:
<223> OTHER INFORMATION: Arm-Donating Hairpin Probe for Cox-2 Guide RNA
      Target Sequence

<400> SEQUENCE: 29
gttacagacg actcccacag acgaatacag cgcgaccctc taaagacgtt gtattcgtct     60

<210> SEQ ID NO 30
<211> LENGTH: 82
<212> TYPE: DNA
<213> ORGANISM: Artificial Sequence
<220> FEATURE:
<223> OTHER INFORMATION: Arm-Acceptor Probe for Cox-2 Guide RNA Target
      Sequence

<400> SEQUENCE: 30
ttaacttgct atttctagct ctaacgctgt attcgtctgt gggagtcgtc tgtaactact     60
tcatgttaca gacgactccc ac                                              82

<210> SEQ ID NO 31
<211> LENGTH: 80
<212> TYPE: RNA
<213> ORGANISM: Artificial Sequence
<220> FEATURE:
<223> OTHER INFORMATION: Array 3 target sequence

<400> SEQUENCE: 31
ucgacgcgga gaccacgcuc ggcuugucuu ucgcgcgcaa ugcgacgcac gcggauaguu     60
agcugcggcg acgaggcacc                                                 80

<210> SEQ ID NO 32
<211> LENGTH: 90
<212> TYPE: DNA
<213> ORGANISM: Artificial Sequence
<220> FEATURE:
<223> OTHER INFORMATION: Oligonucleotide for circular template

<400> SEQUENCE: 32

```
tttaagcgtc ttaactatta gcgtccagtg aatgcgagtc cgtctaagag agtagtacag      60
cagccgtcaa gagtgtctag ttctgtcata                                       90
```

<210> SEQ ID NO 33
<211> LENGTH: 26
<212> TYPE: DNA
<213> ORGANISM: Artificial Sequence
<220> FEATURE:
<223> OTHER INFORMATION: Splint oligonucleotide for circular template

<400> SEQUENCE: 33

```
taagacgctt aaatatgaca gaacta                                           26
```

<210> SEQ ID NO 34
<211> LENGTH: 55
<212> TYPE: DNA
<213> ORGANISM: Artificial Sequence
<220> FEATURE:
<223> OTHER INFORMATION: Arm-donating hairpin oligonucleotide, RDB RCA

<400> SEQUENCE: 34

```
gcttaaatat gacagaacta agtccgaaag acaagccgag cgtggtctcc ggact           55
```

<210> SEQ ID NO 35
<211> LENGTH: 73
<212> TYPE: DNA
<213> ORGANISM: Artificial Sequence
<220> FEATURE:
<223> OTHER INFORMATION: Arm-acceptor hairpin oligonucleotide, RA RCA

<400> SEQUENCE: 35

```
ccgcgtgcgt cgcattgcgc gcggacttag ttctgtcata tttaagctaa gacgcttaaa      60
tatgacagaa cta                                                         73
```

<210> SEQ ID NO 36
<211> LENGTH: 20
<212> TYPE: DNA
<213> ORGANISM: Artificial Sequence
<220> FEATURE:
<223> OTHER INFORMATION: Detector Probe for RCA product

<400> SEQUENCE: 36

```
tgcgagtccg tctaagagag                                                  20
```

<210> SEQ ID NO 37
<211> LENGTH: 1218
<212> TYPE: DNA
<213> ORGANISM: Homo sapiens

<400> SEQUENCE: 37

```
gtgcagcaca ttgttctgat catctgaaga tcagctatta gaagagaaag atcagttaag      60
tcctttggac ctgatcagct tgatacaaga actactgatt tcaacttctt tggcttaatt     120
ctctcggaaa cgatgaaata tacaagttat atcttggctt tcagctctg catcgttttg      180 ggttctcttg gctgttactg ccaggaccca tatgtaaaag aagcagaaaa ccttaagaaa     240
tattttaatg caggtcattc agatgtagcg gataatggaa ctcttttctt aggcattttg     300
aagaattgga agaggagag tgacagaaaa ataatgcaga gccaaattgt ctccttttac     360
ttcaaacttt ttaaaaactt taaagatgac cagagcatcc aaaagagtgt ggagaccatc     420
aaggaagaca tgaatgtcaa gttttcaat agcaacaaaa agaaacgaga tgacttcgaa     480
aagctgacta attattcggt aactgacttg aatgtccaac gcaaagcaat acatgaactc     540
```

```
atccaagtga tggctgaact gtcgccagca gctaaaacag ggaagcgaaa aaggagtcag    600
atgctgtttc gaggtcgaag agcatcccag taatggttgt cctgcctgca atatttgaat    660
tttaaatcta aatctattta ttaatatta acattattta tatggggaat atattttag      720 actcatcaat caaataagta tttataatag caacttttgt gtaatgaaaa tgaatatcta    780
ttaatatatg tattatttat aattcctata tcctgtgact gtctcactta atcctttgtt    840
ttctgactaa ttaggcaagg ctatgtgatt acaaggcttt atctcagggg ccaactaggc    900
agccaaccta agcaagatcc catgggttgt gtgtttattt cacttgatga tacaatgaac    960
acttataagt gaagtgatac tatccagtta ctgccggttt gaaaatatgc ctgcaatctg   1020
agccagtgct ttaatggcat gtcagacaga acttgaatgt gtcaggtgac cctgatgaaa   1080
acatagcatc tcaggagatt tcatgcctgg tgcttccaaa tattgttgac aactgtgact   1140
gtacccaaat ggaaagtaac tcatttgtta aaattatcaa tatctaatat atatgaataa   1200
agtgtaagtt cacaacta                                                 1218

<210> SEQ ID NO 38
<211> LENGTH: 31
<212> TYPE: DNA
<213> ORGANISM: Artificial Sequence
<220> FEATURE:
<223> OTHER INFORMATION: appended sequence

<400> SEQUENCE: 38
aaaaatactt catgttacag acgactccca c                                    31

<210> SEQ ID NO 39
<211> LENGTH: 30
<212> TYPE: DNA
<213> ORGANISM: Artificial Sequence
<220> FEATURE:
<223> OTHER INFORMATION: right arm-donating hairpin probe
<220> FEATURE:
<221> NAME/KEY: misc_feature
<222> LOCATION: (19)..(24)
<223> OTHER INFORMATION: n is a, c, g, or t

<400> SEQUENCE: 39
gttacagacg actcccacnn nnnngtggga                                      30

<210> SEQ ID NO 40
<211> LENGTH: 17
<212> TYPE: DNA
<213> ORGANISM: Artificial Sequence
<220> FEATURE:
<223> OTHER INFORMATION: right arm

<400> SEQUENCE: 40
gttacagacg actccca                                                    17

<210> SEQ ID NO 41
<211> LENGTH: 6
<212> TYPE: DNA
<213> ORGANISM: Artificial Sequence
<220> FEATURE:
<223> OTHER INFORMATION: complementary sequence

<400> SEQUENCE: 41 gtggga                                                                 6

<210> SEQ ID NO 42
```

<211> LENGTH: 3633
<212> TYPE: DNA
<213> ORGANISM: Homo sapiens

<400> SEQUENCE: 42

| | | | | | |
|---|---|---|---|---|---|
| atgcgaccct | ccgggacggc | cggggcagcg | ctcctggcgc | tgctggctgc | gctctgcccg 60 |
| gcgagtcggg | ctctggagga | aaagaaagtt | tgccaaggca | cgagtaacaa | gctcacgcag 120 |
| ttgggcactt | tgaagatca | ttttctcagc | ctccagagga | tgttcaataa | ctgtgaggtg 180 |
| gtccttggga | atttggaaat | tacctatgtg | cagaggaatt | atgatctttc | cttcttaaag 240 |
| accatccagg | aggtggctgg | ttatgtcctc | attgccctca | acacagtgga | gcgaattcct 300 |
| ttggaaaacc | tgcagatcat | cagaggaaat | atgtactacg | aaaattccta | tgccttagca 360 |
| gtcttatcta | actatgatgc | aaataaaacc | ggactgaagg | agctgcccat | gagaaattta 420 |
| caggaaatcc | tgcatggcgc | cgtgcggttc | agcaacaacc | ctgccctgtg | caacgtggag 480 |
| agcatccagt | ggcgggacat | agtcagcagt | gactttctca | gcaacatgtc | gatggacttc 540 |
| cagaaccacc | tgggcagctg | ccaaaagtgt | gatccaagct | gtcccaatgg | agctgctgg 600 |
| ggtgcaggag | aggagaactg | ccagaaactg | accaaaatca | tctgtgccca | gcagtgctcc 660 |
| gggcgctgcc | gtgcaagtc | ccccagtgac | tgctgccaca | accagtgtgc | tgcaggctgc 720 |
| acaggccccc | gggagagcga | ctgcctggtc | tgccgcaaat | ccgagacga | agccacgtgc 780 |
| aaggacacct | gccccccact | catgctctac | aaccccacca | cgtaccagat | ggatgtgaac 840 |
| cccgagggca | atacagcctt | tggtgccacc | tgcgtgaaga | agtgtccccg | taattatgtg 900 |
| gtgacagatc | acggctcgtg | cgtccgagcc | tgtggggccg | acagctatga | gatggaggaa 960 |
| gacggcgtcc | gcaagtgtaa | gaagtgcgaa | gggccttgcc | gcaaagtgtg | taacggaata 1020 |
| ggtattggtg | aatttaaaga | ctcactctcc | ataaatgcta | cgaatattaa | acacttcaaa 1080 |
| aactgcacct | ccatcagtgg | cgatctccac | atcctgccgg | tggcatttag | gggtgactcc 1140 |
| ttcacacata | ctcctcctct | ggatccacag | gaactggata | ttctgaaaac | cgtaaaggaa 1200 |
| atcacagggt | ttttgctgat | tcaggcttgg | cctgaaaaca | ggacggacct | ccatgccttt 1260 |
| gagaacctag | aaatcatacg | cggcaggacc | aagcaacatg | gtcagttttc | tcttgcagtc 1320 |
| gtcagcctga | acataacatc | cttgggatta | cgctccctca | aggagataag | tgatggagat 1380 |
| gtgataattt | caggaaacaa | aaatttgtgc | tatgcaaata | caataaactg | gaaaaaactg 1440 |
| tttgggacct | ccggtcagaa | aaccaaaatt | ataagcaaca | gaggtgaaaa | cagctgcaag 1500 |
| gccacaggcc | aggtctgcca | tgccttgtgc | tcccccgagg | gctgctgggg | cccggagccc 1560 |
| agggactgcg | tctcttgccg | gaatgtcagc | cgaggcaggg | aatgcgtgga | caagtgcaac 1620 |
| cttctggagg | gtgagccaag | ggagtttgtg | gagaactctg | agtgcataca | gtgccaccca 1680 |
| gagtgcctgc | ctcaggccat | gaacatcacc | tgcacaggac | ggggaccaga | caactgtatc 1740 |
| cagtgtgccc | actacattga | cggccccac | tgcgtcaaga | cctgcccggc | aggagtcatg 1800 |
| ggagaaaaca | acaccctggt | ctggaagtac | gcagacgccg | ccatgtgtg | ccacctgtgc 1860 |
| catccaaact | gcacctacgg | atgcactggg | ccaggtcttg | aaggctgtcc | aacgaatggg 1920 |
| cctaagatcc | cgtccatcgc | cactgggatg | gtggggccc | tcctcttgct | gctggtggtg 1980 |
| gccctgggga | tcggcctctt | catgcgaagg | cgccacatcg | ttcggaagcg | cacgctgcgg 2040 |
| aggctgctgc | aggagaggga | gcttgtggag | cctcttacac | ccagtggaga | agctcccaac 2100 |
| caagctctct | tgaggatctt | gaaggaaact | gaattcaaaa | agatcaaagt | gctgggctcc 2160 |
| ggtgcgttcg | gcacggtgta | taagggactc | tggatcccag | aaggtgagaa | agttaaaatt 2220 |

-continued

```
cccgtcgcta tcaaggaatt aagagaagca acatctccga aagccaacaa ggaaatcctc    2280
gatgaagcct acgtgatggc cagcgtggac aaccccacg  tgtgccgcct gctgggcatc    2340
tgcctcacct ccaccgtgca gctcatcacg cagctcatgc ccttcggctg cctcctggac    2400
tatgtccggg aacacaaaga caatattggc tcccagtacc tgctcaactg gtgtgtgcag    2460
atcgcaaagg gcatgaacta cttggaggac cgtcgcttgg tgcaccgcga cctggcagcc    2520
aggaacgtac tggtgaaaac accgcagcat gtcaagatca cagattttgg gctggccaaa    2580
ctgctgggtg cggaagagaa agaataccat gcagaaggag gcaaagtgcc tatcaagtgg    2640
atggcattgg aatcaattt  acacagaatc tatacccacc agagtgatgt ctggagctac    2700
ggggtgactg tttgggagtt gatgacccttt ggatccaagc catatgacgg aatccctgcc    2760
agcgagatct cctccatcct ggagaaagga gaacgcctcc ctcagccacc catatgtacc    2820
atcgatgtct acatgatcat ggtcaagtgc tggatgatag acgcagatag tcgcccaaag    2880
ttccgtgagt tgatcatcga attctccaaa atggcccgag accccagcg  ctaccttgtc    2940 attcagggg  atgaaagaat gcatttgcca agtcctacag actccaactt ctaccgtgcc    3000
ctgatggatg aagaagacat ggacgacgtg gtggatgccg acgagtacct catcccacag    3060
cagggcttct tcagcagccc ctccacgtca cggactcccc tcctgagctc tctgagtgca    3120
accagcaaca attccaccgt ggcttgcatt gatagaaatg ggctgcaaag ctgtcccatc    3180
aaggaagaca gcttcttgca gcgatacagc tcagacccca caggcgcctt gactgaggac    3240
agcatagacg acaccttcct cccagtgcct gaatacataa accagtccgt tcccaaaagg    3300
cccgctggct ctgtgcagaa tcctgtctat cacaatcagc ctctgaaccc cgcgcccagc    3360
agagacccac actaccagga  cccccacagc actgcagtgg caaccccga  gtatctcaac    3420 actgtccagc ccacctgtgt caacagcaca ttcgacagcc ctgccactg  ggcccagaaa    3480 ggcagccacc aaattagcct ggacaaccct gactaccagc aggacttctt tcccaaggaa    3540
gccaagccaa atggcatctt taagggctcc acagctgaaa atgcagaata cctaagggtc    3600
gcgccacaaa gcagtgaatt tattggagca tga                                  3633
```

<210> SEQ ID NO 43
<211> LENGTH: 46
<212> TYPE: DNA
<213> ORGANISM: Artificial Sequence
<220> FEATURE:
<223> OTHER INFORMATION: Right arm-donating hairpin probe EGFR 3.1
      (mutant)

<400> SEQUENCE: 43

```
gttacagacg actcccacag tccgtttggc ccgcccaaaa tggact          46
```

<210> SEQ ID NO 44
<211> LENGTH: 52
<212> TYPE: DNA
<213> ORGANISM: Artificial Sequence
<220> FEATURE:
<223> OTHER INFORMATION: Left arm-donating hairpin probe EGFR 3.0
      (wild-type)

<400> SEQUENCE: 44

```
taggtgtttg gccagcccaa aatacctacc tcgtaaatcc tcatcaatca tc        52
```

<210> SEQ ID NO 45
<211> LENGTH: 88
<212> TYPE: DNA

```
<213> ORGANISM: Artificial Sequence
<220> FEATURE:
<223> OTHER INFORMATION: Right acceptor hairpin probe EGFR 3.0

<400> SEQUENCE: 45
ctccttctgc atggtattct ttctcttccg cacccagcag gactgtggga gtcgtctgta    60
actacttcat gttacagacg actcccac                                      88

<210> SEQ ID NO 46
<211> LENGTH: 90
<212> TYPE: DNA
<213> ORGANISM: Artificial Sequence
<220> FEATURE:
<223> OTHER INFORMATION: Left acceptor hairpin probe EGFR 3.0

<400> SEQUENCE: 46
cctcgtaaat cctcatcaat catccagtaa accgccgatg attgatgagg atttaggagg    60
taggtctgtg atcttgacat gctgcggtgt                                    90

<210> SEQ ID NO 47
<211> LENGTH: 20
<212> TYPE: DNA
<213> ORGANISM: Homo sapiens

<400> SEQUENCE: 47
cctacggcgt gcagtgcttc                                               20
```